(12) United States Patent
Jeschke et al.

(10) Patent No.: US 7,772,190 B2
(45) Date of Patent: Aug. 10, 2010

(54) DIDEPSIPEPTIDE-BASED ENDOPARASITICIDES, NEW DIDEPSIPEPTIDES AND PROCESS FOR PREPARING THE SAME

(75) Inventors: Peter Jeschke, Leverkusen (DE); Jürgen Scherkenbeck, Wermelskirchen (DE); Andrew Plant, Leverkusen (DE); Achim Harder, Köln (DE); Norbert Mencke, Leverkusen (DE)

(73) Assignee: Bayer Animal Health GmbH (DE)

( * ) Notice: Subject to any disclaimer, the term of this patent is extended or adjusted under 35 U.S.C. 154(b) by 1023 days.

(21) Appl. No.: 10/290,827

(22) Filed: Nov. 8, 2002

(65) Prior Publication Data

US 2004/0034048 A1 Feb. 19, 2004

Related U.S. Application Data

(63) Continuation of application No. 09/011,599, filed as application No. PCT/EP96/03355 on Jul. 30, 1996, now abandoned.

(30) Foreign Application Priority Data

Aug. 11, 1995 (DE) .................................. 195 29 604

(51) Int. Cl.
*C07K 5/06* (2006.01)

(52) U.S. Cl. ............................ 514/19; 530/331; 514/18
(58) Field of Classification Search .................. 514/19, 514/18; 530/331
See application file for complete search history.

(56) References Cited

U.S. PATENT DOCUMENTS 5,571,793 A * 11/1996 Scherkenbeck et al. ....... 514/19
5,777,075 A * 7/1998 Scherkenbeck et al. ..... 530/330

* cited by examiner

*Primary Examiner*—David Lukton

(57) ABSTRACT

The present invention relates to the use of didepsipeptides of the general formula (I) and their salts

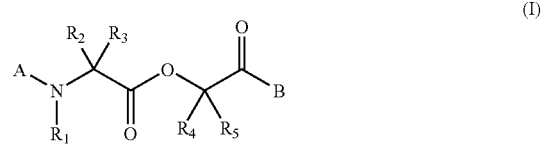

(I)

in which the radicals have the meaning given in the description, and to new didepsipeptides and processes for their preparation.

2 Claims, No Drawings

DIDEPSIPEPTIDE-BASED ENDOPARASITICIDES, NEW DIDEPSIPEPTIDES AND PROCESS FOR PREPARING THE SAME

This application is a continuation of Ser. No. 09/011,599, filed Feb. 3, 1998, now abandoned, which is a national stage entry of PCT/EP96/03355, filed Jul. 30, 1996, which claims foreign priority to 19529604.4, filed Aug. 11, 1995.

The present invention relates to the use of didepsipeptides for the control of endoparasites, to new didepsipeptides and to processes for their preparation.

Certain didepsipeptides are, as starting substances for endoparasiticidally active cyclic depsipeptides (cf. total synthesis of PF 1022 A: JP Pat. 05 229 997; Makoto Ohyama et al., Biosci. Biotech. Biochem. 58 (6), 1994, pp. 1193-1194; Makio Kobayshi et al., Annu. Rep. Sankyo Res. Lab. 46, 1994, pp. 67-75; Stephen J. Nelson et al., J. Antibiotics 47, (11), 1994, pp. 1322-1327; cyclooctadepsipeptides: WO 93/19053, EP 0 634 408 A1; WO 94/19334; WO 95/07272; EP 626 375; EP 626 376; cyclohexadepsipeptides: DE-OS [German Published Specification] 4342 907; WO 93/25543) and open-chain depsipeptides, for example octadepsipeptides (DE-OS [German Published Specification] 4 341 993), hexadepsipeptides (DE-OS [German Published Specification] 4 341 992) or tetradepsipeptides (DE-OS [German Published Specification] 4 341 991), the subject of prior-published patent applications and publications. Some of these abovementioned didepsipeptides are also the subject of non-prior-published German Patent Applications (P 44 40 193.0; P 44 01 389.2).

The present invention relates to:
1. The use of didepsipeptides of the general formula (I) and their salts

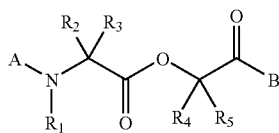
(I)

in which
$R^1$ represent hydrogen, straight-chain or branched alkyl, cycloalkyl, arylalkyl, aryl, heteroaryl, heteroarylalkyl, each of which is optionally substituted,
$R^1$ and $R^2$ together with the atoms to which they are bonded represent a 5- or 6-membered ring which can optionally be interrupted by oxygen, sulphur, sulphoxyl or sulphonyl and is optionally substituted,
$R^2$ and $R^3$ independently of one another represent hydrogen, straight-chain or branched alkyl, alkenyl, cycloalkyl, cycloalkylalkyl, aryl, arylalkyl, heteroaryl, heteroarylalkyl, each of which is optionally substituted, or
$R^2$ and $R^3$ together represent a spirocyclic ring, which is optionally substituted,
$R^4$ and $R^5$ independently of one another represent hydrogen, straight-chain or branched alkyl, alkenyl, cycloalkyl, cycloalkylalkyl, aryl, arylalkyl, heteroaryl, heteroarylalkyl, each of which is optionally substituted, or
$R^4$ and $R^5$ together represent a spirocyclic ring, which is optionally substituted, A represents hydrogen, alkyl, aralkyl, formyl, alkoxydicarbonyl or a radical of the group $G^1$

(G¹)

in which

can denote carboxyl, thiocarboxyl, —CH═CH—NO₂, —CH═CH—CN, —C═N—$R^6$, sulphoxyl, sulphonyl, —P(O)—$OR^7$ or P(S)—$OR^7$,
$R^6$ represents hydrogen, hydroxyl, alkoxy, alkylcarbonyl, halogenoalkylcarbonyl, alkylsulphonyl, nitro or cyano, and
$R^7$ represents hydrogen or alkyl, and
Q represents straight-chain or branched alkyl, alkenyl, alkinyl, cycloalkyl, aryl, arylalkyl, hetaryl or hetarylalkyl, each of which is optionally substituted, or optionally represents a radical from the group $G^2$ and $G^3$

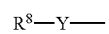
(G²)

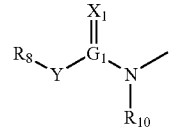
(G³)

in which

can denote carboxyl, thiocarboxyl or sulphonyl,
Y represents oxygen, sulphur or —$NR^9$,
$R^8$ in the case where Y represents nitrogen can denote a cyclic amino group linked via a nitrogen atom,
$R^8$ and $R^9$ independently of one another represent hydrogen, straight-chain or branched alkyl, alkenyl, alkinyl, cycloalkyl, cycloalkylalkyl, aryl, arylalkyl, hetaryl, hetarylalkyl, each of which is optionally substituted, or
$R^8$ and $R^9$ together with the adjacent N atom [lacuna] a carbocyclic 5-, 6- or 7-membered ring system or a 7 to 10-membered bicyclic ring system which can optionally also be interrupted by oxygen, sulphur, sulphoxyl, sulphonyl, carbonyl, —N—O—, —N═, —$NR^{11}$— or by quaternized nitrogen and is optionally substituted,
$R^{10}$ represents hydrogen or alkyl,
$R^{11}$ represent represents hydrogen, straight-chain or branched alkyl, alkenyl, alkinyl, cycloalkyl, cycloalkylalkyl, alkoxycarbonyl, alkylcarbonyl, cycloalkylcarbonyl, cyano, aryl, arylalkyl, hetaryl, hetarylalkyl, each of which is optionally substituted, and B represents hydroxyl, alkoxy, alkenyloxy, alkinyloxy, cycloalkyloxy, cycloalkylalkyloxy, aryloxy-, arylalkyloxy, hetaryloxy, hetarylalkyloxy, each of which is optionally substituted, or
represents the radicals —NR$^{12}$R$^{13}$, —NR$^{14}$—NR$^{12}$R$^{13}$ and —NR$^{15}$—OR$^{16}$,
in which
R$^{12}$ and R$^{13}$ independently of one another represent hydrogen, straight-chain or branched alkyl, alkylcarbonyl, alkylsulphonyl, alkenyl, alkinyl, cycloalkyl, cycloalkylalkyl, aryl, arylcarbonyl, arylsulphonyl, arylalkyl, hetaryl, hetarylcarbonly, hetarylsulphonyl or hetarylalkyl, each of which is optionally substituted, or
R$^{12}$ and R$^{13}$ together with the adjacent N atom [lacuna] a carbocyclic 5-, 6-, 7- or 8-membered ring system or a 7 to 10-membered bicyclic ring system which can optionally also be interrupted by oxygen, sulphur, sulphoxyl, sulphonyl, carbonyl, —N—O—, —N=, —NR$^{11}$— or by quaternized nitrogen and is optionally substituted,
R$^{14}$ represents hydrogen, straight-chain or branched alkyl, cycloalkyl, arylalkyl or hetarylalkyl, each of which is optionally substituted,
R$^{15}$ and R$^{16}$ independently of one another denote hydrogen, straight-chain or branched alkyl, alkylcarbonyl, alkenyl, alkinyl, cycloalkyl, cycloalkylalkyl, arylalkyl or hetarylalkyl, each of which is optionally substituted,
R$^{15}$ and R$^{16}$ together with the adjacent N—O-group represent a carbocyclic 5-, 6- or 7-membered ring, and their optical isomers and racemates, for the control of endoparasites in medicine and veterinary medicine.

Preferably used didepsipeptides are those of the general formula (I) and their salts

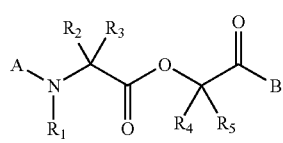

(I)

in which
R$^1$ represent hydrogen, straight-chain or branched alkyl having up to 6 carbon atoms, C$_{3-6}$-cycloalkyl, aryl-C$_{1-2}$-alkyl or het-C$_{1-2}$-alkyl, each of which is optionally substituted,
R$^1$ and R$^2$ together with the atoms to which they are bonded represent a 5- or 6-membered ring which can optionally be interrupted by sulphur and is optionally substituted,
R$^2$ and R$^3$ independently of one another represent hydrogen, straight-chain or branched alkyl having up to 6 carbon atoms, halogenoalkyl, hydroxyalkyl, C$_{1-4}$-alkanoyloxyalkyl, C$_{1-2}$-alkoxyalkyl, mercaptoalkyl, C$_{1-2}$-alkylthioalkyl, C$_{1-2}$-alkylsulphinylalkyl, C$_{1-2}$-alkylsulphonylalkyl, carboxyalkyl, carbamoylalkyl, aminoalkyl, C$_{1-6}$-alkylaminoalkyl, C$_{1-6}$-dialkylaminoalkyl, guanidinoalkyl, which can optionally be substituted by one or two benzyloxycarbonyl radicals or by one, two, three or four C$_{1-2}$-alkyl radicals, C$_{1-4}$-alkoxycarbonylaminoalkyl, C$_{2-6}$-alkenyl, C$_{3-6}$-cycloalkyl, C$_{3-6}$-cycloalkyl-C$_{1-2}$-alkyl, and optionally substituted aryl, aryl-C$_{1-2}$-alkyl, heteroaryl, heteroaryl-C$_{1-2}$-alkyl, or R$^2$ and R$^3$ together represent a spirocyclic ring, R$^4$ and R$^5$ independently of one another represent hydrogen, straight-chain or branched alkyl having up to 6 carbon atoms, halogenoalkyl, hydroxyalkyl, C$_{1-4}$-alkanoyloxyalkyl, C$_{1-2}$-alkoxyalkyl, mercaptoalkyl, C$_{1-2}$-alkylthioalkyl, C$_{1-2}$-alkylsulphinylalkyl, C$_{1-2}$-alkylsulphonylalkyl, carboxyalkyl, carbamoylalkyl, aminoalkyl, C$_{1-6}$-alkylaminoalkyl, C$_{1-6}$-dialkylaminoalkyl, guanidinoalkyl, which can optionally be substituted by one or two benzyloxycarbonyl radicals or by one, two, three or four C$_{1-2}$-alkyl radicals, C$_{1-4}$-alkoxycarbonylaminoalkyl, C$_{2-6}$-alkenyl, C$_{3-6}$-cycloalkyl, C$_{3-6}$-cycloalkyl-C$_{1-2}$-alkyl, and optionally substituted aryl, aryl-C$_{1-2}$-alkyl, heteroaryl, heteroaryl-C$_{1-2}$alkyl, or R$^4$ and R$^5$ together represent a spirocyclic ring, A represents hydrogen, C$_{1-6}$-alkyl, aryl-C$_{1-2}$-alkyl, formyl, C$_{1-4}$-alkoxydicarbonyl or a radical of the group G$^1$

(G$^1$)

in which

can denote carboxyl, thiocarboxyl, —C=CH—NO$_2$, —C=CH—CN, —C=N—R$^6$, sulphoxyl, sulphonyl, —P(O)—OR$^7$ or P(S)—OR$^7$, R$^6$ represents hydrogen, hydroxyl, C$_{1-4}$-alkoxy, C$_{1-4}$-alkylcarbonyl, C$_{1-4}$-halogenoalkylcarbonyl, C$_{1-4}$-alkylsulphonyl, nitro or cyano, and R$^7$ represents hydrogen or C$_{1-4}$-alkyl, and Q represents straight-chain or branched C$_{1-6}$-alkyl, C$_{1-6}$-halogenoalkyl, hydroxy-C$_{1-6}$-alkyl, C$_{1-4}$-alkanoyloxy-C$_{1-6}$-alkyl, C$_{1-2}$-alkoxy-C$_{1-6}$-alkyl, mercapto-C$_{1-6}$-alkyl, C$_{1-2}$-alkylthio-C$_{1-6}$-alkyl, C$_{1-2}$-alkylsulphinyl-C$_{1-6}$-alkyl, C$_{1-2}$-alkylsulphonyl-C$_{1-6}$-alkyl, carboxy-C$_{1-6}$-alkyl, carbamoyl-C$_{1-6}$-alkyl, amino-C$_{1-6}$-alkyl, C$_{1-6}$-alkylamino-C$_{1-6}$-alkyl, C$_{1-6}$-dialkylaminoalkyl, C$_{2-6}$-alkenyl, C$_{2-6}$-alkinyl, C$_{2-6}$-halogenoalkenyl, C$_{3-6}$-cycoalkyl, and optionally substituted aryl, aryl-C$_{1-2}$-aryl, hetaryl or hetaryl-C$_{1-2}$-alkyl, or optionally represents a radical from the group G$^2$ and G$^3$ (G$^2$)

R$^8$—Y—

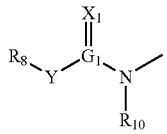

(G³)

in which

can denote carboxyl, thiocarboxyl or sulphonyl,

Y represents oxygen, sulphur or —NR⁹,

R⁸ in the case where Y represents nitrogen can denote a cyclic amino group linked via a nitrogen atom, R⁸ and R⁹ independently of one another represent hydrogen, straight-chain or branched $C_{1-6}$-alkyl, $C_{1-6}$-alkenyl, $C_{1-6}$-alkinyl, $C_{3-6}$-cycloalkyl, $C_{3-6}$-cycloalkyl-$C_{1-2}$-alkyl, aryl, arylalkyl, hetaryl, hetarylalkyl, each of which is optionally substituted, or R⁸ and R⁹ together with the adjacent N atom [lacuna] a carbocyclic 5-, 6- or 7-membered ring system or a 7 to 10-membered bicyclic ring system which can optionally also be interrupted by oxygen, sulphur, sulphoxyl, sulphonyl, carbonyl, —N—O, —N═, —NR¹¹— or by quaternized nitrogen and is optionally substituted, R¹⁰ represents hydrogen or $C_{1-4}$-alkyl, R¹¹ represents hydrogen, straight-chain or branched $C_{1-6}$-alkyl, $C_{2-6}$-alkenyl, $C_{2-6}$-alkinyl, $C_{3-8}$-cycloalkyl, $C_{3-8}$-cycloalkyl-$C_{1-2}$-alkyl, $C_{1-4}$-alkoxycarbonyl, $C_{1-4}$-alkylcarbonyl, $C_{3-6}$-cycloalkylcarbonyl, cyan, aryl, aryl-$C_{1-2}$-alkyl, hetaryl, hetaryl-$C_{1-2}$-alkyl, each of which is optionally substituted, and B represents hydroxyl, $C_{1-6}$-alkoxy, $C_{2-6}$-alkenyloxy, $C_{2-6}$-alkinyloxy, $C_{3-7}$-cycloalkyloxy, $C_{3-7}$-cycloalkylalkyloxy, aryloxy-, aryl-$C_{1-2}$-alkyloxy, hetaryloxy, hetaryl-$C_{1-2}$-alkyloxy, each of which is optionally substituted, or represents the radicals —NR¹²R¹³, —NR¹⁴—NR¹²R¹³ and —NR¹⁵—OR¹⁶, in which R¹² and R¹³ independently of one another represent hydrogen, straight-chain or branched $C_{1-6}$-alkyl, $C_{1-6}$-alkylcarbonyl, $C_{1-6}$-alkylsulphonyl, $C_{2-6}$-alkenyl, $C_{2-6}$-alkinyl, $C_{3-8}$-cycloalkyl, $C_{3-8}$-cycloalkyl-$C_{1-2}$-alkyl, aryl, arylcarbonyl, arylsulphonyl, aryl-$C_{1-2}$-alkyl, hetaryl, hetarylcarbonyl, hetarylsulphonyl or hetaryl-$C_{1-2}$-alkyl, each of which is optionally substituted, or R¹² and R¹³ together with the adjacent N atom [lacuna] a carbocyclic 5-, 6-, 7- or 8-membered ring system or a 7 to 10-membered bicyclic ring system, which can optionally also be interrupted by oxygen, sulphur, sulphoxyl, sulphonyl, carbonyl, —N—O—, —N═, —NR¹¹— or by quaternized nitrogen and is optionally substituted, R¹⁴ represents hydrogen, straight-chain or branched $C_{1-6}$-alkyl, $C_{3-6}$-cycloalkyl, aryl-$C_{1-2}$-alkyl, hetaryl-$C_{1-2}$-alkyl, each of which is optionally substituted, R¹⁵ and R¹⁶ independently of one another denote hydrogen, straight-chain or branched $C_{1-6}$-alkyl, $C_{1-6}$-alkylcarbonyl, $C_{2-6}$-alkenyl, $C_{2-6}$-alkinyl, $C_{3-6}$-cycloalkyl, $C_{3-6}$-cycloalkyl-$C_{1-2}$-alkyl, aryl-$C_{1-2}$-alkyl or hetaryl-$C_{1-2}$-alkyl, each of which is optionally substituted, R¹⁵ and R¹⁶ together with the adjacent N—O-group represent a carbocyclic 5-, 6- or 7-membered ring, and their optical isomers and racemates, for the control of endoparasites in medicine and veterinary medicine.

The compounds of the formula (I) are known in some cases and can be prepared analogously to known processes.

The invention further relates to:

2. New didepsipeptides of the general formula (Ia) and their salts

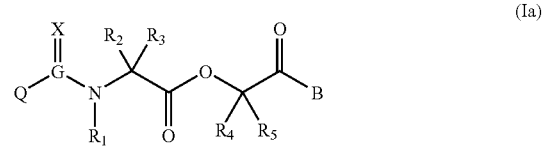

in which

R¹ represents hydrogen, straight-chain or branched $C_{1-4}$-alkyl, $C_{3-6}$-cycloalkyl, aryl-$C_{1-2}$-alkyl or hetaryl-$C_{1-2}$-alkyl, each of which is optionally substituted, and R¹ and R² together with the atoms to which they are bonded represent a 5- or 6-membered ring which can optionally be interrupted by oxygen, sulphur, sulphoxyl or sulphonyl and is optionally substituted, R² represents hydrogen, straight-chain or branched alkyl having up to 6 carbon atoms, alkenyl having up to 4 carbon atoms, $C_{3-6}$-cycloalkyl, $C_{3-6}$-cycloalkyl-$C_{1-2}$-alkyl, aryl, aryl-$C_{1-2}$-alkyl, hetaryl, hetaryl-$C_{1-2}$-alkyl each of which is optionally substituted, R³ and R⁴ represent hydrogen, R⁵ represents straight-chain or branched alkyl having up to 6 carbon atoms, alkenyl having up to 4 carbon atoms, $C_{3-6}$-cycloalkyl, $C_{3-6}$-cycloalkyl-$C_{1-2}$-alkyl, aryl, aryl-$C_{1-2}$-alkyl, hetaryl, hetaryl-$C_{1-2}$-alkyl each of which is optionally substituted,

represents carboxyl, thiocarboxyl, —C═CH—NO₂, —C═CH—CN, —C═N—R⁶, sulphoxyl, sulphonyl, —P(O)—OR⁷ or P(S)—OR⁷, R⁶ represents hydrogen, hydroxyl, $C_{1-4}$-alkoxy, $C_{1-4}$-alkylcarbonyl, $C_{1-4}$-halogenoalkylcarbonyl, $C_{1-4}$-alkylsulphonyl, nitro or cyano, and R⁷ represents hydrogen or $C_{1-4}$-alkyl, and Q represents straight-chain or branched $C_{1-6}$-alkyl, $C_{2-6}$-alkenyl, $C_{2-6}$-alkinyl, $C_{3-6}$-cycloalkyl or hetaryl-$C_{1-2}$-alkyl, each of which is optionally substituted, or optionally represents a radical from the group G² and G³

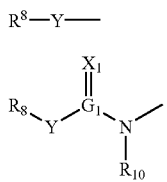

in which

can denote carboxyl, thiocarboxyl or sulphonyl,
Y represents oxygen, sulphur or —NR$^9$,
R$^8$ in the case where Y represents nitrogen can denote a cyclic amino group linked via a nitrogen atom,
R$^8$ and R$^9$ independently of one another represents hydrogen, straight-chain or branched C$_{1-6}$-alkyl, C$_{2-6}$-alkenyl, C$_{2-6}$-alkinyl, C$_{3-6}$-cycloalkyl, C$_{3-6}$-cycloalkyl-C$_{1-2}$-alkyl, hetaryl or hetaryl-C$_{1-2}$-alkyl, each of which is optionally substituted, or
R$^8$ and R$^9$ together with the adjacent N atom represent a carbocyclic 5-, 6- or 7-membered ring system or a 7 to 10-membered bicyclic ring system which can optionally also be interrupted by oxygen, sulphur, sulphoxyl, sulphonyl, carbonyl, —N—O—, —N═, —NR$^{11}$— or by quaternized nitrogen and is optionally substituted,
R$^{10}$ represents hydrogen or C$_{1-4}$-alkyl, and
R$^{11}$ represents hydrogen, straight-chain or branched C$_{1-6}$-alkyl, C$_{3-6}$-cycloakyl, C$_{2-6}$-alkenyl, C$_{2-6}$-alkinyl, C$_{3-6}$-cycloalkyl, C$_{3-6}$-cycloalkyl-C$_{1-2}$-alkyl, C$_{1-4}$-alkoxycarbonyl, C$_{1-4}$-alkylcarbonyl, C$_{3-6}$-cycloalkylcarbonyl, cyano, aryl, aryl-C$_{1-2}$-alkyl, hetaryl or hetaryl-C$_{1-2}$-alkyl, each of which is optionally substituted, and
B represents C$_{1-6}$-alkoxy, C$_{2-6}$-alkenyloxy, C$_{2-6}$-alkinyloxy, C$_{3-7}$-cycloalkyloxy, C$_{3-7}$-cycloalkyl-C$_{1-2}$-alkyloxy, aryloxy-, aryl-C$_{1-2}$-alkyloxy, hetaryloxy, hetaryl-C$_{1-2}$-alkyloxy, each of which is optionally substituted, or
represents the amino radicals —NR$^{12}$R$^{13}$, —NR$^{14}$—NR$^{12}$R$^{13}$ and —NR$^{15}$—OR$^{16}$, in which
R$^{12}$ and R$^{13}$ independently of one another represent hydrogen, straight-chain or branched C$_{1-6}$-alkyl, C$_{1-6}$-alkylcarbonyl, C$_{1-6}$-alkylsulphonyl, C$_{2-6}$-alkenyl, C$_{2-6}$-alkinyl, C$_{3-8}$-cycloalkyl, C$_{3-8}$-cycloalkyl-C$_{1-2}$-alkyl, aryl, arylcarbonyl, arylsulphonyl, aryl-C$_{1-2}$-alkyl, hetaryl, hetarylcarbonyl, hetarylsulphonyl or hetaryl-C$_{1-2}$-alkyl, each of which is optionally substituted, or
R$^{12}$ and R$^{13}$ together with the adjacent N atom represent a carbocyclic 5-, 6-, 7- or 8-membered ring system or a 7 to 10-membered bicyclic ring system, which can optionally also be interrupted by oxygen, sulphur, sulphoxyl, sulphonyl, carbonyl, —N—O, —N═, —NR$^{11}$— or by quaternized nitrogen and is optionally substituted, R$^{14}$ represents hydrogen, straight-chain or branched C$_{1-6}$-alkyl, C$_{3-6}$-cycloalkyl, each of which is optionally substituted,
R$^{15}$ and R$^{16}$ independently of one another denote hydrogen, straight-chain or branched C$_{1-6}$-alkyl, C$_{1-6}$-alkylcarbonyl, C$_{2-6}$-alkenyl, C$_{2-6}$-alkinyl or C$_{3-6}$-cycloalkyl, each of which is optionally substituted, and
R$^{15}$ and R$^{16}$ together with the adjacent N—O-group represent a carbocyclic 5-, 6- or 7-membered ring,
with the proviso in the case where in formula (Ia) R$^1$, R$^5$ and ═G═X together represent the following radicals:
R$^1$ represents hydrogen and methyl,
R$^5$ represents hydrogen,

represents carboxyl,
the radicals Q and B must fulfil the following condition:
Q represents radicals other than methyl,
B represents radicals other than —NH$_2$,
and with the proviso in the case where in formula (Ia) G$^2$ and ═G═X together represent the following radicals:

represents carboxyl,
G$^2$ represents tert-butyloxy, benzyloxy and 4-nitro-benzyloxy,
the radical B represents radicals other than tert-butyloxy, benzyloxy and 4-nitro-benzyloxy,
and their optical isomers and racemates.

3. Process for the preparation of the new didepsipeptides of the general formula (Ia) and their salts,

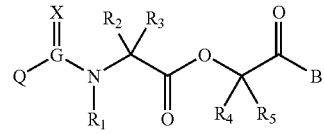

in which
the radicals R$^1$, R$^2$, R$^3$, R$^4$, R$^5$, G, Q, X and B have the meaning indicated under item 2,
characterized in that
a) N-terminal-substituted amino acids of the general formula (II)

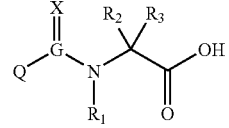

in which the radicals $R^1$, $R^2$, $R^3$, G, Q, and X have the meaning indicated under item 2, or their carboxyl-activated derivatives or their alkali metal salts, are reacted, if appropriate in the presence of a catalyst, if appropriate in the presence of an acid-binding agent and if appropriate in the presence of a diluent, with carboxylic acid derivatives of the general formula (III)

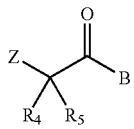
(III)

in which the radicals $R^4$, $R^5$ and B have the meaning indicated under item 2 and Z represents a suitable leaving group for example halogen such as bromine, chlorine fluorine, or hydroxyl, or b) N-terminal-deblocked didepsipeptides of the general formula (Ib)

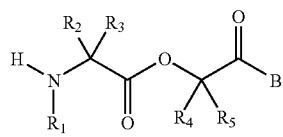
(Ib)

in which the radicals $R^1$, $R^2$, $R^3$, $R^4$, $R^5$ and B have the meaning indicated under item 2, are reacted, if appropriate in the presence of a catalyst, if appropriate in the presence of an acid-binding agent and if appropriate in the presence of a diluent, with compounds of the general formula (IV)

(IV)

in which the radicals G, Q, W and X have the meaning indicated under item 2 and W represents a suitable leaving group, for example halogen, alkoxy, alkylthio or aryloxy, or c) N-terminal-deblocked didepsipeptides of the general formula (Ib)

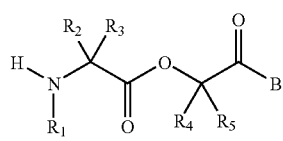
(Ib)

in which the radicals $R^1$, $R^2$, $R^3$, $R^4$, $R^5$ and B have the meaning indicated under item 2, are reacted, if appropriate in the presence of a catalyst, if appropriate in the presence of an acid-binding agent and if appropriate in the presence of a diluent, with compounds of the general formulae (V) or (VI)

(V)

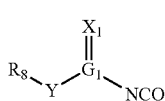
(VI)

in which the radicals $R^8$, $G^1$, X, $X^1$ and Y have the meaning indicated under item 2, or for the preparation of the depsipeptides of the general formula (Ia) and their salts in which the group

represents carboxyl and Y represents oxygen, d) N-terminal-deblocked didepsipeptides of the general formula (Ib)

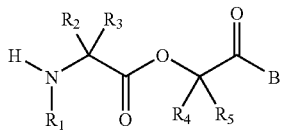
(Ib)

in which the radicals $R^1$, $R^2$, $R^3$, $R^4$, $R^5$ and B have the meaning indicated under item 2, are reacted in a first reaction step with carbon dioxide and an alkali metal carbonate of the formula (VII)

$M_2CO_3$ (vii)

in which

M represents a monovalent alkali metal cation, preferably lithium, sodium, potassium or caesium, in particular potassium or caesium, then in a second reaction step the resulting alkali metal salt of the formula (VIII)

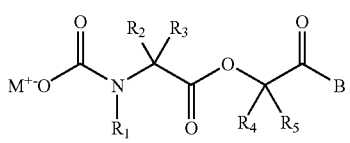
(viII)

in which
the radicals $R^1$, $R^2$, $R^3$, $R^4$, $R^5$ and B have the meaning indicated under item 2,
M represents a metal cation equivalent bound like a salt,
is reacted with alkylating agents of the formula (IX)

in which
$R^8$ has the meaning indicated under item 2 and
Hal represents a halogen such as fluorine, chlorine, bromine or iodine,
if appropriate in the presence of a diluent and if appropriate in the presence of a basic reaction auxiliary, or e) didepsipeptides of the general formula (Ic)

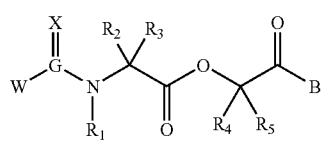

in which
the radicals $R^1$, $R^2$, $R^3$, $R^4$, $R^5$, G, W, X and B and have the meaning indicated under item 2 and 3b, are reacted, if appropriate in the presence of a catalyst, if appropriate in the presence of an acid-binding agent and if appropriate in the presence of a diluent, with compounds of the general formula (X)

in which
the radicals $R^8$ and Y have the meaning indicated above under item 2, or f) didepsipeptides of the general formula (Id)

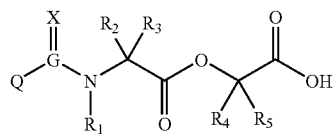

in which
the radicals $R^1$, $R^2$, $R^3$, $R^4$, $R^5$, G, Q, X and B have the meaning indicated under item 2, or their carboxyl-activated derivatives or their alkali metal salts are reacted, if appropriate in the presence of a catalyst, if appropriate in the presence of an acid-binding agent and if appropriate in the presence of a diluent, with compounds of the general formula (XI)

in which
the radical B has the meaning indicated above under item 2.

Formula (I) provides a general definition of the substituted didepsipeptides according to the invention and their salts.

The substituted didepsipeptides of the formula (I) according to the invention and their acid addition salts and metal salt complexes have very good endoparasiticidal, in particular anthelmintic, action and can preferably be employed in the field of veterinary medicine.

Optionally substituted alkyl on its own or as a constituent of a radical in the general formulae denotes straight-chain or branched alkyl preferably having 1 to 6, in particular 1 to 4, carbon atoms. Examples which may be mentioned are optionally substituted methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1-1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preferably mention may be made of methyl, ethyl, n-propyl, isopropyl, n-butyl, isobutyl, sec-butyl and tert-butyl.

Optionally substituted alkenyl on its own or as a constituent of a radical in the general formulae denotes straight-chain or branched alkenyl preferably having 1 to 6, in particular 1 to 4, carbon atoms. Examples which may be mentioned are substituted vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Preferably mention may be made of optionally substituted ethenyl, 2-propenyl, 2-butenyl or 1-methyl-2-propenyl.

Optionally substituted alkinyl on its own or as a constituent of a radical in the general formulae denotes straight-chain or branched alkinyl preferably having 1 to 6, in particular 1 to 4, carbon atoms. Examples which may be mentioned are substituted ethinyl, 2-propinyl, 2-butinyl, 3-butinyl, 1-methyl-2-propinyl, 2-pentinyl, 3-pentinyl, 4-pentinyl, 1-methyl-3-butinyl, 2-methyl-3-butinyl, 1-methyl-2-butinyl, 1,1-dimethyl-2-propinyl, 1-ethyl-2-propinyl, 2-hexinyl, 3-hexinyl, 4-hexinyl, 5-hexinyl, 1-methyl-2-pentinyl, 1-methyl-3-pentinyl, 1-methyl-4-pentinyl, 2-methyl-3-pentinyl, 2-methyl-4-pentinyl, 3-methyl-4-pentinyl, 4-methyl-2-pentinyl, 1,1-dimethyl-2-butinyl, 1,1-dimethyl-3-butinyl, 1,2-dimethyl-3-butinyl, 2,2-dimethyl-3-butinyl, 1-ethyl-3-butinyl, 2-ethyl-3-butinyl and 1-ethyl-1-methyl-2-propinyl.

Preferably mention may be made of optionally substituted ethinyl, 2-propinyl or 2-butinyl.

Optionally substituted cycloalkyl on its own or as a constituent of a radical in the general formulae denotes mono-, bi- and tricyclic cycloalkyl, preferably having 3 to 10, in particular having 3, 5 or 7, carbon atoms. Examples which may be mentioned are substituted cyclopropyl, cyclobutyl, cyclopentyl, cyclohexyl, cycloheptyl, cyclooctyl, bicyclo[2.2.1]heptyl, bicyclo[2.2.2]octyl and adamantyl.

Halogenoalkyl on its own or as a constituent of a radical in the general formulae contains 1 to 4, in particular 1 or 2, carbon atoms and preferably 1 to 9, in particular 1 to 5, identical or different halogen atoms preferably fluorine, chlorine and bromine, in particular fluorine and chlorine. Examples which may be mentioned are trifluoromethyl, trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl and pentafluoro-tert-butyl.

Optionally substituted alkoxy on its own or as a constituent of a radical in the general formulae denotes straight-chain or branched alkoxy preferably having 1 to 6, in particular 1 to 4, carbon atoms. Examples which may be mentioned are optionally substituted methoxy, ethoxy, n-propoxy, isopropoxy, n-butoxy, isobutoxy, sec-butoxy and tert-butoxy.

Optionally substituted halogenoalkoxy on its own or as a constituent of a radical in the general formulae denotes straight-chain or branched halogenoalkoxy preferably having 1 to 6, in particular 1 to 4, carbon atoms. Examples which may be mentioned are optionally substituted difluoromethoxy, trifluoromethoxy, trichloromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy and 2-chloro-1,1,2-trifluoroethoxy.

Optionally substituted alkylthio on its own or as a constituent of a radical in the general formulae denotes straight-chain or branched alkylthio preferably having 1 to 6, in particular 1 to 4, carbon atoms. Examples which may be mentioned are optionally substituted methylthio, ethylthio, n-propylthio, isopropylthio, n-butylthio, isobutylthio, sec-butylthio and tert-butylthio.

Optionally substituted halogenoalkylthio on its own or as a constituent of a radical in the general formulae denotes straight-chain or branched halogenoalkylthio preferably having 1 to 6, in particular 1 to 4, carbon atoms. Examples which may be mentioned are optionally substituted difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio and 2-chloro-1,1,2-trifluoroethylthio.

Optionally substituted alkylcarbonyl on its own or as a constituent of a radical in the general formulae denotes straight-chain or branched alkylcarbonyl having 1 to 6, in particular 1 to 4, carbon atoms. Examples which may be mentioned are optionally substituted methylcarbonyl, ethylcarbonyl, n-propylcarbonyl, isopropylcarbonyl, n-butylcarbonyl, isobutylcarbonyl, sec-butylcarbonyl and tert-butylcarbonyl.

Optionally substituted cycloalkylcarbonyl on its own or as a constituent of a radical in the general formulae denotes mono-, bi- and tricyclic cycloalkylcarbonyl, preferably having 3 to 10, in particular having 3, 5 or 7, carbon atoms. Examples which may be mentioned are optionally substituted cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptylcarbonyl, bicyclo[2.2.2]octylcarbonyl and adamantylcarbonyl.

Optionally substituted alkoxycarbonyl on its own or as a constituent of a radical in the general formulae denotes straight-chain or branched alkoxycarbonyl preferably having 1 to 6, in particular 1 to 4, carbon atoms. Examples which may be mentioned are optionally substituted methoxycarbonyl, ethoxycarbonyl, n-propoxycarbonyl, isopropoxycarbonyl, n-butoxycarbonyl, isobutoxycarbonyl, sec-butoxycarbonyl and tert-butoxycarbonyl.

Aryl is, for example, a mono-, bi- or polynuclear aromatic radical such as phenyl, naphthyl, tetrahydronaphthyl, indanyl, fluorenyl and the like, preferably phenyl or naphthyl.

Optionally substituted aryl in the general formulae denotes phenyl or naphthyl which is preferably optionally substituted, in particular phenyl.

Optionally substituted arylalkyl in the general formulae denotes arylalkyl which is preferably optionally substituted in the aryl moiety and/or alkyl, preferably having 6 or 10, in particular 8, carbon atoms in the aryl moiety (preferably phenyl or naphthyl, in particular phenyl) and preferably 1 to 4, in particular 1 or 2, carbon atoms in the alkyl moiety, where the alkyl moiety can be straight-chain or branched. Examples which may preferably be mentioned are optionally substituted benzyl and phenylethyl.

Optionally substituted hetaryl on its own or as a constituent of a radical in the general formulae denotes 5- to 7-membered rings preferably having 1 to 3, in particular 1 or 2, identical or different heteroatoms. Heteroatoms in the heteroaromatics are oxygen, sulphur or nitrogen. Examples which may preferably be mentioned are optionally substituted furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, piperidyl, pyrrolyl, pyridyl, piperazinyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl and 1,2,4-diazepinyl.

The optionally substituted radicals of the general formulae can carry one or more, preferably 1 to 3, in particular 1 or 2, identical or different substituents. Examples of substituents which may preferably be mentioned are:

alkyl preferably having 1 to 4, in particular 1 to 2, carbon atoms, such as methyl, ethyl, n-propyl, isopropyl, n-butyl, isobutyl, sec-butyl and tert-butyl; alkoxy preferably having 1 to 4, in particular 1 to 2 carbon atoms, such as methoxy, ethoxy, n-propoxy, isopropoxy, n-butoxy, isobutoxy, sec-butoxy and tert-butoxy; alkylthio such as methylthio, ethylthio, n-propylthio, isopropylthio, n-butylthio, isobutylthio, sec-butylthio and tert-butylthio; halogenoalkyl preferably having 1 to 4, in particular 1 to 2 carbon atoms and preferably 1 to 5, in particular 1 to 3, halogen atoms, where the halogen atoms are identical or different and, as halogen atoms, are preferably fluorine, chlorine or bromine, in particular fluorine or chlorine, such as difluoromethyl, trifluoromethyl, trichloromethyl; hydroxyl; halogen, preferably fluorine, chlorine, bromine and iodine, in particular fluorine and chlorine; cyano; nitro; amino; monoalkyl- and dialkylamino preferably having 1 to 4, in particular 1 or 2 carbon atoms per alkyl group, such as methylamino, methylethylamino, dimethyl-amino, n-propyl-amino, isopropylamino, methyl-n-butylamino; alkylcarbonyl radicals such as methylcarbonyl; alkoxycarbonyl preferably having 2 to 4, in particular 2 to 3, carbon atoms, such as methoxycarbonyl and ethoxycarbonyl; alkylsulphinyl having 1 to 4, in particular 1 to 2, carbon atoms; halogenosulphinyl having 1 to 4, in particular 1 to 2, carbon atoms and 1 to 5 halogen atoms, such as trifluoromethylsilphinyl; sulphonyl (—SO$_2$—OH); alkylsulphonyl preferably having 1 to 4, in particular 1 or 2, carbon atoms, such as methylsulphonyl and ethylsulphonyl; halogenoalkylsulphonyl having 1 to 4, in particular 1 to 2, carbon atoms and 1 to 5 halogen atoms, such as trifluoromethylsulphonyl, perfluoro-n-butylsulphonyl, perfluoroisobutylsulphonyl; arylsulphonyl preferably having 6 or 10 aryl carbon atoms, such as phenylsulphonyl; acyl, aryl, aryloxy, hetaryl, hetaryloxy, which for their part can carry one of the abovementioned substituents, and the formimino radical (—HC=N—O-alkyl).

Suitable cyclic amino groups are heteroaromatic or aliphatic ring systems having one or more nitrogen atoms as heteroatom, in which the heterocycles can be saturated or unsaturated, a ring system or several fused ring systems, and optionally contain further heteroatoms such as nitrogen, oxygen and sulphur etc. Additionally, cyclic amino groups can also denote a spiro ring or a bridged ring system. The number of atoms which form cyclic amino groups is not restricted, for example they consist in the case of a one-ring system of 3 to 8 atoms and in the case of a three-ring system of 7 to 11 atoms.

Examples of cyclic amino groups having saturated and unsaturated monocyclic groups having a nitrogen atom as heteroatom which may be mentioned are 1-azetidinyl, pyrrolidino, 2-pyrrolin-1-yl, 1-pyrrolyl, piperidino, 1,4-dihydropyridin-1-yl, 1,2,5,6-tetrahydropyridin-1-yl, homopiperidino; examples of cyclic amino groups having saturated and unsaturated monocyclic groups having two or more nitrogen atoms as heteroatoms which may be mentioned are 1-imidazolidinyl, 1-imidazolyl, 1-pyrazolyl, 1-triazolyl, 1-tetrazolyl, 1-piperazinyl, 1-homopiperazinyl, 1,2-dihydro-pyridazin-1-yl, 1,2-dihydropyrimidin-1-yl, perhydropyrimidin-1-yl and 1,4-diazacycloheptan-1-yl; examples of cyclic amino groups having saturated and unsaturated monocyclic groups having one to three nitrogen atoms and one to two sulphur atoms as heteroatoms which may be mentioned are thiazolidin-3-yl, isothiazolin-2-yl, thiomorpholino or dioxothiomorpholino; examples of cyclic amino groups having saturated and unsaturated fused cyclic groups which may be mentioned are indol-1-yl, 1,2-dihydrobenzimidazol-1-yl, perhydropyrrolo[1,2-a]pyrazin-2-yl; an example of cyclic amino groups having spirocyclic groups which may be mentioned is 2-azaspiro[4,5]decan-2-yl; an example of cyclic amino group-bridged heterocyclic groups which may be mentioned is 2-azabicyclo[2,2,1]heptan-7-yl.

Preferred compounds are those of the formula (Ia) and their salts

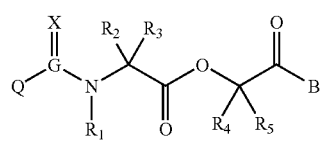

(Ia)

in which
R$^1$ represents hydrogen, straight-chain or branched C$_{1-6}$-alkyl, in particular methyl, ethyl, propyl, isopropyl, sec-butyl, tert-butyl, C$_{3-6}$-cycloalkyl, in particular cyclopropyl, cyclobutyl, cyclopentyl, cyclohexyl, aryl-C$_{1-2}$-alkyl, in particular phenylmethyl or hetaryl-C$_{1-2}$-alkyl, in particular pyridylmethyl and thiazolylmethyl, each of which is optionally substituted, and R$^1$ and R$^2$ together with the atoms to which they are bonded represent a 5- or 6-membered ring which can optionally be interrupted by sulphur and is optionally substituted by hydroxyl, R$^2$ represents hydrogen, straight-chain or branched alkyl having up to 6 carbon atoms, in particular methyl, ethyl, propyl, isopropyl, sec-butyl, tert-butyl, hydroxy-C$_{1-2}$-alkyl, in particular hydroxymethyl, 1-hydroxyethyl, C$_{1-4}$-alkanoyloxy-C$_{1-4}$-alkyl, in particular acetoxymethyl, 1-acetoxyethyl, C$_{1-4}$-alkoxy-C$_{1-4}$-alkyl, in particular methoxymethyl, 1-methoxyethyl, aryl-C$_{1-4}$-alkoxy-C$_{1-4}$-alkyl, in particular benzyloxymethyl, 1-benzyloxymethyl, mercapto-C$_{1-4}$-alkyl, in particular mercaptomethyl, C$_{1-4}$-alkylthio-C$_{1-4}$-alkyl, in particular methylsulphinylmethyl, C$_{1-4}$-alkylsulphonyl-C$_{1-4}$-alkyl, in particular methylsulphonylethyl, carboxy-C$_{1-4}$-alkyl, in particular carboxymethyl, carboxyethyl, C$_{1-4}$-alkoxycarbonyl-C$_{1-4}$-alkyl, in particular methoxycarbonylmethyl, ethoxycarbonylmethyl, aryl-C$_{1-4}$-alkoxycarbonyl-C$_{1-4}$-alkyl, in particular benzyloxycarbonylmethyl, carbamoyl-C$_{1-4}$-alkyl, in particular carbamoylmethyl, carbamoylethyl, amino-C$_{1-4}$-alkyl, in particular aminopropyl, aminobutyl, C$_{1-4}$-alkylamino-C$_{1-4}$-alkyl, in particular methylaminopropyl, methylaminobutyl, C$_{1-4}$-dialkylamino-C$_{1-4}$-alkyl, in particular dimethylaminopropyl, dimethylaminobutyl, guanido-C$_{1-4}$-alkyl, in particular guanidopropyl, C$_{1-4}$-alkoxycarbonylamino-C$_{1-4}$-alkyl, in particular tert-butylcarbonylaminopropyl, tert-butylcarbonylaminobutyl, alkenyl having up to 6 carbon atoms, in particular vinyl, 2-propenyl, 2-butenyl, 1-methyl-2-propenyl, C$_{3-6}$-cycloalkyl-C$_{1-2}$-alkyl, in particular cyclopropylmethyl, cyclobutylmethyl, cyclohexylmethyl, hetaryl-C$_{1-2}$-alkyl, in particular benzo-[b]thien-1-yl-methyl, benzo[b]-thien-3-yl, pyrid-2-yl-methyl, pyrid-3-yl-methyl, pyrid-4-yl-methyl, fur-2-yl-methyl, fur-3-yl-methyl, thien-2-yl-methyl, thien-3-yl-methyl, indol-3-yl-methyl, N-methyl-indol-3-yl-methyl, imidazol-4-yl-methyl, N-methylimidazol-4-yl-methyl, aryl-C$_{1-2}$-alkyl, in particular benzyl, each of which can optionally be substituted by radicals from the series consisting of halogen, in particular, fluorine, chlorine, bromine or iodine, hydroxyl, C$_{1-4}$-alkyl, in particular methyl or tert-butyl, C$_{1-4}$-halogenoalkyl, in particular trifluoromethylethyl, difluoromethyl or trichloromethyl, C$_{1-4}$-alkoxy, in particular methoxy, ethoxy or tert-butyloxy, C$_{1-4}$-halogenoalkoxy, in particular Trifluoromethoxy, difluoromethoxy, C$_{1-4}$-alkylthio, in particular methylthio, C$_{1-4}$-halogenoalkylthio, in particular trifluoromethylthio, C$_{1-2}$-alkylenedioxy, in particular methylenedioxy or ethylenedioxy, nitro, amino, C$_{1-4}$-alkylamino, in particular methylamino, C$_{1-4}$-di-alkylamino, in particular dimethylamino, C$_{3-6}$-cycloalkylamino, in particular pyrrolidino, piperidino, C$_{3-6}$-cycloalkylthioamino, in particular thiomorpholino and dioxothiomorpholino, C$_{3-6}$-cycloalkyldiamino, in particular N-methylpiperazino, and R$^3$ and R$^4$ represent hydrogen, R$^5$ represents hydrogen, straight-chain or branched alkyl having up to 6 carbon atoms, in particular methyl, ethyl, propyl, isopropyl, sec-butyl, tert-butyl, hydroxy-C$_{1-2}$-alkyl, in particular hydroxymethyl, 1-hydroxyethyl, C$_{1-4}$-alkanoyloxy-C$_{1-4}$-alkyl, in particular acetoxymethyl, 1-acetoxyethyl, C$_{1-4}$-alkoxy-C$_{1-4}$-alkyl, in particular methoxymethyl, 1-methoxyethyl, aryl-C$_{1-4}$-alkoxy-C$_{1-4}$-alkyl, in particular benzyloxymethyl, 1-benzyloxymethyl, mercapto-C$_{1-4}$-alkyl, in particular mercaptomethyl, C$_{1-4}$-alkylthio-C$_{1-4}$-alkyl, in particular methylsulphinylmethyl, C$_{1-4}$-alkylsulphonyl-C$_{1-4}$-alkyl, in particular methylsulphonylethyl, carboxy-C$_{1-4}$-alkyl, in particular carboxymethyl, carboxyethyl, C$_{1-4}$-alkoxycarbonyl-C$_{1-4}$-alkyl, in particular methoxycarbonylmethyl, ethoxycarbonylmethyl, aryl-C$_{1-4}$-alkoxycarbonyl-C$_{1-4}$-alkyl, in particular benzyloxycarbonylmethyl, carbamoyl-C$_{1-4}$-alkyl, in particular carbamoylmethyl, carbamoylethyl, amino-C$_{1-4}$-alkyl, in particular aminopropyl, aminobutyl, C$_{1-4}$-alkylamino-C$_{1-4}$-alkyl, in particular methylaminopropyl, methylaminobutyl, C$_{1-4}$-dialkylamino-C$_{1-4}$-alkyl, in particular dimethylaminopropyl, dimethylaminobutyl, guanido-$C_{1-4}$-alkyl, in particular guanidopropyl, $C_{1-4}$-alkoxycarbonylamino-$C_{1-4}$-alkyl, in particular tert-butylcarbonylaminopropyl, tert-butylcarbonylaminobutyl, alkenyl having up to 6 carbon atoms, in particular vinyl, 2-propenyl, 2-butenyl, 1-methyl-2-propenyl, $C_{3-6}$-cycloalkyl-$C_{1-2}$-alkyl, in particular cyclopropylmethyl, cyclobutylmethyl, cyclohexylmethyl, hetaryl-$C_{1-2}$-alkyl, in particular benzo-[b]thien-1-yl-methyl, benzo[b]-thien-3-yl, pyrid-2-yl-methyl, pyrid-3-yl-methyl, pyrid-4-yl-methyl, fur-2-yl-methyl, fur-3-yl-methyl, thien-2-yl-methyl, thien-3-yl-methyl, indol-3-yl-methyl, N-methyl-indol-3-yl-methyl, imidazol-4-yl-methyl, N-methylimidazol-4-yl-methyl, aryl-$C_{1-2}$-alkyl, in particular benzyl, each of which can optionally be substituted by radicals from the series consisting of halogen, in particular fluorine, chlorine, bromine or iodine, hydroxyl, $C_{1-4}$-alkyl, in particular methyl or tert-butyl, $C_{1-4}$-halogenoalkyl, in particular trifluoromethylethyl, difluoromethyl or trichloromethyl, $C_{1-4}$-alkoxy, in particular methoxy, ethoxy or tert-butyloxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, $C_{1-2}$-alkylenedioxy, in particular methylenedioxy or ethylenedioxy, nitro, amino, $C_{1-4}$-alkylamino, in particular methylamino, $C_{1-4}$-dialkylamino, in particular dimethylamino, $C_{3-6}$-cycloalkylamino, in particular pyrrolidino, piperidino, $C_{3-6}$-cycloalkylthioamino, in particular thiomorpholino and dioxothiomorpholino, $C_{3-6}$-cycloalkyldiamino, in particular N-methylpiperazino, and

represents carboxyl, thiocarboxyl, —CH=CH—$NO_2$, —C=CH—CN, —C=N—$R^6$, sulphoxyl, sulphonyl, —P(O)—$OR^7$ or P(S)—$OR^7$, $R^6$ represents hydrogen, hydroxyl, $C_{1-4}$-alkoxy, in particular methoxy, ethoxy, sec-butyloxy, $C_{1-4}$-alkylcarbonyl, in particular methylcarbonyl, ethylcarbonyl, $C_{1-4}$-halogenoalkylcarbonyl, in particular trifluoromethylcarbonyl, trichloromethylcarbonyl, $C_{1-4}$-alkylsulphonyl, in particular methylsulphonyl, ethylsulphonyl, propylsulphonyl, nitro or cyano, and $R^7$ represents hydrogen or $C_{1-4}$-alkyl, in particular methyl or ethyl, and Q represents straight-chain or branched $C_{1-4}$-alkyl, in particular methyl, ethyl, propyl, isopropyl, sec-butyl, tert-butyl, $C_{1-4}$-halogenoalkyl, in particular trifluoromethyl, trichloromethyl, chlorodifluoromethyl, dichlorofluoromethyl, 1-fluoroethyl, chloromethyl, bromomethyl, 1-fluoroethyl, 2,2,2-trifluoroethyl, 2,2,2-trichloroethyl, $C_{2-6}$-alkenyl, in particular vinyl, 2-propenyl, 1-methyl-2-propenyl and 2-butenyl, $C_{2-6}$-halogenoalkenyl, in particular difluorovinyl, dichlorovinyl, 2-chloro-2-propenyl, 2,3,3-trifluoro-2-propenyl, 2,3,3-trichloro-2-propenyl, 4,4-difluoro-3-butenyl, $C_{3-6}$-cycloalkyl, in particular cyclopropyl, cyclobutyl, cyclopentyl and cyclohexyl, hetaryl-$C_{1-2}$-alkyl, in particular pyridylmethyl and thiazolylmethyl, each of which can optionally be substituted by radicals from the series consisting of halogen, in particular fluorine, chlorine, bromine or iodine, hydroxyl, $C_{1-4}$-alkyl, in particular methyl or tert-butyl, $C_{1-4}$-halogenoalkyl, in particular trifluoromethyl, difluoromethyl or trichloromethyl, $C_{1-4}$-alkoxy, in particular methoxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, nitro, amino, $C_{1-4}$-alkylamino, in particular methylamino, $C_{1-4}$-dialkylamino, in particular dimethylamino, or optionally represents a radical from the group $G^2$ and $G^3$

in which

can denote carboxyl, thiocarboxyl or sulphonyl,

Y represents oxygen, sulphur or —$NR^9$, $R^8$ in the case where Y represents nitrogen [lacuna] a cyclic amino group linked via a nitrogen atom, in particular 1-azetidinyl, pyrrolidino, 2-pyrrolin-1-yl, 1-pyrrolyl, piperidino, 1,4-dihydropyridin-1-yl, 1-imidazolidiyl, 1-imidazolyl, 1-pyrazolyl, 1-triazolyl, 1-tetrazolyl, 1-piperazinyl, 1-homopiperazinyl, 1,2-dihydro-pyridazin-1-yl, 1,2-dihydropyrimidin-1-yl, perhydropyrimidin-1-yl, 1,4-diazacyclo-heptan-1-yl, thiazolidin-3-yl, isothiazolin-2-yl, morpholino, thiomorpholino, dioxothiomorpholino, each of which is optionally substituted by radicals from the series consisting of halogen, in particular fluorine, chlorine, bromine or iodine, $C_{1-4}$-alkyl, in particular methyl, hydoxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, $R^8$ and $R^9$ independently of one another represent hydrogen, straight-chain or branched $C_{1-4}$-alkyl, in particular methyl, ethyl, propyl, isopropyl, sec-butyl, tert-butyl, $C_{2-4}$-alkenyl, in particular vinyl, 2-propenyl, 1-methyl-2-propenyl and 2-butenyl, $C_{2-4}$-alkinyl, in particular ethinyl, 2-propinyl and 2-butinyl, $C_{3-6}$-cycloalkyl, in particular cyclopropyl, cyclobutyl, cyclopentyl and cyclohexyl, $C_{3-6}$-cycloalkyl-$C_{1-2}$-alkyl, in particular cyclopropylmethyl, cyclobutylmethyl, cyclopentylmethyl and cyclohexylmethyl, hetaryl, in particular pyridyl and thiazolyl, hetaryl-$C_{1-2}$-alkyl, in particular pyridylmethyl and thiazolylmethyl, each of which can optionally be substituted by radicals from the series consisting of halogen, in particular fluorine, chlorine, bromine or iodine, $C_{1-4}$-alkyl, in particular methyl, hydoxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, or $R^8$ and $R^9$ together with the adjacent N atom represent a carbocyclic 5-, 6- or 7-membered ring system or a 7 to 10-membered bicyclic ring system which can optionally also be interrupted by oxygen, sulphur, sulphoxyl, sulphonyl, carbonyl, —N—O, —N=, —$NR^{11}$— or by quaternized nitrogen and is optionally substituted by $C_{1-4}$-alkyl, in particular methyl, hydoxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, halogen, in particular fluorine, chlorine, bromine or iodine, $R^{10}$ represents hydrogen or $C_{1-4}$-alkyl, in particular methyl, ethyl, propyl, isopropyl, sec-butyl, tert-butyl, and $R^{11}$ represents hydrogen, straight-chain or branched $C_{1-6}$-alkyl, in particular methyl, ethyl, propyl, isopropyl, sec-butyl, tert-butyl, $C_{2-6}$-alkenyl, in particular vinyl, 2-propenyl, 1-methyl-2-propenyl and 2-butenyl, $C_{2-6}$-alkinyl, in particular ethinyl, 2-propinyl and 2-butinyl, $C_{3-6}$-cycloalkyl, in particular cyclopropyl, cyclobutyl, cyclopentyl and cyclohexyl, $C_{3-6}$-cycloalkyl-$C_{1-2}$-alkyl, in particular cyclopropylmethyl, cyclobutylmethyl, cyclopentylmethyl and cyclohexylmethyl, $C_{1-4}$-alkylcarbonyl, in particular methylcarbonyl, ethylcarbonyl, n-propylcarbonyl, isopropylcarbonyl, n-butylcarbonyl, isobutylcarbonyl, sec-butylcarbonyl, tert-butylcarbonyl, $C_{3-6}$-cycloalkylcarbonyl, in particular cyclopropylcarbonyl, cyclobutylcarbonyl, cyclopentylcarbonyl and cyclohexylcarbonyl, $C_{1-4}$-alkoxycarbonyl, in particular methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, hydoxy-$C_{1-4}$-alkyl, in particular hydroxymethyl, hydroxyethyl, hydroxyethylsulphonylethyl, $C_{1-4}$-alkylamino, in particular methylamino, ethylamino, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, dimethylaminopropyl, $C_{3-7}$-cycloalkylamino-$C_{1-4}$-alkyl, in particular N-pyrrolidinoethyl, N-morpholinoethyl, N-piperidinoethyl, N-thiomorpholinoethyl, $N^1$-($N^4$-methylpiperazino)ethyl, $C_{3-6}$-cycloalkylaminocarbonyl-$C_{1-2}$-alkyl, in particular N-morpholinocarbonylmethyl, cyano, aryl, in particular phenyl, aryl-$C_{1-2}$-alkyl, in particular phenylmethyl, hetaryl, in particular pyridyl or thiazolyl, hetaryl-$C_{1-2}$-alkyl, in particular pyridylmethyl and thiazolylmethyl, each of which can optionally be substituted by radicals from the series consisting of halogen, in particular fluorine, chlorine, bromine or iodine, $C_{1-4}$-alkyl, in particular methyl, $C_{1-4}$-halogenoalkyl, in particular trifluoromethyl, trichloromethyl, amino, hydroxyl, $C_{1-4}$-alkoxy, in particular methoxy, $C_{1-2}$-alkylenedioxy, in particular methylenedioxy or ethylenedioxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, $C_{1-4}$-alkylsulphonyl in particular methylsulphonyl, $C_{1-4}$-alkylamino, in particular methylamino, di-$C_{1-4}$-alkylamino, in particular dimethylamino, $C_{1-4}$-alkylcarbonyl, in particular methylcarbonyl, $C_{1-4}$-alkoxycarbonyl, in particular methoxycarbonyl B represents straight-chain or branched $C_{1-6}$-alkoxy, in particular methoxy, ethoxy, n-propoxy, isopropoxy, n-butoxy, isobutoxy, sec-butoxy and tert-butoxy, $C_{2-6}$-alkenyloxy, vinyloxy, 2-propenyloxy, 2-butenyloxy, 3-butenyloxy, 1-methyl-2-propenyloxy, 2-methyl-2-propenyloxy, 2-pentenyloxy, 1-methyl-2-butenyloxy, 2-methyl-2-butenyloxy, 3-methyl-2-butenyloxy, 1-methyl-3-butenyloxy, 1,1-dimethyl-2-propenyloxy, 1,2-dimethyl-2-propenyloxy, 1-ethyl-2-propenyloxy, 2-hexenyloxy, 1,1-dimethyl-2-butenyloxy, 1,2-dimethyl-2-butenyloxy, 1-ethyl-2-butenyloxy, $C_{2-6}$-alkinyloxy, in particular ethinyloxy, 2-propinyloxy, 2-butinyloxy, 3-butinyloxy, 1-methyl-2-propinyloxy, 2-pentinyloxy, 1-methyl-3-butinyl, 2-methyl-3-butinyloxy, 1,1-dimethyl-2-propinyloxy, 1-ethyl-2-propinyloxy and 1-methyl-2-pentinyloxy, $C_{3-8}$-cycloalkyloxy, in particular cyclopropyloxy, cyclobutyloxy, cyclopentyloxy, cyclohexyloxy, cycloheptyloxy, $C_{3-7}$-cycloalkyl-$C_{1-2}$-alkyloxy, in particular cyclopropylmethoxy, cyclobutylmethoxy, cyclopentylmethoxy, cyclohexylmethoxy, cycloheptylmethoxy, aryloxy-, in particular phenoxy, aryl-$C_{1-2}$-alkyloxy, in particular benzyloxy, hetaryloxy, in particular pyridyloxy, hetaryl-$C_{1-2}$-alkyl-oxy, in particular pyridylmethyl and thiazolylmethyl, each of which can optionally be substituted by radicals from the series consisting of halogen, in particular fluorine, chlorine, bromine or iodine, $C_{1-4}$-alkyl, in particular methyl, $C_{1-4}$-halogenoalkyl, in particular trifluoromethyl, trichloromethyl, amino, hydroxyl, $C_{1-4}$-alkoxy, in particular methoxy, $C_{1-2}$-alkylenedioxy, in particular methylenedioxy or ethylenedioxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, $C_{1-4}$-alkylsulphonyl in particular methylsulphonyl, $C_{1-4}$-alkylamino, in particular methylamino, di-$C_{1-4}$-alkylamino, in particular dimethylamino, $C_{3-6}$-cycloalkylamino, in particular pyrrolidino, piperidino, $C_{3-6}$cycloalkyloxamino, in particular morpholino, $C_{3-6}$-cycloalkylthioamino, in particular thiomorpholino and dioxothiomorpholino, $C_{3-6}$-cycloalkyldiamino, in particular N-methylpiperazino, $C_{1-4}$-alkylcarbonyl, in particular methylcarbonyl, $C_{1-4}$-alkoxycarbonyl, in particular methoxycarbonyl, or represents the amino radicals —$NR^{12}R^{13}$, —$NR^{14}$—$NR^{12}R^{13}$ and —$NR^{15}$—$OR^{16}$, in which $R^{12}$ and $R^{13}$ independently of one another represent hydrogen, straight-chain or branched $C_{1-6}$-alkyl, in particular methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, $C_{1-6}$-alkylcarbonyl, in particular methylcarbonyl, ethylcarbonyl, n-propylcarbonyl, isopropylcarbonyl, n-butylcarbonyl, isobutylcarbonyl, sec-butylcarbonyl, tert-butylcarbonyl, pentylcarbonyl, 1-methylbutylcarbonyl, 2-methylbutylcarbonyl, $C_{1-6}$-alkylsulphonyl, in particular methylsulphonyl, ethylsulphonyl, n-propylsulphonyl, isopropylsulphonyl, n-butylsulphonyl, isobutylsulphonyl, sec-butylsulphonyl, $C_{2-6}$-alkenyl, in particular vinyl, 2-propenyl, 2-butenyl, 3-butenyl, 1-methyl-2-propenyl, 2-pentenyl, 3-pentenyl, 1-methyl-2-butenyl, 2-methyl-2-butenyl, 3-methyl-2-butenyl, 1,1-dimethyl-2-propenyl, 1,2-dimethyl-2-propenyl, 1-ethyl-2-propenyl, 2-hexenyl, 1,2-dimethyl-3-butenyl, 2,3-dimethyl-2-butenyl, 1-ethyl-2-butenyl, 1-ethyl-3-butenyl, 2-ethyl-2-butenyl, 2-ethyl-3-butenyl, $C_{2-6}$-alkinyl, in particular 2-propinyl, 2-butinyl, 3-butinyl, $C_{3-8}$-cycloalkyl, in particular cyclopropyl, cyclobutyl, cyclopentyl, cyclohexyl, cycloheptyl, cyclooctyl, $C_{3-8}$-cycloalkyl-$C_{1-2}$-alkyl, in particular cyclopropylmethyl, cyclobutylmethyl, cyclopentylmethyl, cyclohexylmethyl, cycloheptylmethyl, hydoxy-$C_{1-4}$-alkyl, in particular hydroxymethyl, hydroxyethyl, hydroxyethylsulphonylethyl, $C_{1-4}$-alkylamino, in particular methylamino, ethylamino, $C_{1-4}$-monoalkylamino-$C_{1-4}$-alkyl, in particular methylaminomethyl, methylaminoethyl, methylaminopropyl, $C_{1-4}$-dialkylamino-$C_{1-4}$-alkyl, in particular dimethylaminomethyl, dimethylaminoethyl, dimethylaminopropyl, $C_{3-7}$-cycloalkylamino-$C_{1-4}$-alkyl, in particular N-pyrrolidinoethyl, N-morpholinoethyl, N-piperidinoethyl, N-thiomorpholinoethyl, $N^1$-($N^4$-methyl-piperazino)-ethyl, $C_{3-6}$cycloalkylaminocarbonyl-$C_{1-2}$-alkyl, in particular N-morpholinocarbonylmethyl, aryl, in particular phenyl, aryl-$C_{1-2}$-alkyl, in particular benzyl and phenethyl, hetaryl, in particular pyridyl, thiazolyl, hetaryl-$C_{1-6}$-alkyl, in particular pyridylmethyl, thiazolylmethyl, each of which is optionally substituted by radicals from the series consisting of halogen, in particular fluorine, chlorine, bromine or iodine, hydroxyl, $C_{1-4}$-alkyl, in particular methyl or tert-butyl, $C_{1-4}$-alkoxy, in particular methoxy, ethoxy or tert-butyloxy, nitro, amino, $C_{1-4}$-alkylamino, in particular methylamino, $C_{1-4}$-dialkylamino, in particular dimethylamino, $C_{3-6}$-cycloalkylamino, in particular piperidino and morpholine or $R^{12}$ and $R^{13}$ together with the adjacent N atom represent a carbocyclic 5-, 6-, 7- or 8-membered ring system or a 7 to 10-membered bicyclic ring system which can optionally also be interrupted by oxygen, sulphur, sulphoxyl, sulphonyl, carbonyl, —N—O—, —N═, —NR$^{11}$— or by quaternized nitrogen and is optionally substituted by aryl, in particular phenyl, $C_{1-4}$-alkyl, in particular methyl, hydoxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, $C_{3-6}$-cycloalkylamino, in particular pyrrolidino, piperidino or morpholino, amino, hydroxyl, cyano, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, halogen, in particular fluorine, chlorine, bromine or iodine, or a radical from the groups $G^4$, $G^5$, $G^6$, $G^7$ and $G^8$

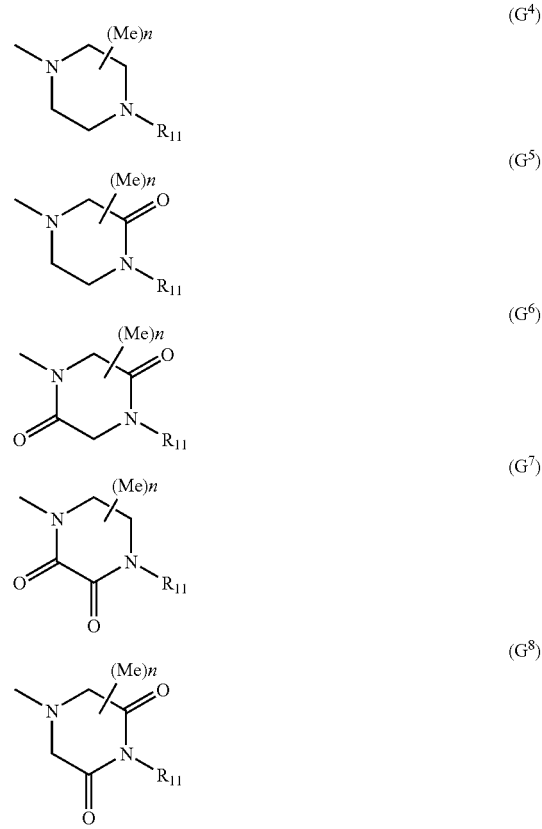

in which n can denote the numbers 0, 1, 2, 3 or 4, $R^{14}$ represents hydrogen, straight-chain or branched $C_{1-6}$-alkyl, methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, $C_{3-6}$-cycloalkyl, in particular cyclopropyl, cyclobutyl, cyclopentyl, cyclohexyl, each of which is optionally substituted, $R^{15}$ and $R^{16}$ independently of one another represent hydrogen, straight-chain or branched $C_{1-6}$-alkyl, in particular methyl, ethyl, n-propyl, iso-propyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, $C_{1-6}$-alkylcarbonyl, in particular methylcarbonyl, ethylcarbonyl, n-propylcarbonyl, isopropylcarbonyl, n-butylcarbonyl, isobutylcarbonyl, sec-butylcarbonyl, tert-butylcarbonyl, pentylcarbonyl, 1-methylbutylcarbonyl, 2-methylbutylcarbonyl, $C_{2-6}$-alkenyl, in particular vinyl, 2-propenyl, 2-butenyl, 3-butenyl, 1-methyl-2-propenyl, 2-pentenyl, 3-pentenyl, 1-methyl-2-butenyl, 2-methyl-2-butenyl, 3-methyl-2-butenyl, 1,1-dimethyl-2-propenyl, 1,2-dimethyl-2-propenyl, 1-ethyl-2- propenyl, 2-hexenyl, 1,2-dimethyl-3-butenyl, 2,3-dimethyl-2-butenyl, 1-ethyl-2-butenyl, 1-ethyl-3-butenyl, 2-ethyl-2-butenyl, 2-ethyl-3-butenyl, $C_{2-6}$-alkinyl, in particular 2-propinyl, 2-butinyl, 3-butinyl, $C_{3-6}$-cycloalkyl, in particular cyclopropyl, cyclobutyl, cyclopentyl, cyclohexyl, each of which is optionally substituted, $R^{15}$ and $R^{16}$ together with the adjacent N—O-group represent a carbocyclic 5-, 6- or 7-membered ring, with the proviso in the case where
$R^1$ represents hydrogen and methyl, and
$R^5$ represents hydrogen and

represents carboxyl,
Q represents radicals other than methyl,
B represents radicals other than —$NH_2$, and
with the further proviso in the case where

represents carboxyl, and
$G^2$ represents tert-butyloxy, benzyloxy and 4-nitro-benzyloxy,
B represents radicals other than tert-butyloxy, benzyloxy and 4-nitro-benzyloxy,
and its optical isomers and racemates.

Particularly preferred compounds are those of the formula (Ia) and their salts

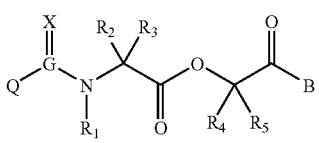

(Ia)

in which
$R^1$ represents hydrogen, straight-chain or branched $C_{1-4}$-alkyl, in particular methyl, ethyl, $C_{3-6}$-cycloalkyl, in particular cyclopropyl,
$R^2$ represents hydrogen, straight-chain or branched $C_{1-4}$-alkyl in particular methyl, ethyl, propyl, isopropyl, sec-butyl,
$R^3$ and $R^4$ represent hydrogen,
$R^5$ represents hydrogen, straight-chain or branched $C_{1-4}$-alkyl, in particular methyl, ethyl, propyl, isopropyl, sec-butyl, hetaryl-$C_{1-2}$-alkyl, in particular pyrid-2-yl-methyl, pyrid-3-yl-methyl, pyrid-4-yl-methyl, thien-2-yl-methyl, thien-3-yl-methyl, aryl-$C_{1-2}$-alkyl, in particular benzyl, each of which can optionally be substituted by radicals from the series consisting of halogen, in particular fluorine, chlorine, bromine or iodine, hydroxyl, $C_{1-4}$-alkyl, in particular methyl, or tert-butyl, $C_{1-4}$-alkoxy, in particular methoxy, ethoxy or tert-butyloxy, $C_{1-2}$-alkylenedioxy, in particular methylenedioxy or ethylenedioxy, nitro, amino, $C_{1-4}$-alkylamino, in particular methylamino, $C_{1-4}$-dialkylamino, in particular dimethylamino, $C_{3-6}$-cycloalkylamino, in particular pyrrolidino, piperidino, $C_{3-6}$-cycloalkylthioamino, in particular thiomorpholino and dioxothiomorpholino, $C_{3-6}$-cycloalkyldiamino, in particular N-methyl-piperazino, and

represents carboxyl, —CH=CH—$NO_2$, —C=CH—CN, —C=N—$R^6$ or sulphonyl,
$R^6$ represents $C_{1-4}$-halogenoalkylcarbonyl, in particular trifluoromethylcarbonyl, trichloromethylcarbonyl, alkyl-$C_{1-4}$-sulphonyl, in particular methylsulphonyl, ethylsulphonyl, nitro or cyano, and
Q represents a radical from the group $G^2$ and $G^3$

(G²)

(G³)

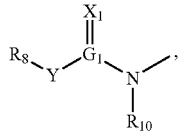

in which

can denote carboxyl or sulphonyl,
Y represents oxygen or —$NR^9$,
$R^8$ in the case where Y represents nitrogen denotes a cyclic amino group linked via a nitrogen atom, in particular pyrrolidino, 2-pyrrolin-1-yl, 1-pyrrolyl, piperidino, 1,4-dihydropyridin-1-yl, 1-piperazinyl, 1-homopiperazinyl, morpholino, thiomorpholino, dioxothiomorpholino, each of which can optionally be substituted by radicals from the series consisting of halogen, in particular fluorine, chlorine, bromine or iodine, $C_{1-4}$-alkyl, in particular methyl, hydoxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl,
$R^8$ and $R^9$ independently of one another represent straight-chain or branched $C_{1-4}$-alkyl, in particular methyl, ethyl, propyl, isopropyl, sec-butyl, $C_{2-4}$-alkenyl, in particular vinyl, 2-propenyl, 1-methyl-2-propenyl, $C_{2-4}$-alkinyl, in particular ethinyl, 2-propinyl, $C_{3-6}$-cycloalkyl, in particular cyclopropyl, hetaryl-$C_{1-2}$-alkyl, in particular pyridylmethyl and thiazolylmethyl, each of which can optionally be substituted by radicals from the series consisting of halogen, in particular fluorine, chlorine, bromine or iodine, $C_{1-4}$-alkyl, in particular methyl, hydoxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, or $R^8$ and $R^9$ together with the adjacent N atom represent a carbocyclic 5-, 6- or 7-membered ring system, which can optionally also be interrupted by oxygen, sulphur, sulphoxyl, carbonyl, —N═, —$NR^{11}$— or by quaternized nitrogen and is optionally substituted by $C_{1-4}$-alkyl, in particular methyl, hydoxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, halogen, in particular fluorine, chlorine, bromine or iodine, $R^{10}$ represents hydrogen or $C_{1-4}$-alkyl, in particular methyl, and $R^{11}$ represents hydrogen, straight-chain or branched $C_{1-6}$-alkyl, in particular methyl, ethyl, $C_{2-6}$-alkenyl, in particular vinyl, $C_{3-6}$-cycloalkyl, in particular cyclopropyl, $C_{1-4}$-alkylcarbonyl, in particular methylcarbonyl, $C_{3-6}$-cycloalkylcarbonyl, in particular cyclopropylcarbonyl, $C_{1-4}$-alkoxycarbonyl, in particular methoxycarbonyl, ethoxycarbonyl, tert-butoxycarbonyl, hydroxy-$C_{1-4}$-alkyl, in particular hydroxyethyl, hydroxysulphonylethyl, $C_{1-4}$-alkylamino, in particular ethylamino, $C_{1-4}$-monoalkylamino-$C_{1-4}$-alkyl, in particular methylaminoethyl, $C_{1-4}$-dialkylamino-$C_{1-4}$-alkyl, in particular dimethylaminoethyl, $C_{3-7}$-cycloalkylamino-$C_{1-4}$-alkyl, in particular N-morpholinoethyl, N-piperidinoethyl, $C_{3-6}$-cycloalkylaminocarbonyl-$C_{1-2}$-alkyl, in particular N-morpholinocarbonylmethyl, cyano, aryl, in particular phenyl, aryl-$C_{1-2}$-alkyl, in particular phenylmethyl, hetaryl, in particular pyridyl or thiazolyl, hetaryl-$C_{1-2}$-alkyl, in particular pyridylmethyl and thiazolylmethyl, each of which can optionally be substituted by radicals from the series consisting of halogen, in particular fluorine, chlorine, bromine or iodine, $C_{1-4}$-alkyl, methyl, $C_{1-4}$-halogenoalkyl, in particular trifluoromethyl, trichloromethyl, amino, hydroxyl, $C_{1-4}$-alkoxy, in particular methoxy, $C_{1-2}$-alkylenedioxy, in particular methylenedioxy or ethylenedioxy, $C_{1-4}$-halogenoalkoxy, in particular trifluoromethoxy, difluoromethoxy, $C_{1-4}$-alkylthio, in particular methylthio, $C_{1-4}$-halogenoalkylthio, in particular trifluoromethylthio, $C_{1-4}$-alkylsulphonyl in particular methylsulphonyl, $C_{1-4}$-alkylamino, in particular methylamino, di-$C_{1-4}$-alkylamino, in particular dimethylamino, $C_{1-4}$-alkylcarbonyl, in particular methylcarbonyl, $C_{1-4}$-alkoxycarbonyl, in particular methoxycarbonyl, B represents straight-chain or branched $C_{1-6}$-alkoxy, in particular methoxy, ethoxy, n-propoxy, isopropoxy, n-butoxy, isobutoxy, sec-butoxy and tert-butoxy, $C_{2-6}$-alkenyloxy, vinyloxy, 2-propenyloxy, 1,1-dimethyl-2-propenyloxy, 1,2-dimethyl-2-propenyloxy, 1-ethyl-2-propenyloxy, $C_{2-6}$-alkinyloxy, in particular 2-propinyloxy, 1-methyl-2-propinyloxy, 1,1-dimethyl-2-propinyloxy, $C_{3-8}$-cycloalkyloxy, in particular cyclopropyloxy, cyclohexyloxy, $C_{3-7}$-cycloalkyl-$C_{1-2}$-alkyloxy, in particular cyclopropylmethoxy, cyclohexylmethoxy, aryloxy-, in particular phenoxy, aryl-$C_{1-2}$-alkyloxy, in particular benzyloxy, hetaryloxy, in particular pyridyloxy, hetaryl-$C_{1-2}$-alkyloxy, in particular pyridylmethyl and thiazolylmethyl, each of which can be optionally substituted by radicals from the series consisting of halogen, in particular fluorine, chlorine, bromine or iodine, hydroxyl, $C_{1-4}$-alkyl, in particular methyl, $C_{1-4}$-halogenoalkyl, in particular trifluoromethyl, Trichloromethyl, amino, hydroxyl, $C_{1-4}$-alkoxy, in particular methoxy, $C_{1-2}$-alkylenedioxy, in particular methylenedioxy or ethylenedioxy, $C_{1-4}$-alkylamino, in particular methylamino, $C_{1-4}$-dialkylamino, in particular dimethylamino, $C_{3-6}$-cycloalkylamino, in particular pyrrolidino, piperidino, $C_{3-6}$-cycloalkylthioamino, in particular thiomorpholino and dioxothiomorpholino, $C_{3-6}$-cycloalkyldiamino, in particular N-methylpiperazino, or represents the amino radicals —$NR^{12}R^{13}$, —$NR^{14}$—$NR^{12}R^{13}$ and —$NR^{15}$—$OR^{16}$, in which $R^{12}$ and $R^{13}$ independently of one another represent hydrogen, straight-chain or branched $C_{1-6}$-alkyl, in particular methyl, ethyl, n-propyl, isopropyl, n-butyl, isobutyl, sec-butyl, tert-butyl, 1-methylbutyl, 2,2-dimethylpropyl, $C_{1-6}$-alkylcarbonyl, in particular methylcarbonyl, sec-butylcarbonyl, $C_{1-6}$-alkylsulphonyl, in particular methylsulphonyl, ethylsulphonyl, $C_{2-6}$-alkenyl, in particular vinyl, 2-propenyl, 1,2-dimethyl-2-propenyl, 2,3-dimethyl-2-butenyl, 1-ethyl-2-butenyl, $C_{2-6}$-alkinyl, in particular 2-propinyl, 2-butinyl, $C_{3-8}$-cycloalkyl, in particular cyclopropyl, cyclohexyl, $C_{3-8}$-cycloalkyl-$C_{1-2}$-alkyl, in particular cyclopropylmethyl, cyclobutylmethyl, hydoxy-$C_{1-4}$-alkyl, in particular hydroxymethyl, hydroxyethyl, hydroxyethylsulphonylethyl, $C_{1-4}$-alkylamino, in particular methylamino, ethylamino, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminomethyl, dimethylaminoethyl, dimethylaminopropyl, $C_{3-7}$-cycloalkylamino-$C_{1-4}$-alkyl, in particular N-pyrrolidinoethyl, N-morpholinoethyl, N-piperidinoethyl, N-thiomorpholino-ethyl, $N^1$-($N^4$-methylpiperazino)-ethyl, $C_{3-6}$-cycloalkylaminocarbonyl-$C_{1-2}$-alkyl, in particular N-morpholinocarbonylmethyl, aryl, in particular phenyl, aryl-$C_{1-2}$-alkyl, in particular benzyl, hetaryl-$C_{1-6}$-alkyl, in particular pyridylmethyl, thiazolylmethyl, each of which is optionally substituted by radicals from the series consisting of halogen, in particular fluorine, chlorine, bromine or iodine, hydroxyl, $C_{1-4}$-alkyl, in particular methyl or tert-butyl, $C_{1-4}$-alkoxy, in particular methoxy, ethoxy or tert-butyloxy, nitro, amino, $C_{1-4}$-alkylamino, in particular methylamino, $C_{1-4}$-dialkylamino, in particular dimethylamino, or $R^{12}$ and $R^{13}$ together with the adjacent N atom represent a carbocyclic 5-, 6-, 7- or 8-membered ring system which can optionally also be interrupted by oxygen, sulphur, sulphonyl, carbonyl, —N═, —$NR^{11}$— or by quaternized nitrogen and is optionally substituted by $C_{1-4}$-alkyl, in particular methyl, hydoxy-$C_{1-4}$-alkyl, in particular hydroxymethyl, amino-$C_{1-4}$-alkyl, in particular aminomethyl, aminoethyl, $C_{1-4}$-monoalkylamino-$C_{1-4}$-alkyl, in particular methylaminomethyl, methylaminoethyl, $C_{1-4}$-dialkylamino-$C_{1-4}$-alkyl, in particular dimethylaminoethyl, $C_{3-6}$-cycloalkylamino, in particular pyrrolidino, piperidino or morpholino, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, or a radical from the groups $G^4$, $G^5$, $G^6$, $G^7$ and $G^8$

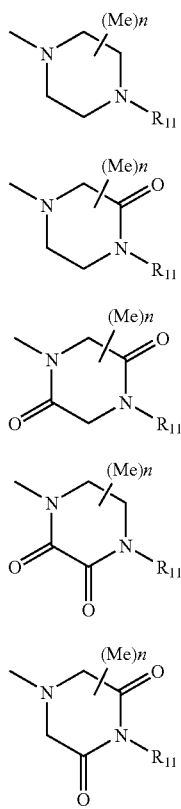

in which n can denote the numbers 0, 1, 2, or 3, $R^{14}$ represents hydrogen, straight-chain or branched $C_{1-6}$-alkyl, in particular methyl, ethyl, sec-butyl, $C_{3-6}$-cycloalkyl, in particular cyclopropyl, $R^{15}$ and $R^{16}$ independently of one another represent hydrogen, straight-chain or branched $C_{1-6}$-alkyl, in particular methyl, ethyl, sec-butyl, $C_{1-6}$-alkylcarbonyl, in particular methylcarbonyl, sec-butylcarbonyl, $C_{2-6}$-alkenyl, in particular 2-propenyl, 1-methyl-2-propenyl, 1,1-dimethyl-2-propenyl, $C_{2-6}$-alkinyl, in particular 2-propinyl, $C_{3-6}$-cycloalkyl, in particular cyclopropyl, $R^{15}$ and $R^{16}$ together with the adjacent N—O-group represent a carbocyclic 5-, 6- or 7-membered ring, with the proviso in the case where $R^1$ represents hydrogen and methyl, and $R^5$ represents hydrogen and

represents carboxyl,

Q represents radicals other than methyl,

B represents radicals other than —$NH_2$, and with the further proviso in the case where

represents carboxyl, and $G^2$ represents tert-butyloxy, benzyloxy and 4-nitro-benzyloxy, B represents radicals other than tert-butyloxy, benzyloxy and 4-nitro-benzyloxy, and its optical isomers and racemates.

Very particularly preferred compounds are those of the formula (Ia) and their salts

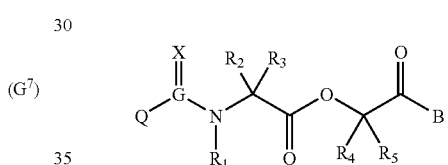

in which $R^1$ represents straight-chain or branched $C_{1-4}$-alkyl, in particular methyl, $R^2$ represents straight-chain or branched $C_{1-4}$-alkyl, in particular methyl or ethyl, $R^3$ and $R^4$ represent hydrogen, $R^5$ represents hydrogen, straight-chain or branched $C_{1-4}$-alkyl, in particular methyl or ethyl,

represents carboxyl or sulfonyl,

Q represents a radical from the group $G^2$ and $G^3$

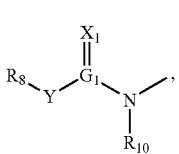

in which

can denote carboxyl or sulphonyl,

Y represents oxygen or —NR$^9$, $R^8$ in the case where Y represents nitrogen, denotes a cyclic amino group linked via a nitrogen atom, in particular pyrrolidino, 2-pyrrolin-1-yl, 1-pyrrolyl, piperidino, 1-piperazinyl, morpholino, thiomorpholino, dioxothiomorpholino, $R^8$ and $R^9$ independently of one another represent straight-chain or branched $C_{1-4}$-alkyl, in particular methyl, ethyl, propyl, isopropyl, sec-butyl, $C_{2-4}$-alkenyl, in particular vinyl, 2-propenyl, 1-methyl-2-propenyl and $C_{2-4}$-alkinyl, in particular ethinyl, 2-propinyl, $C_{3-6}$-cycloalkyl, in particular cyclopropyl, hetaryl-$C_{1-2}$-alkyl, in particular 2-chloro-pyrid-5-yl-methyl and chloro-thiazol-5-yl-methyl, or $R^8$ and $R^9$ together with the adjacent N atom represent a carbocyclic 5-, 6- or 7-membered ring system which can optionally also be interrupted by oxygen, sulphur, sulphonyl, carbonyl, —N═, —NR$^{11}$— or by quaternized nitrogen and is optionally substituted by $C_{1-4}$-alkyl, in particular methyl, $C_{1-4}$-dialkylamino-$C_{1-4}$-alkyl, in particular dimethylaminoethyl, hydroxyl, $C_{1-4}$-alkoxycarbonyl, but particularly preferably methoxycarbonyl, in particular pyrrolidino, 3-oxopyrrolidino, morpholino, 2,6-dimethylmorpholino, thiomorpholino, dioxothiomorpholino, $R^{10}$ represents hydrogen or $C_{1-4}$-alkyl, in particular methyl, $R^{11}$ stands straight-chain or branched $C_{1-6}$-alkyl, in particular methyl, $C_{2-6}$-alkenyl, in particular vinyl, $C_{3-6}$-cycloalkyl, in particular cyclopropyl, $C_{1-4}$-alkylcarbonyl, in particular methylcarbonyl, $C_{3-6}$-cycloalkylcarbonyl, in particular cyclopropylcarbonyl, cyclohexylcarbonyl, $C_{1-4}$-alkoxycarbonyl, in particular methoxycarbonyl, hydroxy-$C_{1-4}$-alkyl, in particular hydroxyethyl, hydroxysulphonylethyl, $C_{1-4}$-alkylamino, in particular ethylamino, $C_{1-4}$-dialkylamino-$C_{1-4}$-alkyl, in particular dimethylaminoethyl, $C_{3-7}$-cycloalkylamino-$C_{1-4}$-alkyl, in particular N-morpholinoethyl, N-piperidinoethyl, $C_{3-6}$-cycloalkylaminocarbonyl-$C_{1-2}$-alkyl, in particular N-morpholinocarbonylmethyl, B represents straight-chain or branched $C_{1-6}$-alkoxy, in particular methoxy, ethoxy, n-propoxy, sec-butoxy and tert-butoxy, $C_{2-6}$-alkenyloxy, 2-propenyloxy, 1,1-dimethyl-2-propenyloxy, $C_{2-6}$-alkinyloxy, in particular 2-propinyloxy, 1-methyl-2-propinyloxy, $C_{3-8}$-cycloalkyloxy, in particular cyclopropyloxy, aryl-$C_{1-2}$-alkyloxy, in particular benzyloxy, hetaryloxy, in particular pyridyloxy, hetaryl-$C_{1-2}$-alkyloxy, in particular pyridylmethyloxy and thiazolylmethyloxy, each of which can optionally be substituted by radicals from the series consisting of halogen, in particular fluorine, chlorine, bromine or iodine, amino, hydroxyl, $C_{1-4}$-alkoxy, in particular methoxy, $C_{1-4}$-alkylamino, in particular methylamino, $C_{1-4}$-dialkylamino, in particular dimethylamino, $C_{3-6}$-cycloalkylamino, in particular piperidino, $C_{3-6}$-cycloalkylthioamino, in particular dioxothiomorpholino, $C_{3-6}$-cycloalkyldiamino, in particular N-methyl-piperazino, or represents the amino radicals —NR$^{12}$R$^{13}$, —NR$^{14}$—NR$^{12}$R$^{13}$ and —NR$^{15}$—OR$^{16}$, in which $R^{12}$ and $R^{13}$ independently of one another represent hydrogen, straight-chain or branched $C_{1-6}$-alkyl, in particular methyl, ethyl, $C_{1-6}$-alkylcarbonyl, in particular methylcarbonyl, $C_{1-6}$-alkylsulphonyl, in particular methylsulphonyl, $C_{2-6}$-alkenyl, in particular 2-propenyl, 1-methyl-2-propenyl, $C_{2-6}$-alkinyl, in particular 2-propinyl, $C_{3-8}$-cycloalkyl, in particular cyclopropyl, cyclohexyl, $C_{3-8}$-cycloalkyl-$C_{1-2}$-alkyl, in particular cyclopropylmethyl, hydroxy-$C_{1-4}$-alkyl, in particular hydroxymethyl, hydroxyethylsulphonyl-ethyl, $C_{1-4}$-dialkylamino-$C_{1-4}$-alkyl, in particular dimethylaminoethyl, $C_{3-7}$-cycloalkylamino-$C_{1-4}$-alkyl, in particular N-morpholinoethyl, N$^1$-(N$^4$-methyl-piperazino)-ethyl, $C_{3-6}$-cycloalkylaminocarbonyl-$C_{1-2}$-alkyl, in particular N-morpholinocarbonylmethyl, or $R^{12}$ and $R^{13}$ together with the adjacent N atom represent a carbocyclic 5-, 6-, 7- or 8-membered ring system which can optionally also be interrupted by oxygen, sulphur, carbonyl, —N═, —NR$^{11}$— by quaternized nitrogen and is optionally substituted by $C_{1-4}$-alkyl, in particular methyl, $C_{1-4}$-dialkylamino-$C_{1-4}$-alkyl, in particular dimethylaminoethyl, $C_{3-6}$-cycloalkylamino, in particular piperidino, hydroxyl, $C_{1-4}$-alkoxy, in particular methoxy, $C_{1-4}$-alkylcarbonyl in particular methylcarbonyl, $C_{1-4}$-alkoxycarbonyl, in particular methoxycarbonyl, or a radical from the groups G$^4$, G$^5$, G$^6$, G$^7$ and G$^8$

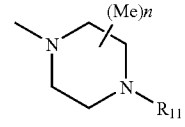

(G$^4$)

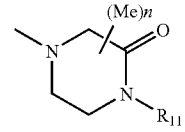

(G$^5$)

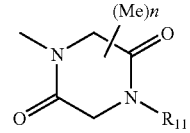

(G$^6$)

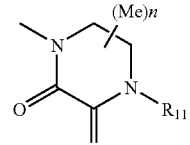

(G$^7$)

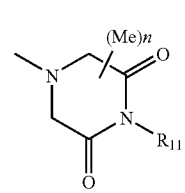

(G$^8$)

in which n can denote the numbers 0, 1 or 2, $R^{14}$ represents hydrogen, straight-chain or branched $C_{1-6}$-alkyl, in particular methyl, $R^{15}$ and $R^{16}$ independently of one another represents hydrogen, straight-chain or branched $C_{1-6}$-alkyl, in particular methyl, $C_{1-6}$-alkylcarbonyl, in particular methylcarbonyl, sec-butylcarbonyl, $C_{2-6}$-alkenyl, in particular 2-propenyl, $C_{2-6}$-alkinyl, in particular 2-propinyl, $C_{3-6}$-cycloalkyl, in particular cyclopropyl, with the proviso in the case where $R^1$ represents hydrogen and methyl, and $R^5$ represents hydrogen and

represents carboxyl,

Q represents radicals other than methyl,

B represents radicals other than —$NH_2$, and with the further proviso in the case where

represents carboxyl, and $G^2$ represents tert-butyloxy, benzyloxy and 4-nitro-benzyloxy, B represents radicals other than tert-butyloxy, benzyloxy and 4-nitro-benzyloxy, and its optical isomers and racemates.

The compound of the general formula (I) to be used according to the invention and their salts additionally contain one or more centres of chirality and can thus be present in pure stereoisomers or in the form of various enantiomer and diastereomer mixtures which, if necessary, can be separated in a manner known per se. The invention therefore relates both to the pure enantiomers and diastereomers, and to their mixtures for the control of endoparasites, particularly in the field of medicine and veterinary medicine.

Preferably, however, the optically active, stereoisomeric forms of the compounds of the general formula (I) and their salts are used according to the invention.

Suitable salts of the compounds of the general formula (I) which can be mentioned are customary non-toxic salts, i.e. salts with various bases and salts with added acids. Preferably, salts with inorganic, bases such as alkali metal salts, for example sodium, potassium or caesium salts, alkaline earth metal salts, for example calcium or magnesium salts, ammonium salts, salts with organic bases and also with organic amines, for example triethylammonium, pyridinium, picolinium, ethanolammonium, triethanolammonium, dicyclohexylammonium or N,N'-dibenzylethylenediammonium salts, salts with inorganic acids, for example hydrochlorides, hydrobromides, dihydrosulphates or trihydrophosphates, salts with organic carboxylic acids or organic sulpho acids, for example formates, acetates, trifluoroacetates, maleates, tartrates, methanesulphonates, benzenesulphonates or paratoluenesulphonates, salts with basic amino acids or acidic amino acids, for example arginates, aspartates or glutamates, may be mentioned.

In particular, the groups of compounds mentioned in the following Tables 1 to 84 may be mentioned.

Very particularly preferred compounds are those of the formula (Ia-1) and their salts, consisting of the N-methylamino acid N-methyl-alanine ($R^1$, $R^2$=methyl and $R^3$=hydrogen) and the 2-hydroxycarboxylic acid 2-hydroxyacetic acid ($R^4$, $R^5$=hydrogen) which are indicated in the following Tables 1 to 13.

TABLE 1

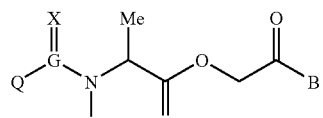

(Ia-1)

Compounds of the Table 1 correspond to the general formula (Ia-1) in which

  represents carboxyl;

Q = —$NMe_2$, B = as listed in the following:

| Compound No. | B |
|---|---|
| 1 | —O-Me |
| 2 | —O—$CH_2$-Me |
| 3 | —O—$(CH_2)_2$-Me |
| 4 | —O—$CHMe_2$ |
| 5 | —O—$CMe_3$ |
| 6 | —O—CHMe-$CH_2$-Me |
| 7 | —O—$CH_2$—CH=$CH_2$ |
| 8 | —O—CHMe-CH=$CH_2$ |
| 9 | —O—$CMe_2$-CH=$CH_2$ |
| 10 | —O—$CH_2$—C≡CH |
| 11 | —O—CHMe-C≡CH |
| 12 | —$NMe_2$ |
| 13 | —NMe-$(CH_2)_2$-Me |
| 14 | —NH-Me |
| 15 | —O-Cyclopropyl |
| 16 | (2-chloropyridin-5-yl)methoxy |
| 17 | (2-bromopyridin-5-yl)methoxy |
| 18 | (2-chlorothiazol-5-yl)methoxy |
| 19 | —NMe-$(CH_2)_3$-Me |
| 20 | —NMe-CHMe-$CH_2$-Me |
| 21 | —NMe-$(CH_2)_2$—$NMe_2$ |
| 22 | —NMe-$(CH_2)_3$—$NMe_2$ |
| 23 | —NMe-$CH_2$—CH=$CH_2$ |
| 24 | —NMe-$CH_2$—C≡CH |
| 25 | —N($CH_2$—$CH_2$—OH)$_2$ |
| 26 | —N[$(CH_2)_2$—$SO_2$—$(CH_2)_2$—OH]$_2$ |
| 27 | —NMe$(CH_2)_2$—$SO_2$—$(CH_2)_2$—OH |
| 28 | —NMe-CO—$CH_2$—O—$CH_2$—COOH |
| 29 | —NMe-O-Me |
| 30 | —N($CH_2$-Me)$_2$ |

TABLE 1-continued (Ia-1)

Compounds of the Table 1 correspond to the general formula (Ia-1) in which represents carboxyl;

Q = —NMe₂, B = as listed in the following:

| Compound No. | B |
|---|---|
| 31 | —NMe-CH₂-Me |
| 32 | —NEt-(CH₂)₂-Me |
| 33 | N-methylpiperidinyl |
| 34 | N-methyl-tetrahydropyridinyl |
| 35 | N-methylmorpholinyl |
| 36 | N-methyl-2,6-dimethylmorpholinyl |
| 37 | 1,4-dimethylpiperazine-2,5-dione |
| 38 | 1,4-dimethyl-3,6-dimethylpiperazine-2,5-dione |
| 39 | 1-methylpiperidin-3-one |
| 40 | 1-methylpiperidin-4-one |
| 41 | (6-chloropyridin-3-yl)-N,N-dimethylmethanamine |
| 42 | 1,4-dimethylpiperazine-2,6-dione |
| 43 | (2-chlorothiazol-5-yl)methyl-N-methyl |
| 44 | 1,3,4-trimethylpiperazine-2,5-dione |
| 45 | 1,3,4,6-tetramethylpiperazine-2,5-dione |
| 46 | 1,4-dimethylpiperazin-2-one |
| 47 | 1,3,4-trimethylpiperazin-2-one |

TABLE 1-continued (Ia-1)

Compounds of the Table 1 correspond to the general formula (Ia-1) in which represents carboxyl;

Q = —NMe₂, B = as listed in the following:

| Compound No. | B |
|---|---|
| 47a | 1,4-dimethyl-2,3-dioxopiperazinyl |
| 48 | 1-methyl-4-ethyl-2,3-dioxopiperazinyl |
| 49 | 4-thiomorpholinyl |
| 50 | 1,3,4-trimethyl-2,6-dioxopiperazinyl (Me at 3) |
| 51 | 1,3,4-trimethyl-2,6-dioxopiperazinyl |
| 52 | 4-thiomorpholinyl |
| 53 | 4-thiomorpholinyl-1,1-dioxide |
| 54 | 4-hydroxy-1-methylpiperidinyl |
| 55 | N-methyl-N'-morpholinyl-hydrazino |
| 56 | 3-hydroxy-1-methylpiperidinyl |
| 57 | 4-methyl-1-(2-morpholinoethyl)piperazinyl |
| 58 | 4-methyl-1-(2-morpholino-2-oxoethyl)piperazinyl |
| 59 | 4-methyl-1-(2-oxo-2-pyrrolidinylethyl)piperazinyl |
| 60 | 4-methylpiperazinyl |
| 61 | 4-ethylpiperazinyl |
| 62 | 4-isopropylpiperazinyl |

TABLE 1-continued (Ia-1)

Compounds of the Table 1 correspond to the general formula (Ia-1) in which represents carboxyl;

Q = —NMe₂, B = as listed in the following:

| Compound No. | B |
| --- | --- |
| 63 | N-methylpiperazinyl-cyclopropyl |
| 64 | N-methylpiperazinyl-CH₂CH₂-N(Me)₂ |
| 65 | N-methylpiperazinyl-CH₂CH₂-N(Et)₂ |
| 66 | N-methylpiperazinyl-CH₂CH₂-N(Pr)₂ |
| 67 | N-methylpiperazinyl-CH₂CH₂-OMe |
| 68 | N-methylpiperazinyl-C(O)OEt |
| 69 | N-methylpiperazinyl-C(O)O-allyl |
| 70 | N-methylpiperazinyl-CH₂-phenyl |
| 71 | N-methylpiperazinyl-CH₂-(1,3-benzodioxol-5-yl) |
| 72 | N-methylpiperazinyl-(2-pyrimidinyl) |
| 73 | N-methylpiperazinyl-(4-pyridinyl) |
| 74 | N-methylpiperazinyl-(2-pyridinyl) |
| 75 | N-methylpiperazinyl-CH₂-C≡CH |
| 76 | N-methylazepane (7-membered) |
| 77 | N-methylpiperazinyl-CH₂CH₂CH₂-N(Me)₂ |
| 78 | N-methylpiperazinyl-C(O)Me |

TABLE 1-continued

Compounds of the Table 1 correspond to the general formula (Ia-1) in which represents carboxyl;

Q = —NMe₂, B = as listed in the following:

| Compound No. | B |
|---|---|
| 79 | 1-methyl-4-(2,3-dimethylphenyl)piperazine |
| 80 | 1-methyl-4-(3,4-dimethoxyphenyl)piperazine |
| 81 | methyl 1-methylpiperidine-2-carboxylate |
| 82 | 3-(4-methylpiperazin-1-yl)propan-1-ol |
| 83 | methyl 1-methylpyrrolidine-2-carboxylate |
| 84 | 2-[2-(4-methylpiperazin-1-yl)-2-oxoethoxy]acetic acid |
| 85 | 3-methoxyquinuclidine |
| 86 | N-methyl-1-(4-chlorophenyl)ethylamine |
| 87 | 1-methyl-4-(pyrazin-2-yl)piperazine |
| 88 | 1-allyl-4-methylpiperazine |
| 89 | 1-methylazocane |
| 90 | N,N-diethyl-4-methylpiperazine-1-carboxamide |
| 91 | N-methyl-4-(morpholin-4-yl)aniline |

TABLE 1-continued (Ia-1)

Compounds of the Table 1 correspond to the general formula (Ia-1) in which represents carboxyl;

Q = —NMe₂, B = as listed in the following:

| Compound No. | B |
|---|---|
| 92 | 2-methoxyphenyl-morpholine |
| 93 | 1'-methyl-[1,4'-bipiperidine] |
| 94 | 1-methylpyrrolidine |
| 95 | 2-methyl-2-azaspiro[5.5]undecane |
| 96 | 1,2-dimethylpiperidine |
| 97 | 1,3-dimethylpiperidine |
| 98 | 1-methyl-4-phenylpiperidine-4-carbonitrile |
| 99 | N-methyl-2-morpholinoaniline |
| 100 | 3-methoxyphenyl-morpholine |
| 101 | tert-butyl (1-methylpiperidin-4-yl)carbamate |
| 102 | 1-methylpiperidin-4-aminium chloride |
| 103 | 4-methoxy-1-methylpiperidine |
| 104 | 1,3,3-trimethylpiperidine |
| 105 | 1,3,5-trimethylpiperidine |

TABLE 1-continued

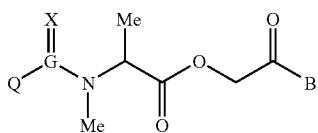
(Ia-1)

Compounds of the Table 1 correspond to
the general formula (Ia-1) in which

 represents carboxyl;

Q = —NMe$_2$, B = as listed in the following:

Compound No.    B

Abbreviations: Me: methyl; Et: ethyl, Pr: propyl; Bu: butyl; i-, s- and t-: iso-, secondary- and tertiary

TABLE 2

Table 2 contains the compounds of the general formula (Ia-1) in which

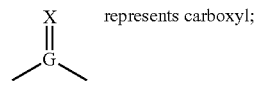 represents carboxyl;

Q represents —NEt$_2$ and B has the meanings listed in Table 1.

TABLE 3

Table 3 contains the compounds of the general formula (Ia-1) in which

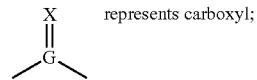 represents carboxyl;

Q represents —O-Me and B has the meanings listed in Table 1.

TABLE 4

Table 4 contains the compounds of the general formula (Ia-1) in which

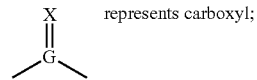 represents carboxyl;

Q represents —O—CHMe-CH$_2$-Me and B has the meanings listed in Table 1.

TABLE 5

Table 5 contains the compounds of the general formula (Ia-1) in which

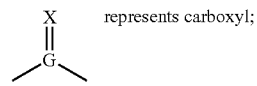 represents carboxyl;

Q represents —O—CH$_2$—CH=CH$_2$ and B has the meanings listed in Table 1.

TABLE 6

Table 6 contains the compounds of the general formula (Ia-1) in which

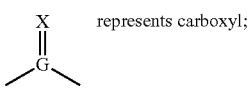 represents carboxyl;

Q represents —O—CHMe-CH=CH$_2$ and B has the meanings listed in Table 1.

TABLE 7

Table 7 contains the compounds of the general formula (Ia-1) in which

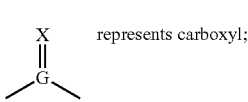 represents carboxyl;

Q represents —O—CH$_2$—C≡CH and B has the meanings listed in Table 1.

TABLE 8

Table 8 contains the compounds of the general formula (Ia-1) in which

 represents carboxyl;

Q represents —O—CMe=CH$_2$ and B has the meanings listed in Table 1.

TABLE 9

Table 9 contains the compounds of the general formula (Ia-I) in which

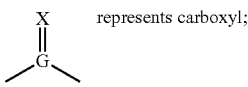 represents carboxyl;

Q represents —NMe—CO—NMe$_2$ and B has the meanings listed in Table 1.

TABLE 10

Table 10 contains the compounds of the general formula (Ia-1) in which

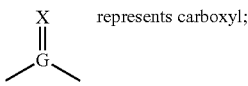 represents carboxyl;

Q represents —NMe-CO—NEt$_2$ and B has the meanings listed in Table 1.

TABLE 11

Table 11 contains the compounds of the general formula (Ia-1) in which

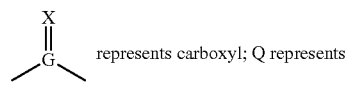 represents carboxyl; Q represents

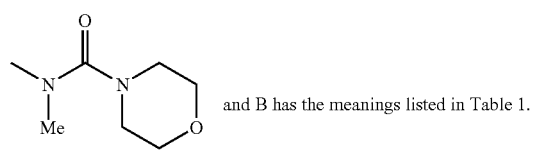 and B has the meanings listed in Table 1.

TABLE 12

Table 12 contains the compounds of the general formula (Ia-1) in which

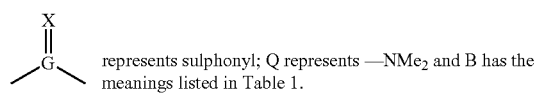 represents sulphonyl; Q represents —NMe$_2$ and B has the meanings listed in Table 1.

TABLE 13

Table 13 contains the compounds of the general formula (Ia-1) in which

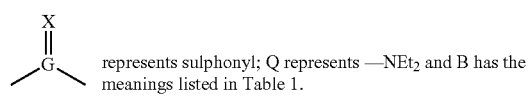 represents sulphonyl; Q represents —NEt$_2$ and B has the meanings listed in Table 1.

TABLE 14

Table 14 contains the compounds of the general formula (Ia-1) in which

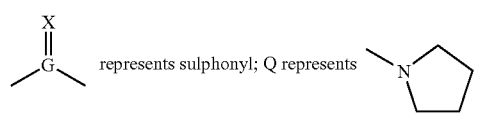 represents sulphonyl; Q represents and B has the meanings listed in Table 1.

Furthermore preferred are the compounds of the formula (Ia-2) and their salts, consisting of the N-methyl-amino acid N-methyl-alanine ($R^1$, $R^2$=methyl and $R^3$=hydrogen) and the 2-hydroxycarboxylic acid 2-hydroxy-propionic acid (lactic acid) $R^4$=hydrogen; $R^5$=methyl).

Very particularly preferred examples of these new compounds (Ia-2) according to the invention are mentioned in Tables 15-28.

TABLE 15

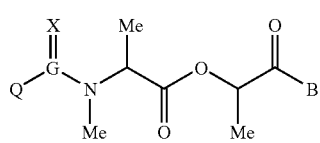 (Ia-2)

Compounds of Table 15 correspond to the general formula (Ia-2) in which

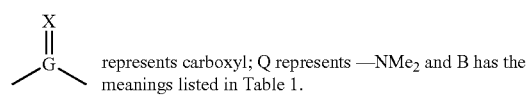 represents carboxyl; Q represents —NMe$_2$ and B has the meanings listed in Table 1.

TABLE 16

Table 16 contains the compounds of the general formula (Ia-2) in which

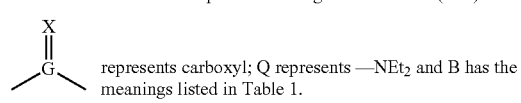 represents carboxyl; Q represents —NEt$_2$ and B has the meanings listed in Table 1.

TABLE 17

Table 17 contains the compounds of the general formula (Ia-2) in which represents carboxyl; Q represents —O—Me and B has the meanings listed in Table 1.

TABLE 18

Table 18 contains the compounds of the general formula (Ia-2) in which

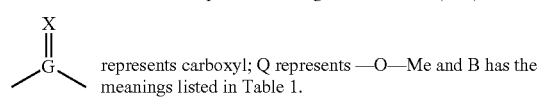 represents carboxyl; Q represents —O—CHMe—CH$_2$—Me and B has the meanings listed in Table 1.

TABLE 19

Table 19 contains the compounds of the general formula (Ia-2) in which

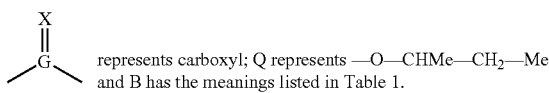 represents carboxyl; Q represents —O—CH$_2$—CH=CH$_2$ and B has the meanings listed in Table 1.

TABLE 20

Table 20 contains the compounds of the general formula (Ia-2) in which

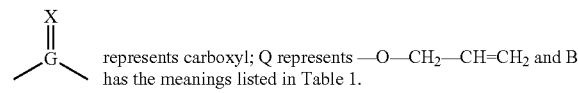 represents carboxyl; Q represents —O—CHMe—CH=CH$_2$ and B has the meanings listed in Table 1.

TABLE 21

Table 21 contains the compounds of the general formula (Ia-2) in which

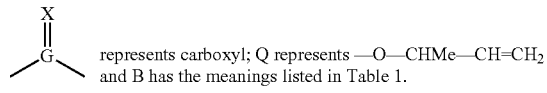

represents carboxyl; Q represents —O—CH$_2$—C≡CH and B has the meanings listed in Table 1.

TABLE 22

Table 22 contains the compounds of the general formula (Ia-2) in which

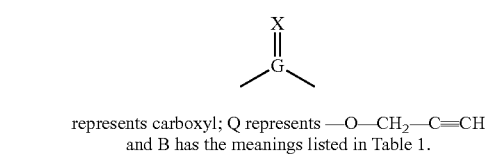

represents carboxyl; Q represents —O—CMe=CH$_2$ and B has the meanings listed in Table 1.

TABLE 23

Table 23 contains the compounds of the general formula (Ia-2) in which

represents carboxyl; Q represents —NMe-CO—NMe$_2$ and B has the meanings listed in Table 1.

TABLE 24

Table 24 contains the compounds of the general formula (Ia-2) in which

represents carboxyl; Q represents —NMe-CO—NEt$_2$ and B has the meanings listed in Table 1.

TABLE 25

Table 25 contains the compounds of the general formula (Ia-2) in which

represents carboxyl; Q represents

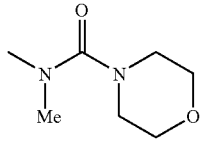

and B has the meanings listed in Table 1.

TABLE 26

Table 26 contains the compounds of the general formula (Ia-2) in which

represents sulphonyl; Q represents —NMe$_2$ and B has the meanings listed in Table 1.

TABLE 27

Table 27 contains the compounds of the general formula (Ia-2) in which

represents sulphonyl; Q represents —NEt$_2$ and B has the meanings listed in Table 1.

TABLE 28

Table 28 contains the compounds of the general formula (Ia-2) in which

represents sulphonyl; Q represents

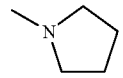

and B has the meanings listed in Table 1.

Furthermore preferred are the compounds of the formula (Ia-3) and their salts, consisting of the N-methyl-amino acid N-methyl-alanine ($R^1$, $R^2$=methyl and $R^3$=hydrogen) and the 2-hydroxycarboxylic acid 2-hydroxy-butyric acid ($R^4$=hydrogen; $R^5$=ethyl).

Very particularly preferred examples of these new compounds (Ia-3) according to the invention are mentioned in Tables 29-42.

TABLE 29

(Ia-3)

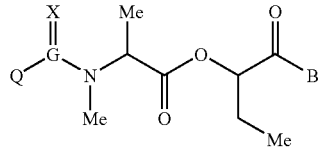

Compounds of Table 29 correspond to the general formula (Ia-3) in which

represents carboxyl; Q represents —NMe$_2$ and B has the meanings listed in Table 1.

TABLE 30

Table 30 contains the compounds of the general formula (Ia-3) in which

represents carboxyl; Q represents —NEt$_2$ and B has the meanings listed in Table 1.

TABLE 31

Table 31 contains the compounds of the general formula (Ia-3) in which

represents carboxyl; Q represents —O-Me and B has the meanings listed in Table 1.

TABLE 32

Table 32 contains the compounds of the general formula (Ia-3) in which

represents carboxyl; Q represents —O—CHMe-CH$_2$-Me and B has the meanings listed in Table 1.

TABLE 33

Table 33 contains the compounds of the general formula (Ia-3) in which

represents carboxyl; Q represents —O—CH$_2$—CH=CH$_2$ and B has the meanings listed in Table 1.

TABLE 34

Table 34 contains the compounds of the general formula (Ia-3) in which

represents carboxyl; Q represents —O—CHMe-CH=CH$_2$ and B has the meanings listed in Table 1.

TABLE 35

Table 35 contains the compounds of the general formula (Ia-3) in which

represents carboxyl; Q represents —O—CH$_2$C≡CH and B has the meanings listed in Table 1.

TABLE 36

Table 36 contains the compounds of the general formula (Ia-3) in which

represents carboxyl; Q represents —O—CMe=CH$_2$ and B has the meanings listed in Table 1.

TABLE 37

Table 37 contains the compounds of the general formula (Ia-3) in which

represents carboxyl; Q represents —NMe-CO—NMe$_2$ and B has the meanings listed in Table 1.

TABLE 38

Table 38 contains the compounds of the general formula (Ia-3) in which

represents carboxyl; Q represents —NMe-CO—NEt$_2$ and B has the meanings listed in Table 1.

TABLE 39

Table 39 contains the compounds of the general formula (Ia-3) in which

represents carboxyl; Q represents

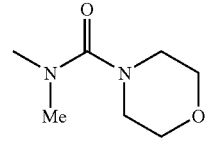

and B has the meanings listed in Table 1.

TABLE 40

Table 40 contains the compounds of the general formula (Ia-3) in which

represents sulphonyl; Q represents —NMe$_2$ and B has the meanings listed in Table 1.

TABLE 41

Table 41 contains the compounds of the general formula (Ia-3) in which

represents sulphonyl; Q represents —NEt$_2$ and B has the meanings listed in Table 1.

TABLE 42

Table 42 contains the compounds of the general formula (Ia-3) in which

represents sulphonyl; Q represents

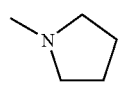

and B has the meanings listed in Table 1.

Furthermore preferred are the compounds of the formula (Ia-4) and their salts, consisting of the N-methyl-amino acid N-methyl-aminobutyric acid ($R^1$=methyl, $R^2$=ethyl and $R^3$=hydrogen) and the 2-hydroxycarboxylic acid 2-hydroxyacetic acid ($R^4$, $R^5$=hydrogen).

Very particularly preferred examples of these new compounds (Ia-4) according to the invention are mentioned in Tables 43-56.

TABLE 43

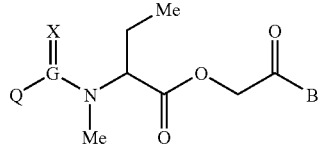
(Ia-4)

Compounds of Table 43 correspond to the general formula (Ia-4) in which

represents carboxyl; Q represents —$NMe_2$ and B has the meanings listed in Table 1.

TABLE 44

Table 44 contains the compounds of the general formula (Ia-4) in which

represents carboxyl; Q represents —$NEt_2$ and B has the meanings listed in Table 1.

TABLE 45

Table 45 contains the compounds of the general formula (Ia-4) in which

represents carboxyl; Q represents —O—Me and B has the meanings listed in Table 1.

TABLE 46

Table 46 contains the compounds of the general formula (Ia-4) in which

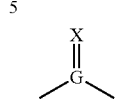

represents carboxyl; Q represents —O—CHMe-$CH_2$-Me and B has the meanings listed in Table 1.

TABLE 47

Table 47 contains the compounds of the general formula (Ia-4) in which

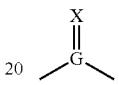

represents carboxyl; Q represents —O—$CH_2$—CH=$CH_2$ and B has the meanings listed in Table 1.

TABLE 48

Table 48 contains the compounds of the general formula (Ia-4) in which

represents carboxyl; Q represents —O—CHMe-CH=$CH_2$ and B has the meanings listed in Table 1.

TABLE 49

Table 49 contains the compounds of the general formula (Ia-4) in which

represents carboxyl; Q represents —O—$CH_2$—C≡CH and B has the meanings listed in Table 1.

TABLE 50

Table 50 contains the compounds of the general formula (Ia-4) in which

represents carboxyl; Q represents —O—CMe=$CH_2$ and B has the meanings listed in Table 1.

TABLE 51

Table 51 contains the compounds of the general formula (Ia-4) in which

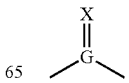 represents carboxyl; Q represents —NMe—CO—$NMe_2$ and B has the meanings listed in Table1.

TABLE 52

Table 52 contains the compounds of the general formula (Ia-4) in which

[structure: X=G with bond] represents carboxyl; Q represents —NMe-CO—NEt$_2$ and B has the meanings listed in Table 1.

TABLE 53

Table 53 contains the compounds of the general formula (Ia-4) in which

[structure: X=G with bond] represents carboxyl; Q represents

[structure: MeN(Me)-C(=O)-N-morpholine] and B has the meanings listed in Table 1.

TABLE 54

Table 54 contains the compounds of the general formula (Ia-4) in which

[structure: X=G] represents sulphonyl; Q represents —NMe$_2$ and B has the meanings listed in Table 1.

TABLE 55

Table 55 contains the compounds of the general formula (Ia-4) in which

[structure: X=G] represents sulphonyl; Q represents —NEt$_2$ and B has the meanings listed in Table 1.

TABLE 56

Table 56 contains the compounds of the general formula (Ia-4) in which

[structure: X=G] represents sulphonyl; Q represents [pyrrolidine]

and B has the meanings listed in Table 1.

Furthermore preferred are the compounds of the formula (Ia-5) and their salts, consisting of the N-methyl-amino acid N-methyl-aminobutyric acid ($R^1$=methyl, $R^2$=ethyl and $R^3$=hydrogen) and the 2-hydroxycarboxylic acid 2-hydroxypropionic acid (lactic acid) ($R^4$=hydrogen; $R^5$=methyl).

Very particularly preferred examples of these new compounds (Ia-5) according to the invention are mentioned in Tables 57-70.

TABLE 57

(Ia-5)

[structure of formula (Ia-5)]

Compounds of Table 43 correspond to the general formula (Ia-5) in which

[structure: X=G] represents carboxyl; Q represents —NMe$_2$ and B has the meanings listed in Table 1.

TABLE 58

Table 58 contains the compounds of the general formula (Ia-5) in which

[structure: X=G] represents carboxyl; Q represents —NEt$_2$ and B has the meanings listed in Table 1.

TABLE 59

Table 59 contains the compounds of the general formula (Ia-5) in which

[structure: X=G] represents carboxyl; Q represents —O-Me and B has the meanings listed in Table 1.

TABLE 60

Table 60 contains the compounds of the general formula (Ia-5) in which

[structure: X=G] represents carboxyl; Q represents —O—CHMe-CH$_2$-Me and B has the meanings listed in Table 1.

TABLE 61

Table 61 contains the compounds of the general formula (Ia-5) in which

[structure: X=G] represents carboxyl; Q represents —O—CH$_2$—CH=CH$_2$ and B has the meanings listed in Table 1.

TABLE 62

Table 62 contains the compounds of the general formula (Ia-5) in which

[structure: X=G] represents carboxyl; Q represents —O—CHMe-CH=CH$_2$ and B has the meanings listed in Table 1.

TABLE 63

Table 63 contains the compounds of the general formula (Ia-5) in which

represents carboxyl; Q represents —O—CH$_2$—C≡CH and B has the meanings listed in Table 1.

TABLE 64

Table 64 contains the compounds of the general formula (Ia-5) in which

represents carboxyl; Q represents —O—CMe═CH$_2$ and B has the meanings listed in Table 1.

TABLE 65

Table 65 contains the compounds of the general formula (Ia-5) in which

represents carboxyl; Q represents —NMe-CO—NMe$_2$ and B has the meanings listed in Table 1.

TABLE 66

Table 66 contains the compounds of the general formula (Ia-5) in which

represents carboxyl; Q represents —NMe-CO—NEt$_2$ and B has the meanings listed in Table 1.

TABLE 67

Table 67 contains the compounds of the general formula (Ia-5) in which

represents carboxyl; Q represents

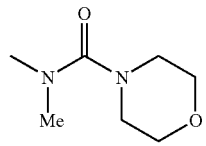

and B has the meanings listed in Table 1.

TABLE 68

Table 68 contains the compounds of the general formula (Ia-5) in which

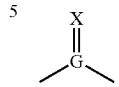

represents sulphonyl; Q represents —NMe$_2$ and B has the meanings listed in Table 1.

TABLE 69

Table 69 contains the compounds of the general formula (Ia-5) in which

represents sulphonyl; Q represents —NEt$_2$ and B has the meanings listed in Table 1.

TABLE 70

Table 70 contains the compounds of the general formula (Ia-5) in which

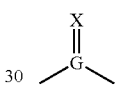

represents sulphonyl; Q represents

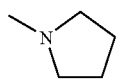

and B [lacuna] the [lacuna] in Table 1 listed.

Furthermore preferred are the compounds of the formula (Ia-6) and their salts, consisting of the N-methyl-amino acid N-methyl-aminobutyric acid (R$^1$=methyl, R$^2$=ethyl and R$^3$=hydrogen) and the 2-hydroxycarboxylic acid 2-hydroxybutyric acid (R$^4$=hydrogen; R$^5$=ethyl).

Very particularly preferred examples of these new compounds (Ia-6) according to the invention are mentioned in Tables 71-84.

TABLE 71

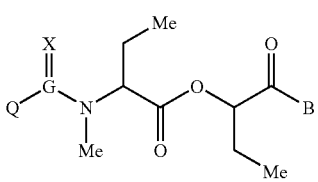

(Ia-6)

Compounds of Table 71 correspond to the general formula (Ia-6) in which

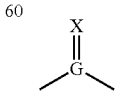

represents carboxyl; Q represents —NMe$_2$ and B has the meanings listed in Table 1.

TABLE 72

Table 72 contains the compounds of the general formula (Ia-6) in which

represents carboxyl; Q represents —NEt$_2$ and B has the meanings listed in Table 1.

TABLE 73

Table 73 contains the compounds of the general formula (Ia-6) in which

represents carboxyl; Q represents —O-Me and B has the meanings listed in Table 1.

TABLE 74

Table 74 contains the compounds of the general formula (Ia-6) in which

represents carboxyl; Q represents —O—CHMe-CH$_2$-Me and B has the meanings listed in Table 1.

TABLE 75

Table 75 contains the compounds of the general formula (Ia-6) in which

represents carboxyl; Q represents —O—CH$_2$—CH=CH$_2$ and B has the meanings listed in Table 1.

TABLE 76

Table 76 contains the compounds of the general formula (Ia-6) in which

represents carboxyl; Q represents —O—CHMe-CH=CH$_2$ and B has the meanings listed in Table 1.

TABLE 77

Table 77 contains the compounds of the general formula (Ia-6) in which

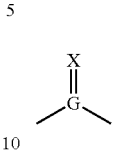

represents carboxyl; Q represents —O—CH$_2$—C≡CH and B has the meanings listed in Table 1.

TABLE 78

Table 78 contains the compounds of the general formula (Ia-6) in which

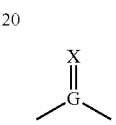

represents carboxyl; Q represents —O—CMe=CH$_2$ and B has the meanings listed in Table 1.

TABLE 79

Table 79 contains the compounds of the general formula (Ia-6) in which

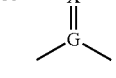

represents carboxyl; Q represents —NMe-CO—NMe$_2$ and B has the meanings listed in Table 1.

TABLE 80

Table 80 contains the compounds of the general formula (Ia-6) in which

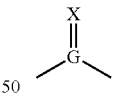

represents carboxyl; Q represents —NMe—CO-NEt$_2$ and B has the meanings listed in Table 1.

TABLE 81

Table 81 contains the compounds of the general formula (Ia-6) in which

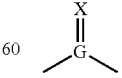 represents carboxyl, Q represents

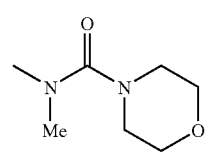

and B has the meanings listed in Table 1.

TABLE 82

Table 82 contains the compounds of the general formula (Ia-6) in which

 represents sulphonyl; Q represents —NMe$_2$ and B has the meanings listed in Table 1.

TABLE 83

Table 83 contains the compounds of the general formula (Ia-6) in which

 represents sulphonyl; Q represents —NEt$_2$ and B has the meanings listed in Table 1.

TABLE 84

Table 84 contains the compounds of the general formula (Ia-6) in which

 represents sulphonyl; Q represents 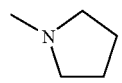

and B has the meanings listed in Table 1.

In detail, the following compounds of the general formula (Ia) may be mentioned in which the radicals R$^1$ to R$^5$, G, Q, X and B have the following meaning:

| Q | G=X | R$^1$ | R$^2$ | R$^3$ | R$^4$ | R$^5$ | B |
|---|---|---|---|---|---|---|---|
| Me$_2$N—CO—NMe- | C=O | -Me | -Me | —H | —H | -Me | morpholine |
| Et$_2$N—CO—NMe- | C=O | -Me | -Me | —H | —H | -Me | morpholine |
| Me-CH$_2$-MeCH—O— | C=O | -Me | -Me | —H | —H | -Me | morpholine |
| H$_2$C=CH—CHMe-O— | C=O | -Me | -Me | —H | —H | -Me | morpholine |
| H$_2$C=CMe-O— | C=O | -Me | -Me | —H | —H | -Me | morpholine |
| HC≡C—CH$_2$—O— | C=O | -Me | -Me | —H | —H | -Me | morpholine |
| Et$_2$N— | SO$_2$ | -Me | -Me | —H | —H | -Me | morpholine |
| Me$_2$N— | C=O | -Me | -Me | —H | —H | -Me | morpholine |

-continued

| Q | G=X | R¹ | R² | R³ | R⁴ | R⁵ | B |
|---|---|---|---|---|---|---|---|
| Me₂N— | SO₂ | -Me | -Me | —H | —H | -Me | morpholine |
| Et₂N— | C=O | -Me | -Me | —H | —H | -Me | morpholine |
| pyrrolidinyl | SO₂ | -Me | -Me | —H | —H | -Me | morpholine |
| 4-Me-piperazinyl | SO₂ | -Me | -Me | —H | —H | -Me | morpholine |
| morpholinyl | SO₂ | -Me | -Me | —H | —H | -Me | morpholine |
| morpholinyl | C=O | -Me | -Me | —H | —H | -Me | morpholine |
| morpholine-4-carbonyl-N(Me)- | C=O | -Me | -Me | —H | —H | -Me | morpholine |
| morpholin-4-yl-N(H)- | C=O | -Me | -Me | —H | —H | -Me | morpholine |
| 4-Cl-C₆H₄-CH₂-N(Me)- | =C(Me)-NO₂ | -Me | -Me | —H | —H | -Me | morpholine |
| 4-Cl-C₆H₄-CH₂-N(Me)- | =C(Me)-CN | -Me | -Me | —H | —H | -Me | morpholine |
| 4-Cl-C₆H₄-CH₂-N(Me)- | =N-CN (C(Me)₂) | -Me | -Me | —H | —H | -Me | morpholine |
| Me₂N—CO—NMe- | C=O | -Me | -Me | —H | —H | -Me | 2,6-dimethyl-4-methyl-morpholine |

-continued

| Q | G=X | R¹ | R² | R³ | R⁴ | R⁵ | B |
|---|---|---|---|---|---|---|---|
| Et₂N—CO—NMe- | C=O | -Me | -Me | —H | —H | -Me | 2,6-dimethyl-4-methylmorpholine |
| Me-CH₂-MeCH—O— | C=O | -Me | -Me | —H | —H | -Me | 2,6-dimethyl-4-methylmorpholine |
| H₂C=CH—CH₂—O— | C=O | -Me | -Me | —H | —H | -Me | 2,6-dimethyl-4-methylmorpholine |
| H₂C=CH—CHMe-O— | C=O | -Me | -Me | —H | —H | -Me | 2,6-dimethyl-4-methylmorpholine |
| H₂C=CMe-O— | C=O | -Me | -Me | —H | —H | -Me | 2,6-dimethyl-4-methylmorpholine |
| HC≡C—CH₂—O— | C=O | -Me | -Me | —H | —H | -Me | 2,6-dimethyl-4-methylmorpholine |
| Et₂N— | SO₂ | -Me | -Me | —H | —H | -Me | 2,6-dimethyl-4-methylmorpholine |
| Me₂N— | C=O | -Me | -Me | —H | —H | -Me | 2,6-dimethyl-4-methylmorpholine |

-continued
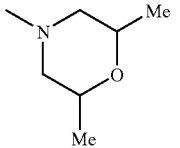
| Q | G=X | R¹ | R² | R³ | R⁴ | R⁵ | B |
|---|---|---|---|---|---|---|---|
| Me₂N— | SO₂ | -Me | -Me | —H | —H | -Me | 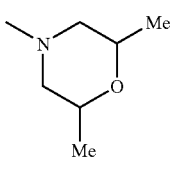 |
| Et₂N— | C=O | -Me | -Me | —H | —H | -Me | 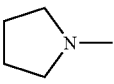 |
| 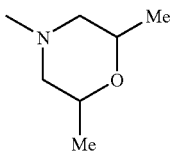 | SO₂ | -Me | -Me | —H | —H | -Me | 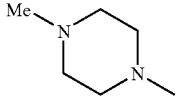 |
| 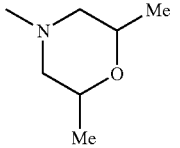 | SO₂ | -Me | -Me | —H | —H | -Me | 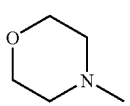 |
| 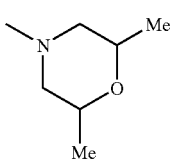 | SO₂ | -Me | -Me | —H | —H | -Me | 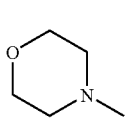 |
| 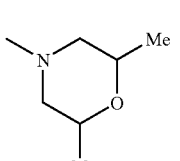 | C=O | -Me | -Me | —H | —H | -Me | 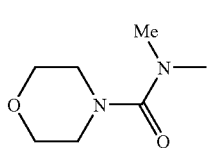 |
| 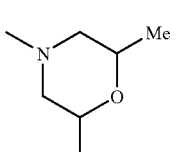 | C=O | -Me | -Me | —H | —H | -Me | 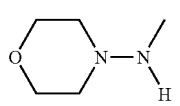 |
| 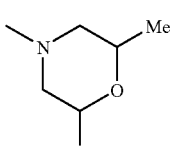 | C=O | -Me | -Me | —H | —H | -Me |  |

-continued
| Q | G=X | R¹ | R² | R³ | R⁴ | R⁵ | B |
|---|---|---|---|---|---|---|---|
| 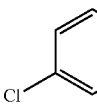 | 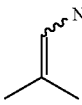 | -Me | -Me | —H | —H | -Me | 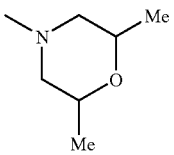 |
| 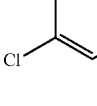 | 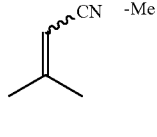 | -Me | -Me | —H | —H | -Me | 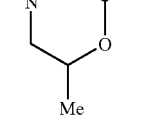 |
| 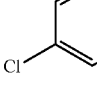 | 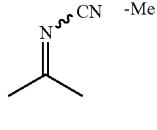 | -Me | -Me | —H | —H | -Me | 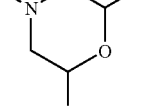 |
| Me₂N—CO—NMe- | C=O | -Me | -Me | —H | —H | -Me | 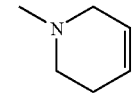 |
| Me-CH₂-MeCH—O— | C=O | -Me | -Me | —H | —H | -Me | 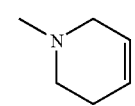 |
| H₂C=CH—CHMe-O— | C=O | -Me | -Me | —H | —H | -Me | 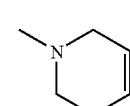 |
| H₂C=CMe-O— | C=O | -Me | -Me | —H | —H | -Me | 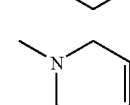 |
| HC≡C—CH₂—O— | C=O | -Me | -Me | —H | —H | -Me | 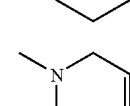 |
| Me₂N— | C=O | -Me | -Me | —H | —H | -Me | 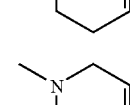 |
| Et₂N— | C=O | -Me | -Me | —H | —H | -Me | 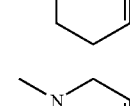 |
| 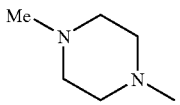 | SO₂ | -Me | -Me | —H | —H | -Me | 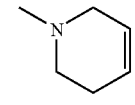 |

-continued

| Q | G=X | R¹ | R² | R³ | R⁴ | R⁵ | B |
|---|---|---|---|---|---|---|---|
| *N-methylmorpholine* | SO₂ | -Me | -Me | —H | —H | -Me | *N-methyl-tetrahydropyridine* |
| *morpholine-N-C(=O)-NMe-* | C=O | -Me | -Me | —H | —H | -Me | *N-methyl-tetrahydropyridine* |
| *morpholine-N-NH-* | C=O | -Me | -Me | —H | —H | -Me | *N-methyl-tetrahydropyridine* |
| *4-Cl-C₆H₄-CH₂-N(Me)-* | =C(NO₂)(iPr) | -Me | -Me | —H | —H | -Me | *N-methyl-tetrahydropyridine* |
| *4-Cl-C₆H₄-CH₂-N(Me)-* | =C(CN)(iPr) | -Me | -Me | —H | —H | -Me | *N-methyl-tetrahydropyridine* |
| *4-Cl-C₆H₄-CH₂-N(Me)-* | N-CN (=C(Me)₂) | -Me | -Me | —H | —H | -Me | *N-methyl-tetrahydropyridine* |
| Me₂N—CO—NMe- | C=O | -Me | -Me | —H | —H | -Me | *N-methyl-thiomorpholine-1,1-dioxide* |
| Me-CH₂-MeCH—O— | C=O | -Me | -Me | —H | —H | -Me | *N-methyl-thiomorpholine-1,1-dioxide* |
| H₂C=CH—CH₂—O— | C=O | -Me | -Me | —H | —H | -Me | *N-methyl-thiomorpholine-1,1-dioxide* |
| H₂C=CH—CHMe-O— | C=O | -Me | -Me | —H | —H | -Me | *N-methyl-thiomorpholine-1,1-dioxide* |
| H₂C=CMe-O— | C=O | -Me | -Me | —H | —H | -Me | *N-methyl-thiomorpholine-1,1-dioxide* |

-continued
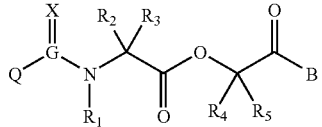
| Q | G=X | R¹ | R² | R³ | R⁴ | R⁵ | B |
|---|-----|----|----|----|----|----|---|
| HC≡C—CH₂—O— | C=O | -Me | -Me | —H | —H | -Me | 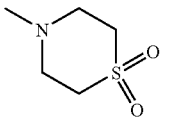 |
| Me₂N— | C=O | -Me | -Me | —H | —H | -Me | 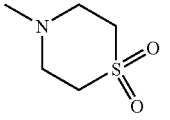 |
| Et₂N— | C=O | -Me | -Me | —H | —H | -Me | 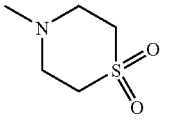 |
| 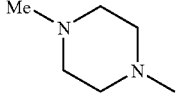 | SO₂ | -Me | -Me | —H | —H | -Me | 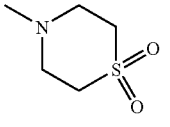 |
| 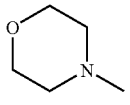 | SO₂ | -Me | -Me | —H | —H | -Me | 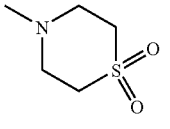 |
|  | 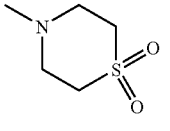 | -Me | -Me | —H | —H | -Me |  |
| 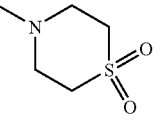 |  | -Me | -Me | —H | —H | -Me | 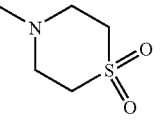 |
| 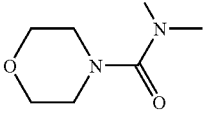 | 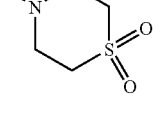 | -Me | -Me | —H | —H | -Me | 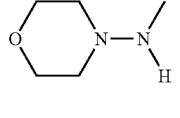 |
| 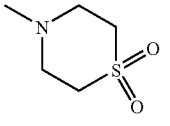 | C=O | -Me | -Me | —H | —H | -Me |  |
|  | C=O | -Me | -Me | —H | —H | -Me |  |
| Me₂N—CO—NMe | C=O | -Me | -Me | —H | —H | -Me | —O-Et |
| Me-CH₂—MeCH—O— | C=O | -Me | -Me | —H | —H | -Me | —O-Et |
| H₂C=CH—CH₂—O— | C=O | -Me | -Me | —H | —H | -Me | —O-Et |
| H₂C=CH—CHMe-O— | C=O | -Me | -Me | —H | —H | -Me | —O-Et |

-continued

| Q | G=X | R¹ | R² | R³ | R⁴ | R⁵ | B |
|---|---|---|---|---|---|---|---|
| H₂C=CMe-O— | C=O | -Me | -Me | —H | —H | -Me | —O-Et |
| HC≡C—CH₂—O— | C=O | -Me | _me | —H | —H | -Me | —O-Et |
| Me₂N— | C=O | -Me | -Me | —H | —H | -Me | —O-Et |
| Et₂N— | C=O | -Me | -Me | —H | —H | -Me | —O-Et |
| Me-N(piperazine)-N— | SO₂ | -Me | -Me | —H | —H | -Me | —O-Et |
| morpholine-N— | SO₂ | -Me | -Me | —H | —H | -Me | —O-Et |
| 4-Cl-C₆H₄-CH₂-N(Me)- (C=CMe-NO₂) | | -Me | -Me | —H | —H | -Me | —O-Et |
| 4-Cl-C₆H₄-CH₂-N(Me)- (C=CMe-CN) | | -Me | -Me | —H | —H | -Me | —O-Et |
| 4-Cl-C₆H₄-CH₂-N(Me)- (N=CMe-CN) | | -Me | -Me | —H | —H | -Me | —O-Et |
| morpholine-N-C(=O)-N(Me)- | C=O | -Me | -Me | —H | —H | -Me | —O-Et |
| morpholine-N-NH- | C=O | -Me | -Me | —H | —H | -Me | —O-Et |
| Me₂N—CO—NMe | C=O | -Me | -Me | —H | —H | -Me | —NMe₂ |
| Me-CH₂MeCH—O— | C=O | -Me | -Me | —H | —H | -Me | —NMe₂ |
| H₂C=CH—CH₂—O— | C=O | -Me | -Me | —H | —H | -Me | —NMe₂ |
| H₂NC=CH—CHMe-O— | C=O | -Me | -Me | —H | —H | -Me | —NMe₂ |
| H₂C=CMe-O— | C=O | -Me | -Me | —H | —H | -Me | —NMe₂ |
| HC≡C—CH₂—O— | C=O | -Me | -Me | —H | —H | -Me | —NMe₂ |
| Me₂N— | C=O | -Me | -me | —H | —H | -Me | —NMe₂ |
| Et₂N— | C=O | -Me | -Me | —H | —H | -Me | —NMe₂ |
| Me-N(piperazine)-N— | SO₂ | -Me | -Me | —H | —H | -Me | —NMe₂ |
| morpholine-N— | SO₂ | -Me | -Me | —H | —H | -Me | —NMe₂ |

-continued

| Q | G=X | R¹ | R² | R³ | R⁴ | R⁵ | B |
|---|---|---|---|---|---|---|---|
| 4-Cl-C₆H₄-CH₂-N(Me)- | =CH-C(Me)=CH-NO₂ | -Me | -Me | —H | —H | -Me | —NMe₂ |
| 4-Cl-C₆H₄-CH₂-N(Me)- | =CH-C(Me)=CH-CN | -Me | -Me | —H | —H | -Me | —NMe₂ |
| 4-Cl-C₆H₄-CH₂-N(Me)- | =N-C(Me)=CH-CN (hydrazono) | -Me | -Me | —H | —H | -Me | —NMe₂ |
| morpholine-N-C(=O)-N(Me)- | C=O | -Me | -Me | —H | —H | -Me | —NMe₂ |
| morpholine-N-N(H)- | C=O | -Me | -Me | —H | —H | -Me | —NMe₂ |
| Me₂N—CO—NMe- | C=O | -Me | -Me | —H | —H | -Me | —NEt₂ |
| Me-CH₂-MeCH—O— | C=O | -Me | -Me | —H | —H | -Me | —NEt₂ |
| H₂C=CH—CH₂—O— | C=O | -Me | -Me | —H | —H | -Me | —NEt₂ |
| H₂C=CH—CHMe-O— | C=O | -Me | -Me | —H | —H | -Me | —NEt₂ |
| H₂C=CMe-O— | C=O | -Me | -Me | —H | —H | -Me | —NEt₂ |
| HC≡C—CH₂—O— | C=O | -Me | -Me | —H | —H | -Me | —NEt₂ |
| Me₂N— | C=O | -Me | -Me | —H | —H | -Me | —NEt₂ |
| Et₂N— | C=O | -Me | -Me | —H | —H | -Me | —NEt₂ |
| 4-Cl-C₆H₄-CH₂-N(Me)- | =CH-C(Me)=CH-NO₂ | -Me | -Me | —H | —H | -Me | —NEt₂ |
| morpholine-N-C(=O)-N(Me)- | C=O | -Me | -Me | —H | —H | -Me | —NEt₂ |
| Me₂N—CO—NMe- | C=O | -Me | -Me | —H | —H | -Me | 1-methyl-3-oxopiperidin-3-yl |
| Me-CH₂-MeCH—O— | C=O | -Me | -Me | —H | —H | -Me | 1-methyl-3-oxopiperidin-3-yl |
| H₂C=CH—CH₂—O— | C=O | -Me | -Me | —H | —H | -Me | 1-methyl-3-oxopiperidin-3-yl |

-continued
| Q | G=X | R¹ | R² | R³ | R⁴ | R⁵ | B |
|---|---|---|---|---|---|---|---|
| H₂C=CH—CHMe-O— | C=O | -Me | -Me | —H | —H | -Me | 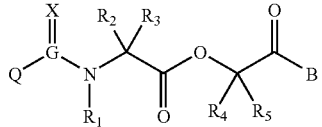 |
| H₂C=CMe-O— | C=O | -Me | -Me | —H | —H | -Me | 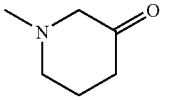 |
| HC≡C—CH₂—O— | C=O | -Me | -Me | —H | —H | -Me | 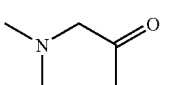 |
| Me₂N— | C=O | -Me | -Me | —H | —H | -Me | 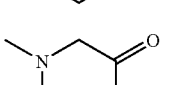 |
| Et₂N— | C=O | -Me | -Me | —H | —H | -Me | 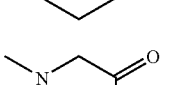 |
| 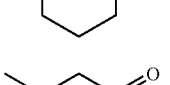 | SO₂ | -Me | -Me | —H | —H | -Me | 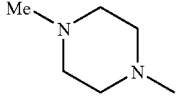 |
| 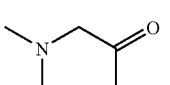 | SO₂ | -Me | -Me | —H | —H | -Me | 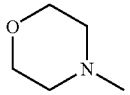 |
| 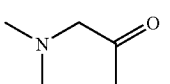 | 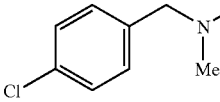 | -Me | -Me | —H | —H | -Me |  |
| 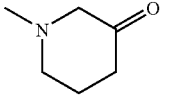 | 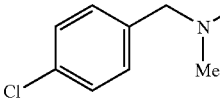 | -Me | -Me | —H | —H | -Me |  |
| 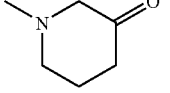 | 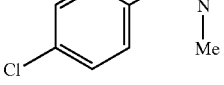 | -Me | -Me | —H | —H | -Me |  |
| 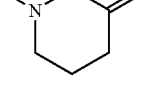 | C=O | -Me | -Me | —H | —H | -Me | 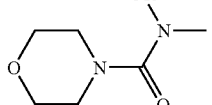 |
| 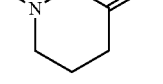 | C=O | -Me | -Me | —H | —H | -Me | 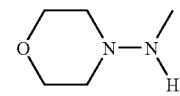 |

-continued

| Q | G=X | R¹ | R² | R³ | R⁴ | R⁵ | B |
|---|---|---|---|---|---|---|---|
| Me₂N—CO—NMe- | C=O | -Me | -Me | —H | —H | -Me | 6-chloro-N-methyl-N-(pyridin-3-ylmethyl) |
| Me-CH₂-MeCH—O— | C=O | -Me | -Me | —H | —H | -Me | 6-chloro-N-methyl-N-(pyridin-3-ylmethyl) |
| H₂C=CHMe-O— | C=O | -Me | -Me | —H | —H | -Me | 6-chloro-N-methyl-N-(pyridin-3-ylmethyl) |
| H₂C=CMe-O— | C=O | -Me | -Me | —H | —H | -Me | 6-chloro-N-methyl-N-(pyridin-3-ylmethyl) |
| HC≡C—CH₂—O— | C=O | -Me | -Me | —H | —H | -Me | 6-chloro-N-methyl-N-(pyridin-3-ylmethyl) |
| Me₂N— | C=O | -Me | -Me | —H | —H | -Me | 6-chloro-N-methyl-N-(pyridin-3-ylmethyl) |
| Et₂N— | C=O | -Me | -Me | —H | —H | -Me | 6-chloro-N-methyl-N-(pyridin-3-ylmethyl) |
| 4-methylpiperazin-1-yl | SO₂ | -Me | -Me | —H | —H | -Me | 6-chloro-N-methyl-N-(pyridin-3-ylmethyl) |
| morpholin-4-yl | SO₂ | -Me | -Me | —H | —H | -Me | 6-chloro-N-methyl-N-(pyridin-3-ylmethyl) |
| Me₂N—CO—NMe- | C=O | -Me | -Me | —H | —H | -Me | 1-(4-methylpiperazin-1-yl)-2-(morpholin-4-yl)-2-oxoethyl |
| Me-CH₂—MeCH—O— | C=O | -Me | -Me | —H | —H | -Me | 1-(4-methylpiperazin-1-yl)-2-(morpholin-4-yl)-2-oxoethyl |

-continued

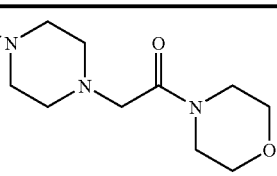

| Q | G=X | R¹ | R² | R³ | R⁴ | R⁵ | B |
|---|---|---|---|---|---|---|---|
| H₂C=CH—CHMe-O— | C=O | -Me | -Me | —H | —H | -Me | 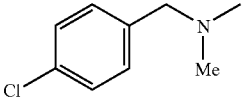 |
| Me₂N—CO—NMe- | C=O | -Me | -Me | —H | —H | -Me | —NMe-(CH₂)₂—NMe₂ |
| Me-CH₂-Me-CH—O— | C=O | -Me | -Me | —H | —H | -Me | —NMe-(CH₂)₂—NMe₂ |
| H₂C=CH—CHMe-O— | C=O | -Me | -Me | —H | —H | -Me | —NMe-(CH₂)₂—NMe₂ |
| H₂C=CMe-O— | C=O | -Me | -Me | —H | —H | -Me | —NMe-(CH₂)₂—NMe₂ |
| HC≡C—CH₂—O— | C=O | -Me | -Me | —H | —H | -Me | —NMe-(CH₂)₂—NMe₂ |
| Me₂N— | C=O | -Me | -Me | —H | —H | -Me | —NMe-(CH₂)₂—NMe₂ |
| Et₂N— | C=O | -Me | -Me | —H | —H | -Me | —NMe-(CH₂)₂—NMe₂ |
|  | 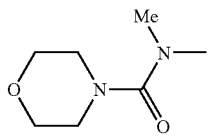 | -Me | -Me | —H | —H | -Me | —NMe-(CH₂)₂—NMe₂ |
| 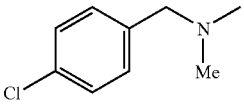 | C=O | -Me | -Me | —H | —H | -Me | —NMe-(CH₂)₂—NMe₂ |
| H₂C=CH—CH₂—O— | C=O | -Me | -Me | —H | —H | -Me | —NMe-CHMe-CH₂-Me |
| H₂C=CH—CHMe-O— | C=O | -Me | -Me | —H | —H | -Me | —NMe-CHMe-CH₂-Me |
| H₂C=CMe-O— | C=O | -Me | -Me | —H | —H | -Me | —NMe-CHMe-CH₂-Me |
| HC≡C—CH₂—O— | C=O | -Me | -Me | —H | —H | -Me | —NMe-CHMe-CH₂-Me |
| Me₂N— | C=O | -Me | -Me | —H | —H | -Me | —NMe-CHMe-CH₂-Me |
| Et₂N— | C=O | -Me | -Me | —H | —H | -Me | —NMe-CHMe-CH₂-Me |
|  | 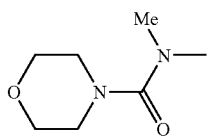 | -Me | -Me | —H | —H | -Me | —NMe-CHMe-CH₂-Me |
| 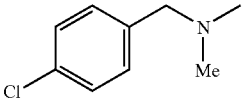 | C=O | -Me | -Me | —H | —H | -Me | —NMe-CHMe-CH₂-Me |
| H₂C=CH—CHMe-O— | C=O | -Me | -Me | —H | —H | -Me | —NMe-O-Me |
| H₂C=CMe-O— | C=O | -Me | -Me | —H | —H | -Me | —NMe-O-Me |
| HC≡C—CH₂—O— | C=O | -Me | -Me | —H | —H | -Me | —NMe-O-Me |
| Me₂N— | C=O | -Me | -Me | —H | —H | -Me | —NMe-O-Me |
| Et₂N— | C=O | -Me | -Me | —H | —H | -Me | —NMe-O-Me |
|  | | -Me | -Me | —H | —H | -Me | —NMe-O-Me |
| 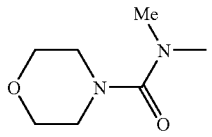 | C=O | -Me | -Me | —H | —H | -Me | —NMe-O-Me |
| H₂C=CH—CH₂—O— | C=O | -Me | -Me | —H | —H | -Me | —O—Pr |

-continued

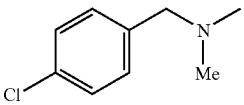

| Q | G=X | R¹ | R² | R³ | R⁴ | R⁵ | B |
|---|---|---|---|---|---|---|---|
| H₂C=CH—CHMe—O— | C=O | -Me | -Me | —H | —H | -Me | —O—Pr |
| H₂C=CMe-O— | C=O | -Me | -Me | —H | —H | -Me | —O—Pr |
| HC≡C—CH₂—O— | C=O | -Me | -Me | —H | —H | -Me | —O—Pr |
| Me₂N— | C=O | -Me | -Me | —H | —H | -Me | —O—Pr |
| Et₂N— | C=O | -Me | -Me | —H | —H | -Me | —O—Pr |
| Me₂N—CO—NMe- | C=O | -Me | -Me | —H | —H | -Me | —NMe-nPr |
| Me-CH₂-Me-CH—O— | C=O | -Me | -Me | —H | —H | -Me | —NMe-nPr |
| H₂C=CH—CH₂—O— | C=O | -Me | -Me | —H | —H | -Me | —NMe-nPr |
| H₂C=CH—CHMe—O— | C=O | -Me | -Me | —H | —H | -Me | —NMe-nPr |
| H₂C=CMe-O— | C=O | -Me | -Me | —H | —H | -Me | —NMe-nPr |
| HC≡C—CH₂—O— | C=O | -Me | -Me | —H | —H | -Me | —NMe-nPr |
| Me₂N— | C=O | -Me | -Me | —H | —H | -Me | —NMe-nPr |
| Et₂N— | C=O | -Me | -Me | —H | —H | -Me | —NMe-nPr |
| 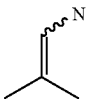 | 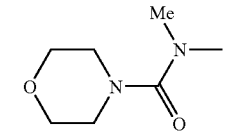 | -Me | -Me | —H | —H | -Me | —NMe-nPr |
| 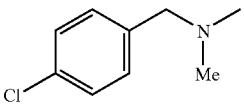 | C=O | -Me | -Me | —H | —H | -Me | —NMe-nPr |
| Me₂N—CO—NMe- | C=O | -Me | -Me | —H | —H | -Me | —NMe—CH₂C≡CH |
| Me-CH₂-MeCH—O— | C=O | -Me | -Me | —H | —H | -Me | —NMe—CH₂C≡CH |
| H₂C=CH—CH₂—O— | C=O | -Me | -Me | —H | —H | -Me | —NMe—CH₂C≡CH |
| H₂C=CH—CHMe-O— | C=O | -Me | -Me | —H | —H | -Me | —NMe—CH₂C≡CH |
| H₂C=CMe-O— | C=O | -Me | -Me | —H | —H | -Me | —NMe—CH₂C≡CH |
| HC≡C—CH₂—O— | C=O | -Me | -Me | —H | —H | -Me | —NMe—CH₂C≡CH |
| Me₂N— | C=O | -Me | -Me | —H | —H | -Me | —NMe—CH₂C≡CH |
| Et₂N— | C=O | -Me | -Me | —H | —H | -Me | —NMe—CH₂C≡CH |
| 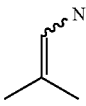 | 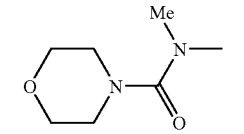 | -Me | -Me | —H | —H | -Me | —NMe—CH₂C≡CH |
| 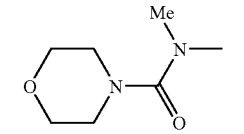 | C=O | -Me | -Me | —H | —H | -Me | —NEt-nPr |
| Me₂N—CO—NMe- | C=O | -Me | -Me | —H | —H | -Me | —NMe-(CH₂)₂—SO₂—(CH₂)₂—OH |
| Me-CH₂-Me-CH—O— | C=O | -Me | -Me | —H | —H | -Me | —NMe-(CH₂)₂—SO₂—(CH₂)₂—OH |
| H₂C=CH—CH₂—O— | C=O | -Me | -Me | —H | —H | -Me | —NMe-(CH₂)₂—SO₂—(CH₂)₂—OH |
| H₂C=CH—CHMe-O— | C=O | -Me | -Me | —H | —H | -Me | —NMe-(CH₂)₂—SO₂—(CH₂)₂—OH |
| H₂C=CMe-O— | C=O | -Me | -Me | —H | —H | -Me | —NMe-(CH₂)₂—SO₂—(CH₂)₂—OH |
| HC≡C—CH₂—O— | C=O | -Me | -Me | —H | —H | -Me | —NMe-(CH₂)₂—SO₂—(CH₂)₂—OH |
| Me₂N— | C=O | -Me | -Me | —H | —H | -Me | —NMe-(CH₂)₂—SO₂—(CH₂)₂—OH |
| Et₂N— | C=O | -Me | -Me | —H | —H | -Me | —NMe-(CH₂)₂—SO₂—(CH₂)₂—OH |

-continued

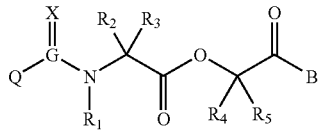

| Q | G=X | R¹ | R² | R³ | R⁴ | R⁵ | B |
|---|---|---|---|---|---|---|---|
| 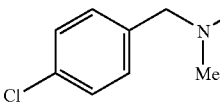 | ⟨NO₂ (isobutenyl) | -Me | -Me | —H | —H | -Me | —NMe-(CH₂)₂—SO₂—(CH₂)₂—OH |
| 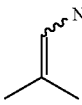 | C=O | -Me | -Me | —H | —H | -Me | —NMe-(CH₂)₂—SO₂—(CH₂)₂—OH |
| Me₂N—CO—NMe— | C=O | -Me | -Me | —H | —H | -Me | —N(CH₂—CH₂—OH)₂ |
| Me-CH₂-Me-CH—O— | C=O | -Me | -Me | —H | —H | -Me | —N(CH₂—CH₂—OH)₂ |
| H₂C=CH—CH₂—O— | C=O | -Me | -Me | —H | —H | -Me | —N(CH₂—CH₂—OH)₂ |
| H₂C=CH—CHMe-O— | C=O | -Me | -Me | —H | —H | -Me | —N(CH₂—CH₂—OH)₂ |
| H₂C=CMe-O— | C=O | -Me | -Me | —H | —H | -Me | —N(CH₂—CH₂—OH)₂ |
| HC≡C—CH₂—O— | C=O | -Me | -Me | —H | —H | -Me | —N(CH₂—CH₂—OH)₂ |
| Me₂N— | C=O | -Me | -Me | —H | —H | -Me | —N(CH₂—CH₂—OH)₂ |
| Et₂N— | C=O | -Me | -Me | —H | —H | -Me | —N(CH₂—CH₂—OH)₂ |
| 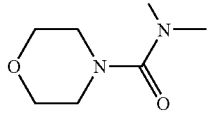 | ⟨NO₂ (isobutenyl) | -Me | -Me | —H | —H | -Me | —N(CH₂—CH₂—OH)₂ |
| 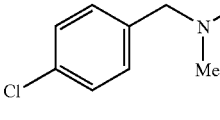 | C=O | -Me | -Me | —H | —H | -Me | —N(CH₂—CH₂—OH)₂ |
| Me₂N—CO—NMe— | C=O | -Me | -Me | —H | —H | -Me | —N[(CH₂)₂—SO₂—(CH₂)₂—OH]₂ |
| Me-CH₂-Me-CH—O— | C=O | -Me | -Me | —H | —H | -Me | —N[(CH₂)₂—SO₂—(CH₂)₂—OH]₂ |
| H₂C=CH—CH₂—O— | C=O | -Me | -Me | —H | —H | -Me | —N[(CH₂)₂—SO₂—(CH₂)₂—OH]₂ |
| H₂C=CH—CHMe-O— | C=O | -Me | -Me | —H | —H | -Me | —N[(CH₂)₂—SO₂—(CH₂)₂—OH]₂ |
| H₂C=CMe-O— | C=O | -Me | -Me | —H | —H | -Me | —N[(CH₂)₂—SO₂—(CH₂)₂—OH]₂ |
| HC≡C—CH₂—O— | C=O | -Me | -Me | —H | —H | -Me | —N[(CH₂)₂—SO₂—(CH₂)₂—OH]₂ |
| Me₂N— | C=O | -Me | -Me | —H | —H | -Me | —N[(CH₂)₂—SO₂—(CH₂)₂—OH]₂ |
| Et₂N— | C=O | -Me | -Me | —H | —H | -Me | —N[(CH₂)₂—SO₂—(CH₂)₂—OH]₂ |
| 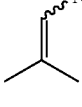 | ⟨NO₂ (isobutenyl) | -Me | -Me | —H | —H | -Me | —N[(CH₂)₂—SO₂—(CH₂)₂—OH]₂ |
| 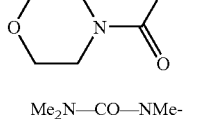 | C=O | -Me | -Me | —H | —H | -Me | —N[(CH₂)₂—SO₂—(CH₂)₂—OH]₂ |

-continued
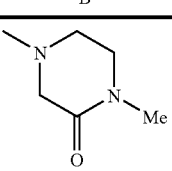
| Q | G=X | R¹ | R² | R³ | R⁴ | R⁵ | B |
|---|---|---|---|---|---|---|---|
| Me₂N—CO—NMe- | C=O | -Me | -Me | —H | —H | -Me | 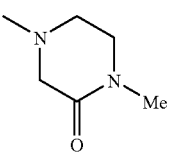 |
| Me-CH₂-Me-CH—O— | C=O | -Me | -Me | —H | —H | -Me | 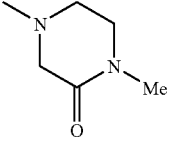 |
| H₂C=CH—CH₂—O— | C=O | -Me | -Me | —H | —H | -Me | 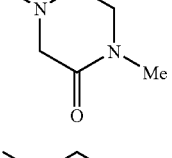 |
| H₂C=CH—CHMe-O— | C=O | -Me | -Me | —H | —H | -Me | 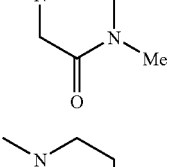 |
| H₂C=CMe-O— | C=O | -Me | -Me | —H | —H | -Me | 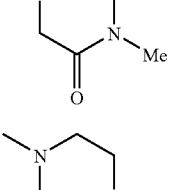 |
| HC≡C—CH₂—O— | C=O | -Me | -Me | —H | —H | -Me | 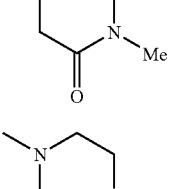 |
| Me₂N— | C=O | -Me | -Me | —H | —H | -Me | 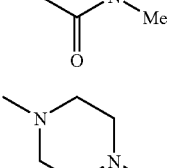 |
| Et₂N— | C=O | -Me | -Me | —H | —H | -Me | 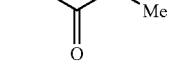 |
| 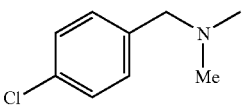 | 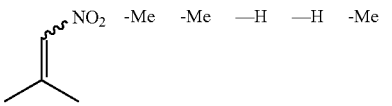 | -Me | -Me | —H | —H | -Me | |

-continued

| Q | G=X | R¹ | R² | R³ | R⁴ | R⁵ | B |
|---|---|---|---|---|---|---|---|
| morpholine-N-C(=O)-N(Me)- | C=O | -Me | -Me | —H | —H | -Me | 4-methyl-1-methyl-3-oxopiperazinyl |
| Me₂N—CO—NMe- | C=O | -Me | -Me | —H | —H | -Me | 4-methyl-1-methyl-3,5-dioxopiperazinyl |
| Me-CH₂-Me-CH—O— | C=O | -Me | -Me | —H | —H | -Me | 4-methyl-1-methyl-3,5-dioxopiperazinyl |
| H₂C=CH—CH₂—O— | C=O | -Me | -Me | —H | —H | -Me | 4-methyl-1-methyl-3,5-dioxopiperazinyl |
| H₂C=CH—CHMe-O— | C=O | -Me | -Me | —H | —H | -Me | 4-methyl-1-methyl-3,5-dioxopiperazinyl |
| H₂C=CMe-O— | C=O | -Me | -Me | —H | —H | -Me | 4-methyl-1-methyl-3,5-dioxopiperazinyl |
| HC≡C—CH₂—O— | C=O | -Me | -Me | —H | —H | -Me | 4-methyl-1-methyl-3,5-dioxopiperazinyl |
| Me₂N— | C=O | -Me | -Me | —H | —H | -Me | 4-methyl-1-methyl-3,5-dioxopiperazinyl |

-continued
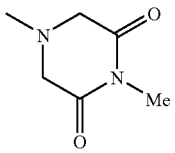
| Q | G=X | R¹ | R² | R³ | R⁴ | R⁵ | B |
|---|---|---|---|---|---|---|---|
| Et₂N— | C=O | -Me | -Me | —H | —H | -Me | 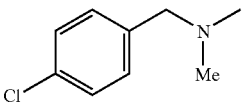 |
| 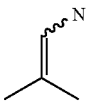 | 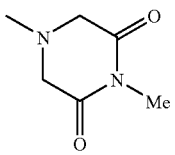 | -Me | -Me | —H | —H | -Me | 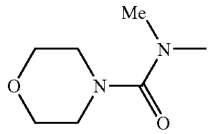 |
| 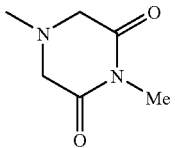 | C=O | -Me | -Me | —H | —H | -Me | 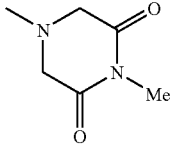 |
| Me₂N—CO—NMe- | C=O | -Me | -Me | —H | —H | -Me | 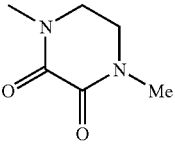 |
| Me₂N—CO—NMe- | C=O | -Me | -Me | —H | —H | -Me | 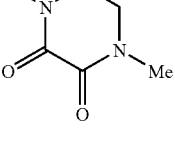 |
| Me-CH₂-Me-CH—O— | C=O | -Me | -Me | —H | —H | -Me | 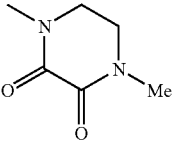 |
| H₂C=CH—CH₂—O— | | -Me | -Me | —H | —H | -Me | 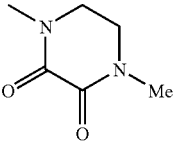 |
| H₂C=CH—CHMe-O— | C=O | -Me | -Me | —H | —H | -Me | |

-continued
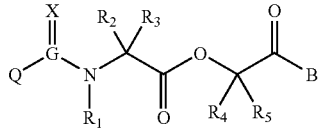
| Q | G=X | R¹ | R² | R³ | R⁴ | R⁵ | B |
|---|---|---|---|---|---|---|---|
| H₂C=CMe-O— | C=O | -Me | -Me | —H | —H | -Me | 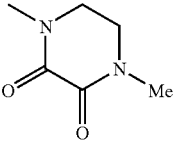 |
| HC≡C—CH₂—O— | C=O | -Me | -Me | —H | —H | -Me | 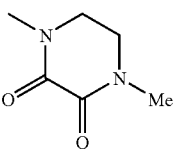 |
| Me₂N— | C=O | -Me | -Me | —H | —H | -Me | 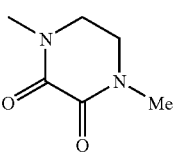 |
| Et₂N— | C=O | -Me | -Me | —H | —H | -Me | 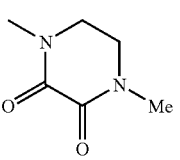 |
| 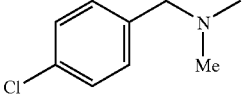 |  | -Me | -Me | —H | —H | -Me | 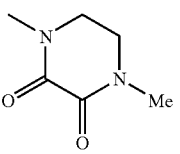 |
| 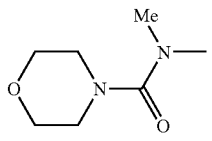 | C=O | -Me | -Me | —H | —H | -Me | 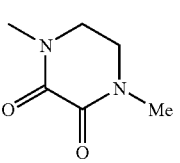 |
| Me₂N—CO—NMe- | C=O | -Me | -Me | —H | —H | -Me | 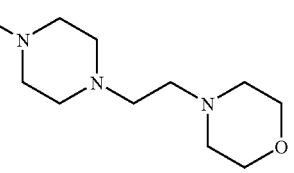 |
| Me-CH₂-Me-CH—O— | C=O | -Me | -Me | —H | —H | -Me | 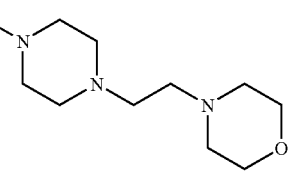 |

-continued
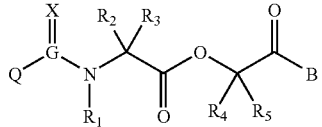
| Q | G=X | R¹ | R² | R³ | R⁴ | R⁵ | B |
|---|---|---|---|---|---|---|---|
| H$_2$C=CH—CH$_2$—O— | =Me | -Me | -Me | —H | —H | -Me | 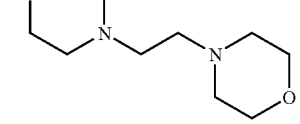 |
| H$_2$C=CH—CHMe-O— | C=O | -Me | -Me | —H | —H | -Me | 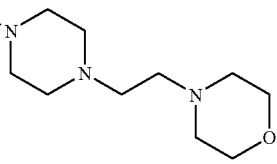 |
| H$_2$C=CMe-O— | C=O | -Me | -Me | —H | —H | -Me | 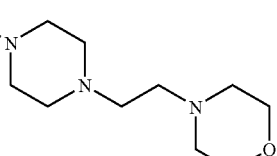 |
| HC≡C—CH$_2$—O— | C=O | -Me | -Me | —H | —H | -Me | 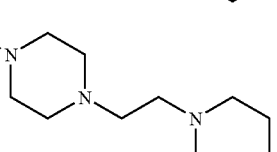 |
| Me$_2$N— | C=O | -Me | -Me | —H | —H | -Me | 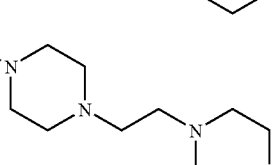 |
| 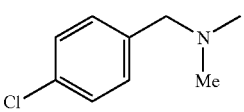 | 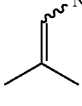 | -Me | -Me | —H | —H | -Me | 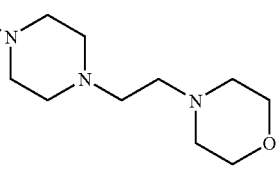 |
| 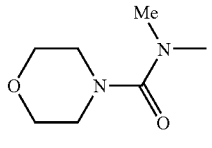 | C=O | -Me | -Me | —H | —H | -Me | 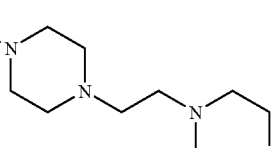 |
| Me$_2$N—CO—NMe- | C=O | -Me | -Me | —H | —H | -Me | 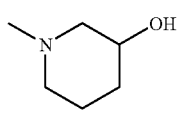 |
| Me-CH$_2$-Me-CH—O— | C=O | -Me | -Me | —H | —H | -Me | 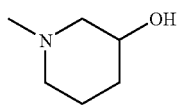 |

-continued
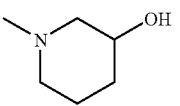
| Q | G=X | R¹ | R² | R³ | R⁴ | R⁵ | B |
|---|---|---|---|---|---|---|---|
| H₂C=CH—CHMe-O— | C=O | -Me | -Me | —H | —H | -Me | 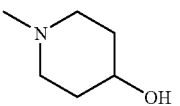 |
| Me₂N—CO—NMe- | C=O | -Me | -Me | —H | —H | -Me | 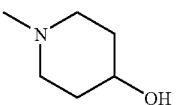 |
| Me-CH₂-Me-CH—O— | C=O | -Me | -Me | —H | —H | -Me | 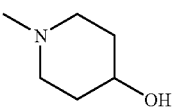 |
| H₂C=CH—CHMe-O— | C=O | -Me | -Me | —H | —H | -Me | 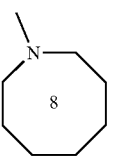 |
| Me₂N—CO—NMe- | C=O | -Me | -Me | —H | —H | -Me | 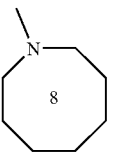 |
| Me-CH₂-Me-CH—O— | C=O | -Me | -Me | —H | —H | -Me | 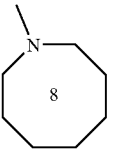 |
| H₂C=CH—CHMe-O— | C=O | -Me | -Me | —H | —H | -Me | 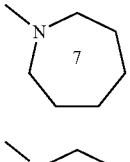 |
| Me₂N—CO—NMe- | C=O | -Me | -Me | —H | —H | -Me | 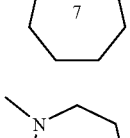 |
| Me-CH₂-Me-CH—O— | C=O | -Me | -Me | —H | —H | -Me | 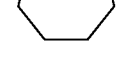 |
| H₂C=CH—CHMe-O— | C=O | -Me | -Me | —H | —H | -Me | |

-continued

| Q | G=X | R¹ | R² | R³ | R⁴ | R⁵ | B |
|---|---|---|---|---|---|---|---|
| Me₂N—CO—NMe- | C=O | -Me | -Me | —H | —H | -Me | methyl-morpholinyl-hydrazinyl |
| Me-CH₂-Me-CH—O— | C=O | -Me | -Me | —H | —H | -Me | methyl-morpholinyl-hydrazinyl |
| H₂C=CH—CH₂—O— | | -Me | -Me | —H | —H | -Me | methyl-morpholinyl-hydrazinyl |
| H₂C=CH—CHMe-O— | C=O | -Me | -Me | —H | —H | -Me | methyl-morpholinyl-hydrazinyl |
| H₂C=CMe-O— | C=O | -Me | -Me | —H | —H | -Me | methyl-morpholinyl-hydrazinyl |
| HC≡C—CH₂—O— | C=O | -Me | -Me | —H | —H | -Me | methyl-morpholinyl-hydrazinyl |
| Me₂N— | C=O | -Me | -Me | —H | —H | -Me | methyl-morpholinyl-hydrazinyl |
| 4-Cl-C₆H₄-CH₂-N(Me)- (with NMe₂) | =C(Me)-CH=NO₂ | -Me | -Me | —H | —H | -Me | methyl-morpholinyl-hydrazinyl |
| morpholine-N-C(=O)-N(Me)- | C=O | -Me | -Me | —H | —H | -Me | methyl-morpholinyl-hydrazinyl |

-continued
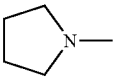
| Q | G=X | R¹ | R² | R³ | R⁴ | R⁵ | B |
|---|---|---|---|---|---|---|---|
| 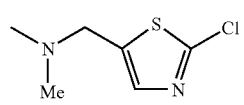 | SO₂ | -Me | -Me | —H | —H | -Me | —O-Me |
| Et₂N | SO₂ | -Me | -Me | —H | —H | -Me | —O-Me |
| Me₂N—CO—NMe- | C=O | -Me | -Me | —H | —H | -Me | 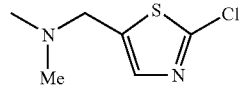 |
| Me-CH₂-Me-CH—O— | C=O | -Me | -Me | —H | —H | -Me | 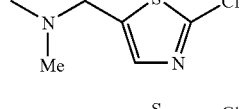 |
| H₂C=CH—CHMe-O— | C=O | -Me | -Me | —H | —H | -Me | 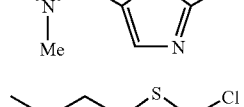 |
| H₂C=CMe-O— | C=O | -Me | -Me | —H | —H | -Me | 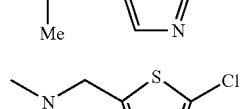 |
| HC≡C—CH₂—O— | C=O | -Me | -Me | —H | —H | -Me | 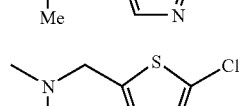 |
| Me₂N— | C=O | -Me | -Me | —H | —H | -Me | 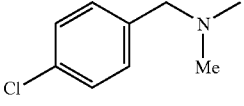 |
| 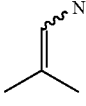 | 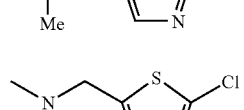 | -Me | -Me | —H | —H | -Me | 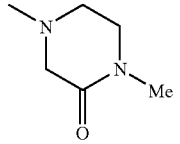 |
| 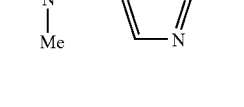 | C=O | -Me | -Me | —H | —H | -Me | 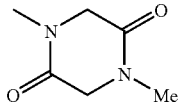 |
| Me₂N—CO—NMe- | C=O | -Me | -Me | —H | —H | -Me | 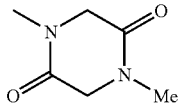 |
| Me-CH₂-Me-CH—O— | C=O | -Me | -Me | —H | —H | -Me | 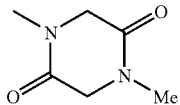 |
| H₂C=CH—CHMe-O— | C=O | -Me | -Me | —H | —H | -Me | 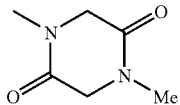 |

-continued
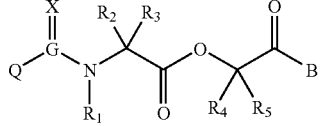
| Q | G=X | R¹ | R² | R³ | R⁴ | R⁵ | B |
|---|---|---|---|---|---|---|---|
| H₂C=CMe-O— | C=O | -Me | -Me | —H | —H | -Me | 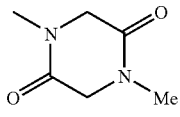 |
| HC≡C—CH₂—O— | C=O | -Me | -Me | —H | —H | -Me | 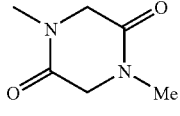 |
| Me₂N— | C=O | -Me | -Me | —H | —H | -Me | 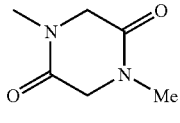 |
| 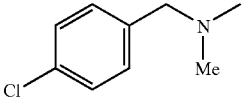 | 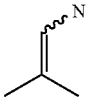 | -Me | -Me | —H | —H | -Me | 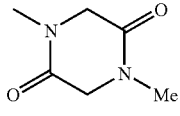 |
| Et₂N—CO—NMe- | C=O | -Me | -Me | —H | —H | -Me | 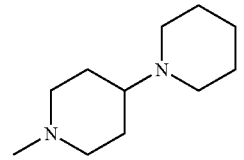 |
| Me-CH₂-Me-CH—O— | C=O | -Me | -Me | —H | —H | -Me | 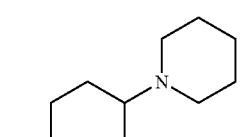 |
| H₂C=CH—CHMe-O— | C=O | -Me | -Me | —H | —H | -Me | 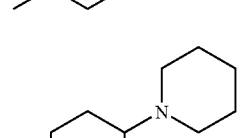 |
| H₂C=CMe-O— | C=O | -Me | -Me | —H | —H | -Me | 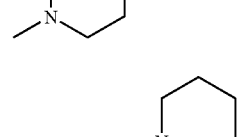 |
| HC≡C—CH₂—O— | C=O | -Me | -Me | —H | —H | -Me | 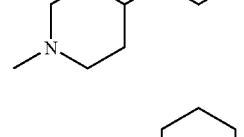 |

-continued

| Q | G=X | R¹ | R² | R³ | R⁴ | R⁵ | B |
|---|---|---|---|---|---|---|---|
| Me₂N— | C=O | -Me | -Me | —H | —H | -Me | 1-methyl-4-(piperidin-1-yl)piperidine |
| Me₂N— | SO₂ | -Me | -Me | —H | —H | -Me | 1-methyl-4-(piperidin-1-yl)piperidine |
| Et₂N—CO—NMe- | C=O | -Me | -Me | —H | —H | -Me | tert-butyl (1-methylpiperidin-4-yl)carbamate |
| Me₂N—CO—NMe- | C=O | -Me | -Me | —H | —H | -Me | tert-butyl (1-methylpiperidin-4-yl)carbamate |
| Me-CH₂-MeCH—O— | C=O | -Me | -Me | —H | —H | -Me | tert-butyl (1-methylpiperidin-4-yl)carbamate |
| H₂C=CH—CHMe-O— | C=O | -Me | -Me | —H | —H | -Me | tert-butyl (1-methylpiperidin-4-yl)carbamate |
| H₂C=CMe-O— | C=O | -Me | -Me | —H | —H | -Me | tert-butyl (1-methylpiperidin-4-yl)carbamate |

-continued
| Q | G=X | R¹ | R² | R³ | R⁴ | R⁵ | B |
|---|---|---|---|---|---|---|---|
| HC≡C—CH₂—O— | C=O | -Me | -Me | —H | —H | -Me | 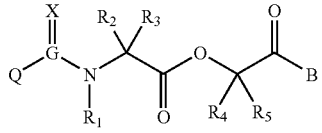 |
| Me₂N— | C=O | -Me | -Me | —H | —H | -Me | 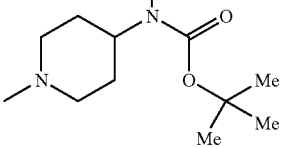 |
| Me₂N— | SO₂ | -Me | -Me | —H | —H | -Me | 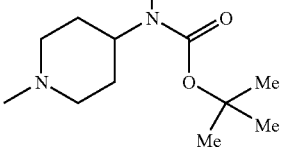 |
| Me₂N—CO—NMe- | C=O | -Me | -Me | —H | —H | -Me | 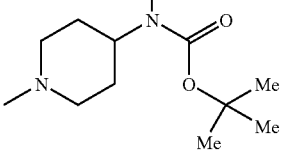 |
| Et₂N—CO—NMe- | C=O | -Me | -Me | —H | —H | -Me | 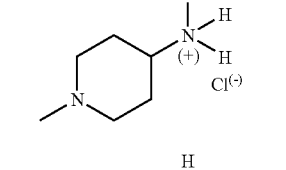 |
| Me-CH₂-Me-CH—O— | C=O | -Me | -Me | —H | —H | -Me | 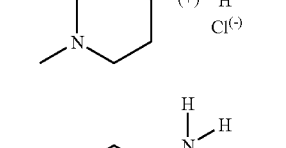 |
| H₂C=CH—CHMe-O— | C=O | -Me | -Me | —H | —H | -Me | 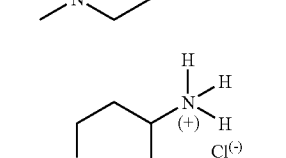 |
| H₂C=CMe-O— | C=O | -Me | -Me | —H | —H | -Me | 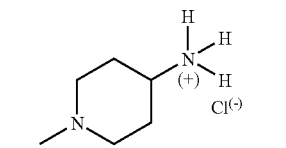 |

-continued

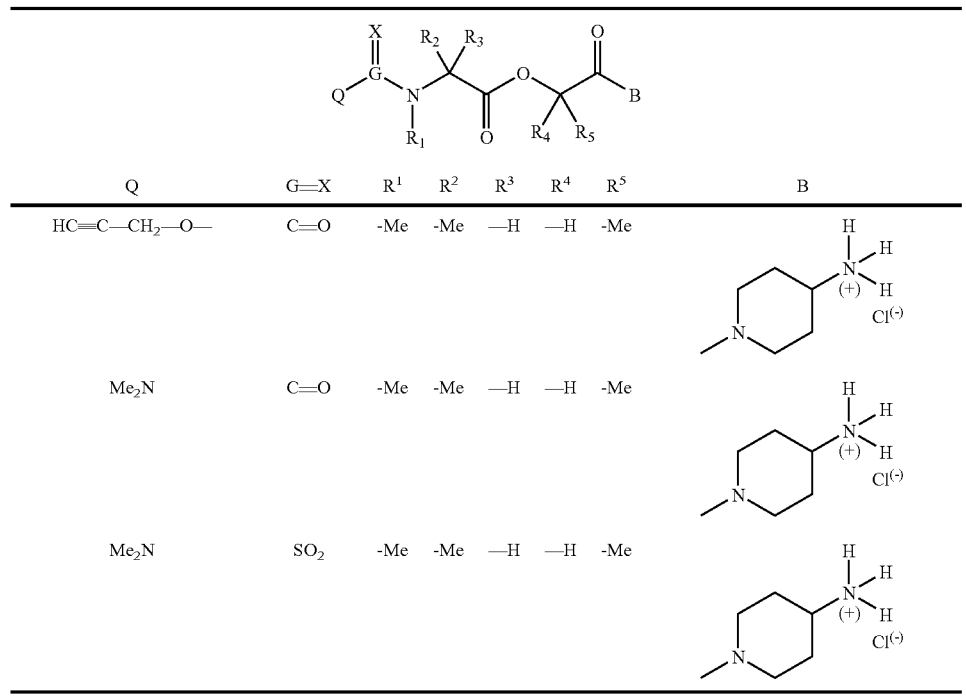

| Q | G=X | R¹ | R² | R³ | R⁴ | R⁵ | B |
|---|---|---|---|---|---|---|---|
| HC≡C—CH₂—O— | C=O | -Me | -Me | —H | —H | -Me | 4-amino-1-methylpiperidinium chloride |
| Me₂N | C=O | -Me | -Me | —H | —H | -Me | 4-amino-1-methylpiperidinium chloride |
| Me₂N | SO₂ | -Me | -Me | —H | —H | -Me | 4-amino-1-methylpiperidinium chloride |

Abbreviations: Me: -methyl; Et: ethyl; Pr; -propyl; Bu: -butyl; i-, s- and t-: iso-, secondary- and tertiary If, in process 3a for the preparation of the new didepsipeptides (Ia), as compounds of the general formula (II) N-methyl-N-trimethylallophanoyl-L-alanine and as compounds of the general formula (III) isobutyl D-lactate are employed, the process can be represented by the following reaction scheme:

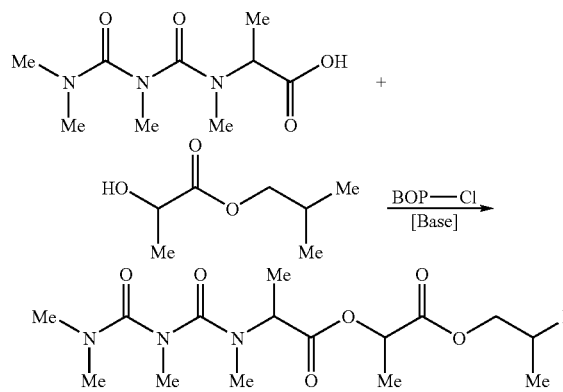

Formula (II) provides a general definition of the N-terminal-acylated N-alkyl-amino acids needed as starting substances for carrying out process 3a according to the invention. In this formula, $R^1$, $R^2$, $R^3$, G, Q and X preferably represent those radicals which have already been mentioned as preferred for these substituents in connection with the description of the substances of the general formula (II) according to the invention.

The N-acylated N-alkyl-amino acids of the general formula (II) used as starting materials are known in some cases (cf. for example: N-methylamino acids: R. Bowmann et al. J. Chem. Soc. (1950) p. 1346, J. R. McDermott et al. Can. J. Chem. 51 (1973) p. 1915; H. Wurziger et al. Kontakte (Merck, Darmstadt) 3 (1987) p. 8) or can be obtained by the processes described there.

Formula (III) provides a general definition of the carboxylic acid derivatives additionally to be used as starting substances for carrying out process 3a according to the invention. In the formula (III), $R^4$, $R^5$, B and Z have the meaning which have already been mentioned as preferred for these substituents in connection with the description of the substances of the general formula (Ia) according to the invention.

The compounds of the formula (III) are generally known compounds of organic chemistry or can be obtained by methods known from the literature (e.g.: 2-hydroxycarboxylic acid derivatives: cf. Houben-Weyl, Methoden der organischen Chermie, Volume VIII; 2-halogenocarboxylic acid derivatives: S. M. Birnbaum et al. J. Amer. Chem. Soc. 76 (1954) p. 6054, C. S. Rondestvedt, Jr. et al. Org. Reactions 11 (1960) p. 189 [Review]) or can be obtained by the processes described there.

The reaction of the N-acylated N-alkylamino acids (II) with 2-hydroxycarboxylic acid derivatives (III) is preferably carried out using diluents in the presence of coupling reagents and in the presence of a basic reaction auxiliary.

The coupling reagents used for carrying out process 3a are all those which are suitable for the preparation of an amide bond (cf. for example: Houben-Weyl, Methoden der organischen Chemie [Methods of Organic Chemistry], Volume 15/2; Bodanszky et al., Peptide Synthesis 2nd ed. (Wiley & Sons, New York 1976) or Gross, Meienhofer, The Peptides: Analysis Synthesis, Biology (Academic Press, New York 1979). The following methods are preferably used: active ester method using pentachlorophenol (Pcp) and pentafluorophenol (Pfp), N-hydroxysuccinimide, N-hydroxy-5-norbornene-2,3-dicarbox-amide (HONB), 1-hydroxy-benzotriazole (HOBt) or 3-hydroxy-4-oxo-3,4-dihydro1,2,3-benzotriazine as the alcohol component, coupling using carbodiimides such as dicyclohexyl-carbodiimide (DCC) according to the DCC additive process, or using n-propanephos-phonic anhydride (PPA) and mixed anhydride method using pivaloyl chloride, ethyl chloroformate (EEDQ) and isobutyl chloroformate (IIDQ) or coupling using phosphonium reagents, such as benzotriazol-1-yl-oxy-tris(dimethylamino-phosphonium) hexafluorophosphate (BOP), bis(2-oxo-3-oxazolidinyl) phosphonium acid chloride (BOP-Cl), or using phosphonic acid ester reagents, such as diethyl cyanophosphonate (DEPC) and diphenylphosphoryl azide (DPPA) or uronium reagents, such as 2-(1H-benzotrinazol-1-yl)-1,1,3,3-tetramethyluronium tetrafluoro borate (TBTU).

The preferred coupling is using phosphonium reagents such as bis(2-oxo-3-oxazolidinyl)-phosphonium acid chloride (BOP-Cl), benzotriazol-1-yl-oxy-tris(dimethylamino-phosphonium) hexafluorophosphate (BOP) and phosphonic acid ester reagents, such as diethyl cyanophosphonate (DEPC) or diphenylphosphoryl azide (DPPA).

Basic reaction auxiliaries which can be employed for carrying out process 3a according to the invention are all suitable acid-binding agents, such as amines, in particular tertiary amines, and alkali metal and alkaline earth metal compounds.

Examples which may therefore be mentioned are the hydroxides, oxides and carbonates of lithium, sodium, potassium, magnesium, calcium and barium, and further other basic compounds such as amidine bases or guanidine bases such as 7-methyl-1,5,7-triazabi-cyclo(4.4.0)dec-5-ene (MTBD); diazabicyclo(4.3.0)nonene (DBN), diazabicyclo (2.2.2)-octane (DABCO), 1,8-diaza-bicyclo(5.4.0)undecene (DBU) cyclohexyl-tetrabutylguanidine (CyTGB), cyclohexyltetramethylguanidine (CyTMG), N,N,N,N-tetramethyl-1,8-naphthalenediamine, pentamethylpiperidine, tertiary amines such as triethylamine, trimethylamine, tribenzylamine, triisopropylamine, tributylamine, tribenzylamine, tricyclohexylamine, triamylamine, trihexylamine, N,N-dimethyl-aniline, N,N-dimethyl-toluidine, N,N-dimethyl-p-aminopyridine, N-methyl-pyrrolidine, N-methyl-piperidine, N-methyl-imidazole, N-methyl-pyrrole, N-methyl-morpholine, N-methyl-hexamethyleneimine, pyridine, 4-pyrrolidinopyridine, 4-dimethylamino-pyridine, quinoline, α-picoline, α-picoline, isoquinoline, pyrimidine, acridine, N,N,N',N'-tetramethylenediamine, N,N',N'-tetraethylenediamine, quinoxaline, N-propyl-diisopropylamine, N-ethyl-diisopropylamine, N,N'-dimethylcyclohexylamine, 2,6-lutidine, 2,4-lutidine or triethylenediamine.

Those preferably used are tertiary amines, in particular trialkylamines such as triethylamine, N,N-diisopropylethylamine, N-propyl-diisopropylamine, N,N'-dimethyl-cyclohexylamine or N-methylmorpholine.

In general, it is advantageous to carry out process 3a according to the invention in the presence of diluents. Diluents are advantageously employed in an amount such that the reaction mixture remains readily stirrable during the whole process. Suitable diluents for carrying out process 3a according to the invention are all inert organic solvents.

Examples which may be mentioned are: halogenohydrocarbons, in particular chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, dichlorobenzene, chlorotoluene, trichlorobenzene; alcohols such as methanol, ethanol, isopropanol, butanol; ethers such as ethyl propyl ether, methyl tert-butyl ether, n-butyl ether, anisole, phenetole, cyclohexyl methyl ether, dimethyl ether, diethyl ether, dipropyl esther, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide; amines such as trimethylamine, triethylamine, tripropylamine, tributylamine, N-methyl-morpholine, pyridine and tetramethylenediamine, nitrohydrocarbons such as nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chloro-benzonitrile, and compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons such as pentane, hexane, heptane, octane, nonane and industrial hydrocarbons, for example so-called white spirits having components with boiling points in the range, for example, 40 to 250° C., cymene, benzine fractions within a boiling point interval from 70° C. to 190° C., cyclohexane, methylcyclohexane, petroleum ether, ligroin, octane, benzene, toluene, xylene; esters such as methyl acetate, ethyl acetate, butyl acetate, isobutyl acetate, and also dimethyl carbonate, dibutyl carbonate, ethylene carbonate; amides such as hexamethylenephosphoramide, formamide, N-methylformamide, N,N-di-methylformamide, N,N-dipropylformamide, N,N-dibutylformamide, N-methyl-pyrrolidone, N-methyl-caprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine; ketones such as acetone, methyl ethyl ketone, methyl butyl ketone.

Of course, mixtures of the solvents and diluents mentioned can also be employed in the process according to the invention.

Preferred diluents are halogenohydrocarbons, in particular chlorohydrocarbons, such as methylene chloride or 1,2-dichloroethane and mixtures of these with other diluents mentioned.

Process 3a is in general carried out by reacting compounds of the formula (II) with compounds of the general formula (III) in one of the given diluents in the presence of one of the given coupling reagents and in the presence of one of the given basic auxiliaries. The reaction time is 4 to 72 hours. The reaction is carried out at temperatures between −10° C. and +120° C., preferably between −5° C. and +50° C., particularly preferably at 0° C. to room temperature. It is carried out under normal pressure.

For carrying out process 3a according to the invention, in general 1.0 to 3.0 mol, preferably 1.0 to 1.5 mol, of coupling reagent are employed per mole of N-acylated N-alkylamino acid of the formula (II).

After reaction is complete, the reaction solution is washed, and the organic phase is separated off, dried and concentrated in vacuo. The products formed can be purified in a customary manner by recrystallization, vacuum distillation or column chromatography (cf. also the Preparation Examples).

Alternatively, the didepsipeptides according to the invention can also be prepared according to classical processes, for example that as is described by H.-G. Lerchen and H. Kunz (Tetrahedron Lett. 26 (43) (1985) p. 5257-5260; 28 (17) (1987) p. 1873-1876) utilizing the esterification method according to B. F. Gisin (Helv. Chim. Acta 56 (1973) p. 1476).

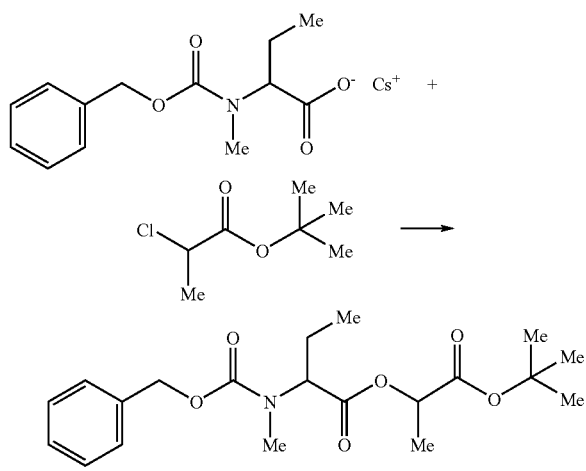

If, in process 3b for the preparation of the new didepsipeptides (Ia) as compounds of the general formula (Ib) methyl N-methyl-L-alanyl-D-lactate and as compounds of the general formula (IV) trimethylallophanoyl chloride are employed, the process can be represented by the following reaction scheme:

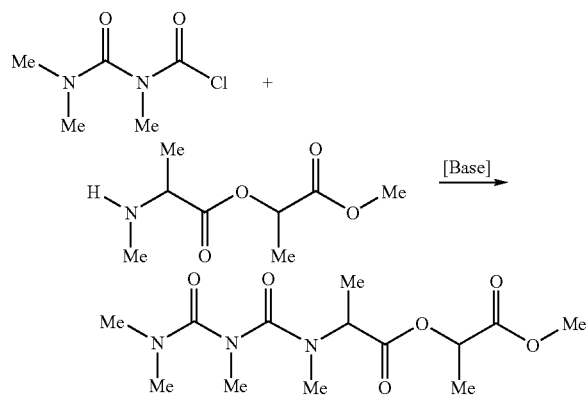

Formula (Ib) provides a general definition of the N-terminal-deblocked didepsipeptides needed as starting substances for carrying out process 3b according to the invention. In this formula, $R^1$, $R^2$, $R^3$, $R^4$, $R^5$ and B preferably represent those radicals which have already been mentioned as preferred for these substituents in connection with the description of the substances of the general formula (Ia) according to the invention.

The N-terminal-deblocked didepsipeptides of the general formula (Ib) used as starting materials are known in some cases (cf. DE-OS [German Published Specification] 4 341 991, DE-OS [German Published Specification] 4 341 992, DE-OS [German Published Specification] 4 341 992) or can be obtained from N-terminal-protected didepsipeptides by the processes described there.

Formula (IV) provides a general definition of the compounds additionally to be used as starting substances for carrying out process 3b according to the invention.

In the formula (IV), G, X, Y, and W have the meaning which have already been mentioned as preferred for these substituents in connection with the description of the substances of the general formula (Ia) according to the invention.

The compounds of the formula (IV) are generally known compounds of organic chemistry or can be obtained by methods known from the literature (e.g.: per-substituted allophanoyl halides: DE-OS [German Published Specification] 2 008 116; carbamoyl chlorides: Liebigs Ann. 299, p. 85; carbamates: Houben-Weyl, Methoden der organischen Chemie, Volume E 4).

The reaction of the compounds (Ib) with (IV) is preferably carried out using diluents in the presence of a basic reaction auxiliary.

Diluents used for carrying out process 3b according to the invention are the inert, aprotic solvents mentioned in process 3a, e.g. dioxane, acetonitrile or tetrahydrofuran but also halogenohydrocarbons, in particular chlorohydrocarbons, such as methylene chloride.

Basic reaction auxiliaries which can be used for carrying out process 3b according to the invention are all acid-binding agents mentioned in process 3a, but preferably tertiary amines, in particular trialkylamines such as triethylamine, N,N-diisopropylethylamine N-propyl-diisopropylamine, N,N'-dimethyl-cyclohexylamine or N-methylmorpholine.

Process 3b is carried out by reacting compounds of the general formula (Ib) in the presence of a basic reaction auxiliary with compounds of the general formula (IV) in one of the given diluents.

The reaction time is 4 to 72 hours. The reaction is carried out at temperatures between −10° C. and +150° C., preferably between −5° C. and +80° C., particularly preferably at 0° C. to room temperature. It is carried out under normal pressure. For carrying out process 3b according to the invention, in general 1.0 to 3.0 mol, preferably 1.0 to 1.5 mol, of acylating agent are employed per mole of N-alkylamino acid of the formula (Ib).

After reaction is complete, the reaction solution is washed, and the organic phase is separated off, dried and concentrated in vacuo. The products formed can be purified in a customary manner by recrystallization, vacuum distillation or column chromatography (cf. also the Preparation Examples).

If, in process 3c for the preparation of the new didepsipeptides (Ia), as compounds of the general formula (Ib) tert-butyl N-methyl-L-alanyl-D-lactate and as compounds of the general formula (V) trichloroacetyl isocyanate are employed, the process can be represented by the following reaction scheme:

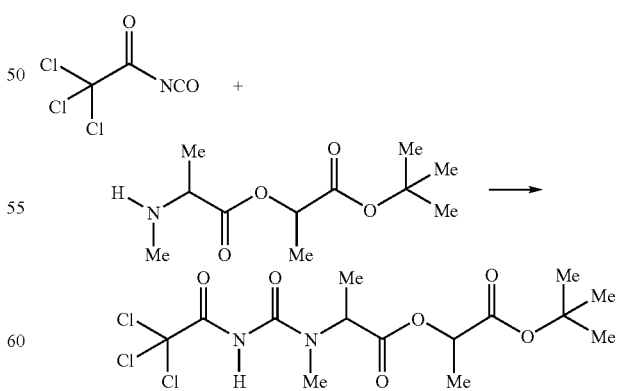

Formula (Ib) provides a general definition of the N-terminal-deblocked didepsipeptides needed as starting substances for carrying out process 3c according to the invention. In this formula, $R^1$, $R^2$, $R^3$, $R^4$, $R^5$ and B preferably represent those radicals which have already been mentioned as preferred for these substituents in connection with the description of the substances of the general formula (Ia) according to the invention.

The N-terminal-deblocked didepsipeptides of the general formula (Ib) used as starting materials are known in some cases (cf. DE-OS [German Published Specification] 4 341 991, DE-OS [German Published Specification] 4 341 992, DE-OS [German Published Specification] 4 341 992) or can be obtained from N-terminal-protected didepsipeptides by the processes described there.

Formulae (V) and (VI) provide a general definition of the compounds additionally to be used as starting substances for carrying out process 3c according to the invention.

In the formula (VI), $R^8$, Y, $G^1$, $X^1$ and X have the meaning which has already been mentioned as preferred for these substituents in connection with the description of the substances of the general formula (Ia) according to the invention.

The compounds of the formula (VI) are generally known compounds of organic chemistry and can be obtained commercially in some cases or by methods known from the literature (Houben-Weyl, Methoden der organischen Chemie, [Methods of organic chemistry] Volume E4).

The reaction of the compounds (Ib) with (VI) by process 3c according to the invention is preferably carried out in the presence of diluents, if appropriate in the presence of a basic reaction auxiliary.

Fundamentally, it can be carried out under normal pressure, but also at elevated or reduced pressure. The process is preferably carried out at normal pressure or at pressures of up to 15 bar. At higher temperatures, it is advantageous to work at elevated pressure, if appropriate even above 15 bar.

After reaction is complete, the reaction mixture is worked up by generally customary methods (cf. also the Preparation Examples).

Processes for the preparation of organic carbamates from an amine having a basic reaction, carbon dioxide and an alkylating agent in the presence of basic alkali metal, alkaline earth metal or ammonium salts are known (cf. EP-OS [European Published Specification] 511 948, EP-OS [European Published Specification] 628 542 and literature cited there).

It has now been found that even the weakly basic, N-terminal-deblocked didepsipeptides of the formula (Ib) according to the invention, as amino compounds, react with carbon dioxide and an alkylating agent in the presence of metal carbamates to give carbamates of the general formula (Ia).

If, in process 3d for the preparation of the new didepsipeptides (Ia), as compounds of the general formula (Ib) tert-butyl N-methyl-L-alanyl-D-lactate, carbon dioxide, potassium carbonate and as compounds of the general formula (IX) butyl bromide are employed, the process can be represented by the following reaction scheme:

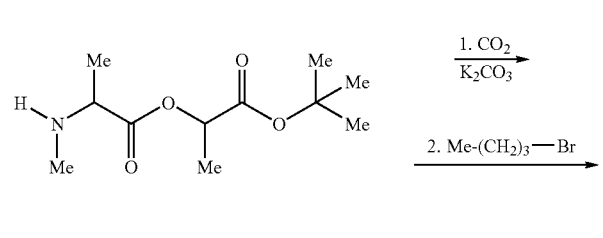
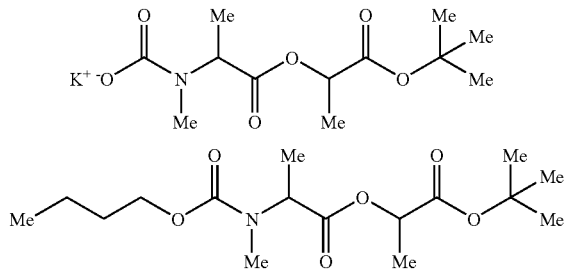

Diluents used for carrying out process 3c according to the invention are the solvents mentioned in process 3a, e.g. nitriles such as acetonitrile, propionitrile, butyronitrile, in particular acetonitrile, and ethers such as ethyl propyl ether, n-butyl ether, diethyl ether, dipropyl esther, diisopropyl ether, di-n-butyl ether, diisobutyl ether, diisoamyl ether, tetrahydrofuran, dioxane, in particular terahydrofuran and dioxane.

Process 3c can also be carried out in the presence of basic reaction auxiliaries. Those basic reaction auxiliaries which can use for carrying out process 3c according to the invention are all acid-binding agents mentioned in process 3a, but preferably tertiary amines, in particular trialkylamines such as triethylamine, N,N-diisopropylethylamine or N-methylmorpholine, and amidine bases or guanidine bases such as diazabicyclo-(4.3.0)nonene (DBN), diazabicyclo (2.2.2)-octane (DABCO), 1,8-diazabicyclo(5.4.0)-undecene (DBU), in particular 1,8-diazabicyclo(5.4.0)-undecene (DBU), use.

Process 3c is carried out by combining compounds of the general formula (Ib) with equimolar amounts of a compound of the formula (VI) in one of the diluents given above, if appropriate in the presence of a basic reaction auxiliary. The reaction time is 1 to 72 hours. The reaction is carried out at temperatures between −50° C. to +200° C., preferably in a temperature range between −20° C. and +150° C., in particular in a temperature range between −10° C. and +120° C.

Preferably, in in process 3d the didepsipeptides of the formula (Ib) are employed in which the radicals $R^1$, $R^2$, $R^3$, $R^4$, $R^5$ and B have the preferred and particularly preferred meanings in the case of the compounds of the general formula (Ia).

The N-terminal-deblocked didepsipeptides of the general formula (Ib) used as starting materials are known in some cases (cf. DE-OS [German Published Specification] 4 341 991, DE-OS [German Published Specification] 4 341 992, DE-OS [German Published Specification] 4 341 992) or can be obtained from N-terminal-protected didepsipeptides by the processes described there.

As carbon dioxide, the customary commercially available product, if appropriate alternatively so-called "dry ice", can be employed in the process according to the invention.

The alkylating agents of the formula (IX) additionally to be used as starting substances for carrying out process 3d according to the invention are generally known compounds of organic chemistry. In formula (IX) $R^8$ has the meaning which has already been mentioned as preferred for these substituents in connection with the description of the substances of the general formula (Ia) according to the invention and Hal has the meaning of an electron-withdrawing leaving group.

Suitable leaving groups are, for example, halogen, such as fluorine, chlorine, bromine and iodine, sulphonate such as aryl- and perfluoroalkylsulphonate, monosubstituted diazo and monosubstituted nitrato, and those additionally mentioned in J. March, Advanced Organic Chemistry, 3rd ed., John Wiley & Sons, New York 1985, pp. 310-316.

Compounds having a basic reaction which can be used in the present invention are one or more basic compounds of the elements lithium, sodium, magnesium, potassium, calcium, rubidium, strontium, caesium, barium, and/or of the ammonium ion. Suitable basic compounds are, for example, salts, oxides, hydrides and hydroxides which have a basic reaction. Examples which may be mentioned are: lithium hydride, sodium hydride, potassium hydride, calcium hydride, lithium hydroxide, sodium hydroxide, potassium hydroxide, rubidium hydroxide, magnesium hydroxide, calcium hydroxide, strontium hydroxide, barium hydroxide, lithium oxide, sodium peroxide, potassium oxide, potassium peroxide, calcium oxide, barium oxide, magnesium oxide, strontium oxide, lithium carbonate, lithium hydrogencarbonate, rubidium carbonate, rubidium hydrogencarbonate, caesium hydrogencarbonate, caesium carbonate, lithium cyanide, sodium cyanide, potassium cyanide, rubidium cyanide, ammonium hydrogencarbonate, caesium carbamate, ammonium carbamate, potassium sulphide, potassium hydrogensulphide, sodium sulphide, sodium hydrogensulphide and/or their naturally occurring or synthetically obtainable mixtures, for example dolomite or magnesium oxide carbonate and/or compounds which contain sodium or potassium metal on the corresponding carbonates in dispersed form.

Alkali metal carbonates and/or hydrogencarbonates, however, are preferred, very particularly preferably caesium carbonate or potassium carbonate.

The compounds having a basic reaction can be employed in anhydrous form, or if they are salts which crystallize with water of hydration, also in hydrated form. Preferably, however, anhydrous compounds are used.

Diluents used for carrying out process 3d according to the invention are the solvents mentioned in process 3a, e.g. amides such as hexamethylenephosphoramide, N,N-dimethylformamide, N,N-dipropylformamide, N,N-dibutylformamide, N-methyl-pyrrolidone or N-methyl-caprolactam, in particular N,N-dialkylformamides, such as N,N-dimethylformamide, and sulphoxides such as dimethyl sulphoxide, tetramethylene sulphoxide, dipropyl sulphoxide, benzyl methyl sulphoxide, diisobutyl sulphoxide, dibutyl sulphoxide, diisoamyl sulphoxide, in particular dimethyl sulphoxide.

Alternatively, process 3d can also be carried out in the presence of basic reaction auxiliaries, i.e. in the presence of other bases, for example in an amount of less than 0.5 mol, based on the base employed.

Those basic reaction auxiliaries which can use for carrying out process 3d according to the invention are all acid-binding agents mentioned in process 3a, but preferably tertiary amines, in particular trialkylamines such as triethylamine, N,N-diisopropylethylamine or N-methylmorpholine, and amidine bases or guanidine bases such as 7-methyl-1,5,7-triazabi-cyclo(4.4.0)dec-5-ene (MTBD); diazabicyclo-(4.3.0)nonene (DBN), diazabicyclo(2.2.2)-octane (DABCO), 1,8-diazabicyclo(5.4.0)-undecene (DBU) cyclohexyltetrabutylguanidine (CyTBG), cyclohexyltetramethylguanidine (CyTMG), cyclohexyltetrabutylguanidine, N,N,N,N-tetramethyl-1,8-naphthalenediamine, in particular cyclohexyltetramethylguanidine (CyTMG) and cyclohexyltetrabutylguanidine (CyTBG).

Process 3d is carried out by combining compounds of the general formula (Ib) at room temperature in the presence of carbon dioxide, a 2- to 3-fold excess of alkali metal carbonate of the formula (VII) and an alkylating agent of the formula (IX) in one of the diluents given above, if appropriate in the presence of a basic reaction auxiliary. In a second reaction step, the alkylation of the alkali metal salts of the formula (VIII) formed in situ with compounds of the formula (IX) takes place during a reaction time of 1 to 72 hours and a reaction temperature between –50 and +180° C.; temperatures in the range between –30 and +150° C. are preferred, in particular those in the range –10 to +100° C.

Fundamentally, it can be carried out under normal pressure, but it can also be carried out at elevated or reduced pressure. The process is preferably carried out at normal pressure or at pressures of up to 15 bar. At higher temperatures, it is advantageous to work at elevated pressure, if appropriate even above 15 bar.

The working-up and isolation of the reaction products is carried out by generally customary methods (cf. also the Preparation Examples).

If, in a process 3e for the preparation of the new didepsipeptides (Ia), as compounds of the general formula (Ic) tert-butyl N-methyl-N-(4-nitro-phenoxycarbonyl)-L-alanyl-D-lactate and as a nucleophile of the general formula (X) morpholine is employed, the process can be represented by the following reaction scheme:

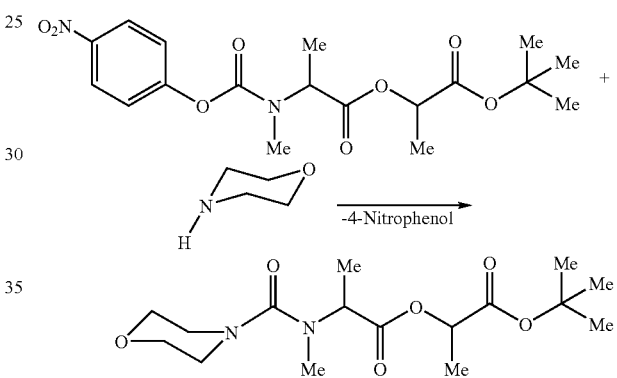

Formula (Ie) provides a general definition of the N-terminal-acylated didepsipeptides needed as starting substances for carrying out process 3e according to the invention. In this formula, $R^1$, $R^2$, $R^3$, $R^4$, $R^5$, G, W, X and B preferably represent those radicals which have already been mentioned as preferred for these substituents in connection with the description of the substances of the general formula (Ia) according to the invention.

The N-terminal-acylated didepsipeptides of the general formula (Ib) used as starting materials are known in some cases (cf. DE-OS [German Published Specification] 4 341 991, DE-OS [German Published Specification] 4 341 992, DE-OS [German Published Specification] 4 341 992), can be obtained by the processes described there or can be prepared by process 3b according to the invention shown above.

The nucleophilic agents of the formula (X) additionally to be used as starting substances for carrying out process 3e according to the invention are generally known compounds of organic chemistry. In the formula (X), $R^8$ and Y have the meaning which has already been mentioned as preferred in connection with the description of the substances of the general formula (Ia) according to the invention.

Process 3e is carried out by reacting compounds of the general formula (Ie) in the presence of a nucleophilic agent of the formula (X) in one of the diluents given above. The reaction time is 4 to 72 hours. The reaction is carried out at temperatures between +10° C. and +200° C., preferably between +20° C. and +150° C., particularly preferably at boiling temperature of the diluent.

Fundamentally, it can be carried out under normal pressure, but it can also be carried out at elevated or reduced pressure. The process is preferably carried out at normal pressure or at pressures of up to 15 bar. At higher temperatures it is advantageous to work at elevated pressure, if appropriate even above 15 bar.

After reaction is complete, the reaction solution is washed, and the organic phase is separated off, dried and concentrated in vacuo. The products which are formed can be purified in a customary manner by recrystallization, vacuum distillation or column chromatography (cf. also the Preparation Examples).

If, in process 3f for the preparation of the new didepsipeptides (Ia), as compounds of the general formula (Id) N-methyl-N-trimethylallophanoyl-L-alanyl-D-lactic acid and as compounds of the general formula (XI) L-homoproline methyl ester hydrochloride (H-Pec-OME.HCl) are employed, the process can be represented by the following reaction scheme:

for carrying out process 3e according to the invention. In this formula, $R^1$, $R^2$, $R^3$, $R^4$, $R^5$, G, X and Q preferably represent those radicals which have already been mentioned as preferred for these substituents in connection with the description of the substances of the general formula (Ia) according to the invention.

The C-terminal-deblocked didepsipeptides of the general formula (Id) used as starting materials are known in some cases (cf. DE-OS [German Published *Specification*] 4 341 991, DE-OS [German Published Specification] 4 341 992, DE-OS [German Published Specification] 4 341 992) or can be obtained by the processes described there.

For example, the C-terminal-deblocked didepsipeptides (Id) used as starting materials can be prepared by means of customary methods of a C-terminal deblocking such as acidolysis, for example in the case of a tert-butyl ester, or catalytic hydrogenation, for example in the case of a benzyl ester.

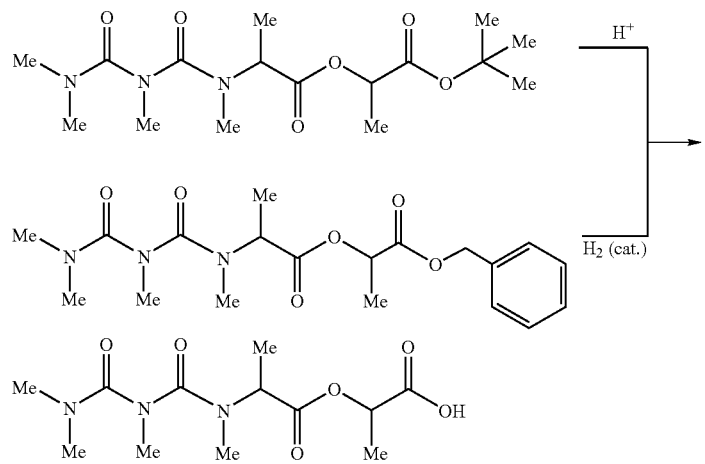

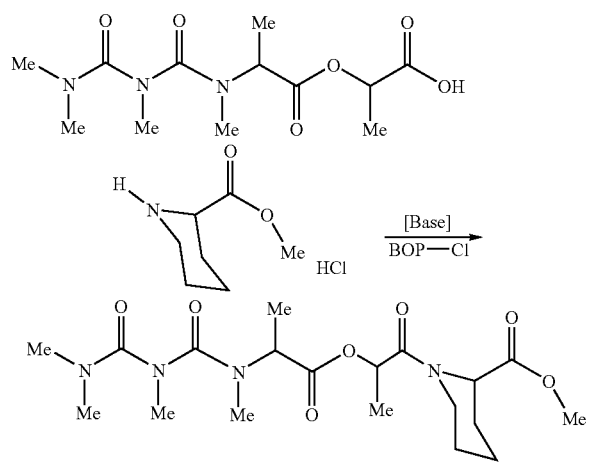

Formula (Id) provides a general definition of the C-terminal-deblocked didepsipeptides needed as starting substances for carrying out process 3e according to the invention.

Formula (XI) provides a general definition of the nucleophiles additionally to be used as starting substances for carrying out process 3e according to the invention.

In the formula (XI), B has the meaning which has already been mentioned as preferred for these substituents in connection with the description of the substances of the general formula (Ia) according to the invention.

The compounds of the formula (XI) are generally known compounds of organic chemistry and can be obtained commercially in some cases or by methods known from the literature.

The reaction of the C-terminal-deblocked didepsipeptides of the formula (Id) with compounds of the formula (XI) is preferably carried out using diluents in the presence of coupling reagents and in the presence of a basic reaction auxiliary.

Coupling reagents used for carrying out process 3f are all coupling reagents suitable for the preparation of an amide bond and already employed in process 3a mentioned above.

The preferred coupling is with phosphonium reagents such as bis(2-oxo-3-oxazolidinyl)-phosphonium acid chloride (BOP-Cl), benzotriazol-1-yl-oxy-tris(dimethylamino-phosphonium) hexafluorophosphate (BOP) and phosphonic acid ester reagents, such as diethyl cyanophosphonate (DEPC) or diphenylphosphoryl azide (DPPA).

Basic reaction auxiliaries which can be employed for carrying out process 3f according to the invention are also all acid-binding agents suitable for process 3a.

Preferably, tertiary amines, in particular trialkylamines such as triethylamine N,N-diisopropylethylamine, N-propyldiisopropylamine, N,N'-dimethyl-cyclohexylamine or N-methylmorpholine are suitable.

Diluents used for carrying out process 3f according to the invention are the solvents mentioned in process 3e, e.g. halogenohydrocarbons, in particular chlorohydrocarbons, such as methylene chloride of 1,2-dichloroethane and mixtures of these with other diluents mentioned.

Process 3j is in general carried out by reacting compounds of the formula (Id) with compounds of the general formula (XI) in one of the given diluents in the presence of one of the given coupling reagents and in the presence of one of the given basic reaction auxiliaries. The reaction time is 4 to 72 hours. The reaction is carried out at temperatures between −10° C. and +120° C., preferably between −5° C. and +50° C., particularly preferably at 0° C. to room temperature. It is carried out under normal pressure.

In general 1.0 to 3.0 mol, preferably 1.0 to 1.5 mol, of coupling reagent are employed per mole of C-terminal-deblocked didepsipeptide of the formula (Id) for carrying out process 3f according to the invention.

After reaction is complete, the reaction solution is washed, and the organic phase is separated off, dried and concentrated in vacuo. The products which are formed can be purified in a customary manner by recrystallization, vacuum distillation or column chromatography (cf. also the Preparation Examples).

Using processes 3a to 3f according to the invention, didepsipeptides of both L- and D-configuration are obtainable from the individual components, retaining the original configuration but also inversion is possible of the starting substances.

By the "inert solvents" described in the above process variants 3a to 3f, in each case solvents are meant which are inert under the respective reaction conditions, but do not have to be inert under any reaction conditions.

The active compounds have favourable toxicity for warm-blooded mammals and are suitable for controlling pathogenic endoparasites which occur in humans and in productive, breeding, zoo, laboratory, experimental animals and pets in animal keeping and animal breeding. In this connection, they are resistant to all or individual stages of development of the pests and to resistant and normally sensitive strains. By controlling the pathogenic endoparasites, disease, cases of death and yield reductions (e.g. in the production of meat, milk, wool, hides, eggs, honey etc.) should be decreased so that as a result of the use of the active compounds more economical and simpler animal keeping is possible. The pathogenic endoparasites include cestodes, trematodes, nematodes, Acantocephalae, in particular:

From the order of the Pseudophyllidea, e.g.: *Diphyllobothrium* spp., *Spirometra* spp., *Schistocephalus* spp., *Ligula* spp., *Bothridium* spp. *Diphlogonoporus* spp.

From the order of the Cyclophyllidea e.g.: *Mesocestoides* spp., *Anoplocephala* spp., *Paranoplocephala* spp., *Moniezia* spp., *Thysanosomsa* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

From the subclass of the Monogenea, e.g. *Gyrodactylus* spp., *Dactylogyrus* spp., *Polystoma* spp.

From the subclass of the Digenea e.g.: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonismus* spp.

From the order of the Enoplida e.g.: *Trichuris* spp., *Capillaria* spp., *Trichomosoides* spp., *Trichinella* spp.

From the order of the Rhabditia e.g.: *Micronema* spp., *Strongyloides* spp.

From the order of the Strongylida e.g.: *Stronylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Oxyurida e.g.: *Oxyuris* spp., *Enterobius* spp., *Passalurus* spp., *Syphacia* spp., *Aspiculuris* spp., *Heterakis* spp.

From the order of the Ascaridia e.g.: *Ascaris* spp., *Toxascaris* spp., *Toxocara* spp., *Parascaris* spp., *Anisakis* spp., *Ascaridia* spp.

From the order of the Spirurida e.g.: *Gnathostoma* spp., *Physaloptera* spp., *Thelazia* spp., *Gongylonema* spp., *Habronema* spp., *Parabronema* spp., *Draschia* spp., *Dracunculus* spp.

From the order of the Filariida e.g.: *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

From the order of Gigantorhynchida e.g.: *Filicollis* spp., *Moniliformis* spp., *Macracanthorhynchus* spp., *Prosthenorchis* spp.

The productive and breeding animals include mammals such as cattle, horses, sheep, pigs, goats, camels, water buffalo, donkeys, rabbits, fallow deer, reindeer, fur-bearing animals such as mink, chinchilla, raccoon, birds such as hens, geese, turkeys, ducks, fresh- and salt-water fish such as trout, carp, eels, reptiles, insects such as honey bees and silkworms.

Laboratory and experimental animals include mice, rats, guinea-pigs, golden hamsters, dogs and cats.

The pets include dogs and cats.

Administration can be carried out both prophylactically and therapeutically.

Administration of the active compounds is carried out, directly or in the form of suitable preparations, enterally, parenterally, dermally, nasally, by treatment of the surroundings or with the aid of active compound-containing shaped articles such as strips, disks, tapes, collars, ear tags, limb bands, marking devices.

Enteral administration of the active compounds is carried out, for example, orally in the form of powders, tablets, capsules, pastes, drinks, granules, orally administrable solutions, suspensions and emulsions, boli, medicated feed or drinking water. Dermal administration is carried out, for example, in the form of dipping, spraying or pouring-on and spotting-on. Parental administration is carried out, for example, in the form of injection (intramuscular, subcutaneous, intravenous, intraperitoneal) or by implants.

Suitable preparations are:

solutions such as injection solutions, oral solutions, concentrates for oral administration after dilution, solutions for use on the skin or in body cavities, pouring-on formulations, gels;

emulsions and suspensions for oral or dermal administration and for injection; semi-solid preparations;

formulations in which the active compound is processed in an ointment base or in an oil-in-water or water-in-oil emulsion base;

Solid preparations such as powders, premixes or concentrates, granules, pellets, tablets, boli, capsules; aerosols and inhalants, active compound-containing shaped articles.

Injection solutions are administered intravenously, intramuscularly and sub-cutaneously.

Injection solutions are prepared by dissolving the active compound in a suitable solvent and possibly adding additives such as solubilizers, acids, bases, buffer salts, antioxidants, preservatives. The solutions are sterile-filtered and bottled.

Solvents which may be mentioned are: physiologically tolerable solvents such as water, alcohols such as ethanol, butanol, benzyl alcohol, glycerol, propylene glycol, polyethylene glycols, N-methyl-pyrrolidone, and mixtures thereof.

The active compounds can optionally also be dissolved in physiologically tolerable vegetable or synthetic oils which are suitable for injection.

Solubilizers which may be mentioned are: solvents which promote the dissolution of the active compound in the main solvent or prevent its precipitation. Examples are polyvinylpyrrolidone, polyoxyethylated castor oil, polyoxyethylated sorbitan ester.

Preservatives are: benzyl alcohol, trichlorobutanol, p-hydroxybenzoic acid esters, n-butanol.

Oral solutions are administered directly. Concentrates are administered orally after prior dilution to the use concentration. Oral solutions and concentrates are prepared as described above in the case of the injection solutions, where sterile working can be dispensed with.

Solutions for use on the skin are trickled on, spread on, rubbed in, sprinkled on or sprayed on. These solutions are prepared as described above in the case of the injection solutions.

It can be advantageous to add thickeners during preparation. Thickeners are: inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pouring-on formulations are poured or sprayed onto limited areas of the skin, the active compound penetrating the skin and acting systemically.

Pouring-on formulations are prepared by dissolving, suspending or emulsifying the active compound in suitable skin-compatible solvents or solvent mixtures. If appropriate, other auxiliaries such as colourants, absorption-promoting substances, antioxidants, sunscreens, adhesives are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone, 2,2-dimethyl-4-oxy-methylene-1,3-dioxolane.

Colourants are all colourants permitted for use on animals and which can be dissolved or suspended.

Absorption-promoting substances are, for example, DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Sunscreens are, for example, novantisolic acid.

Adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colourants, absorption-promoting substances, preservatives, antioxidants, sunscreens, viscosity-enhancing substances.

Hydrophobic phases (oils) which may be mentioned are: liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_{8-12}$ or other specially selected natural fatty acids, partial glyceride mixtures of saturated or unsaturated fatty acids possibly also containing hydroxyl groups, mono- and diglycerides of the $C_8/C_{10}$ fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, ester mixtures related to the latter, inter alia.

Fatty alcohols such as isotridecyl alcohol, 2-octyldodecanol, cetylstearyl alcohol, oleyl alcohol.

Fatty acids such as oleic acid and its mixtures.

Hydrophilic phases which may be mentioned are: water, alcohols such as propylene glycol, glycerol, sorbitol and its mixtures.

Emulsifiers which may be mentioned are: non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-Na N-lauryl-β-iminodipropionate or lecithin;

anionic surfactants, such as Na lauryl sulphate, fatty alcohol ether sulphates, mono/dialkyl polyglycol ether orthophosphoric acid ester monoethynolamine salt.

Further auxiliaries which may be mentioned are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally, dermally or as an injection. They are prepared by suspending the active compound in a suspending agent, if appropriate with addition of other auxiliaries such as wetting agents, colourants, absorption-promoting substances, preservatives, antioxidants light screens.

Suspending agents which may be mentioned are all homogeneous solvents and solvent mixtures.

Wetting agents (dispersants) which may be mentioned are the surfactants given above.

Other auxiliaries which may be mentioned are those given above.

Semi-solid preparations can be administered orally or dermally. They differ from the suspensions and emulsions described above only by their higher viscosity.

For the production of solid preparations, the active compound is mixed with suitable excipients, if appropriate with addition of auxiliaries, and brought into the desired form.

Excipients which may be mentioned are all physiologically tolerable solid inert substances. Those used are inorganic and organic substances. Inorganic substances are, for example, sodium chloride, carbonates such as calcium carbonate, hydrogencarbonates, aluminium oxides, silicic acids, argillaceous earths, precipitated or colloidal silica, phosphates.

Organic substances are, for example, sugar, cellulose, foodstuffs and feeds such as milk powder, animal meal, grain meals and shreds, starches.

Auxiliaries are preservatives, antioxidants, colourants which have already been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear poly-vinylpyrrolidone, and dry binders such as microcrystalline cellulose.

The active compounds can also be present in the preparations as a mixture with synergists or with other active compounds which act against pathogenic endoparasites. Such active compounds are, for example, L-2,3,5,6-tetrahydro-6-phenylimidazolthiazole, benzimidazole carbamates, praziquantel, pyrantel, febantel.

Ready-to-use preparations contain the active compound in concentrations of 10 ppm-20 percent by weight, preferably from 0.1-10 percent by weight.

Preparations which are diluted before use contain the active compound in concentrations of 0.5-90% by weight, preferably of 5-50% by weight. In general, it has proved advantageous to administer amounts of approximately 1 to approximately 100 mg of active compound per kg of body weight per day to achieve effective results.

EXAMPLE 1

In vivo Nematode Test

*Trichostrongylus colubriformis*/Sheep

Sheep experimentally infected with *Trichostrongylus colubriformis* were treated after expiry of the prepatency time of the parasite. The active compounds were administered orally and/or intravenously as pure active compound.

The degree of effectiveness is determined by quantitatively counting the worm eggs excreted with the faeces before and after treatment.

Complete cessation of oviposition after treatment means that the worms have been expelled or are so damaged that they no longer produce eggs (effective dose).

Active compounds tested and effective doses can be seen from the following table.

| Active compound Example No. | Effective dose in [mg/kg] |
| --- | --- |
| 2 | 5 |
| 9 | 5 |
| 11 | 5 |
| 12 | 5 |
| 13 | 5 |
| 18 | 5 |
| I-7 | 5 |
| 46 | 5 |
| 68 | 5 |

EXAMPLE B

In vivo Nematode Test

*Haemonchus contortus*/Sheep

Sheep experimentally infected with *Haemonchus contortus* were treated after expiry of the prepatency time of the parasite. The active compounds were administered orally and/or intravenously as pure active compound.

The degree of effectiveness is determined by quantitatively counting the worm eggs excreted with the faeces before and after treatment.

Complete cessation of oviposition after treatment means that the worms have been expelled or are so damaged that they no longer produce eggs (effective dose).

Active compounds tested and effective doses can be seen from the following tables.

| Active compound Example No. | Effective dose in [mg/kg] |
| --- | --- |
| 2 | 5 |
| 8 | 5 |
| 9 | 5 |
| 10 | 5 |
| 11 | 5 |
| 12 | 5 |
| 19 | 5 |
| 20 | 5 |
| 30 | 5 |

-continued

| Active compound Example No. | Effective dose in [mg/kg] |
|---|---|
| 31 | 5 |
| 34 | 5 |
| 35 | 5 |
| 36 | 5 |
| 38 | 5 |
| 47 | 5 |
| 49 | 5 |
| 50 | 5 |
| 68 | 5 |
| 61 | 5 |
| I-4 | 5 |
| I-5 | 5 |
| I-7 | 5 |

PREPARATION EXAMPLES

Preparation by Process 3a

Example 1

Isobutyl N-methyl-N-trimethylallophanoyl-L-alanyl-D-lactate

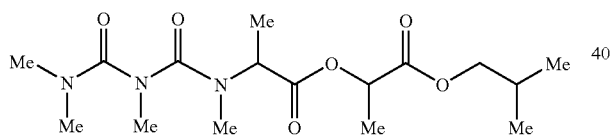

2.9 g (22.9 mmol) of N,N-diisopropylethylamine ("Hünig's base") and 2.9 g (11.4 mmol) of bis(2-oxo-3-oxazolidinyl)-phosphonium acid chloride (BOP-Cl) are added at 0° C. to a solution of 2.4 g (10.4 mmol) of N-methyl-N-trimethylallophanoyl-L-alanine and 1.5 g (10.4 mmol) of isobutyl D-lactate in 20 ml of methylene chloride and the mixture is stirred at room temperature for 18 [lacuna]. The reaction solution is shaken twice with water, and the organic phase is separated off and concentrated in vacuo after drying over sodium sulphate. The residual crude product is chromatographed on a silica gel column (silica gel 60—Merck, particle size: 0.04 to 0.063 mm) using the eluent cyclohexane:acetone (4:1). 1.6 g (57.2% of theory) of isobutyl N-methyl-N-trimethylallophanoyl-L-alanyl-D-lactate are obtained.

$^1$H-NMR (400 MHz, CDCl$_3$, δ): 0.92; 0.94 (d, 6H, 2×—CH$_3$; J=6.7 Hz); 2.91; 2.92; 2.94 (3s, 9H, 3×N—CH$_3$); 3.06 (s, 3H, —N—CH$_3$); 3.92 (m, 3H, —O—CH$_2$)—; 5.14 (m, 1H, CH) ppm GC-MS m/z (%): 360 (MH$^+$, 100); 271 (38); 214 (62).

Preparation by Process 3b

Example 2

Methyl N-methyl-N-trimethylallophanoyl-L-alanyl-D-lactate

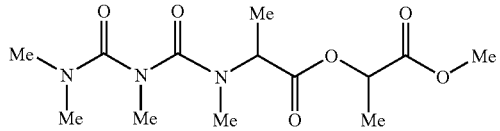

3.8 g (29.1 mmol) of N,N-diisopropylethylamine ("Hünig's base") and 2.1 g (12.7 mmol) of trimethylallophanoyl chloride are added at 0° C. to a solution of 2.0 g (10.6 mmol) of methyl N-methyl-L-alanyl-D-lactate in 100 ml of methylene chloride, and the mixture is stirred at 0° C. for two hours and then at room temperature for about 18 hours. The reaction solution is shaken twice with water, and the organic phase is separated off and concentrated in vacuo after drying over sodium sulphate. The residual crude product is chromatographed on a silica gel column (silica gel 60—Merck, particle size: 0.04 to 0.063 mm) using the eluent cyclohexane:ethyl acetate (3:1). 1.35 g (40.2% of theory) of methyl N-methyl-N-trimethylallophanoyl-L-alanyl-D-lactate are obtained.

$^1$H-NMR (400 MHz, CDCl$_3$, δ): 1.46; 1.49 (2d, 6H, 2×—CH$_3$; J=7.2 Hz); 2.91; 2.92; 2.93 (3s, 9H, 3×N—CH$_3$); 3.06 (s, 3H, —N—CH$_3$); 3.75 (s, 3H, —O—CH$_3$); 4.49; 5.13 (2q, 2H, 2×CH; J=7.2 Hz) ppm EI-MS m/z (%): 317 (M$^+$, 1); 286 (M$^+$-OMe, 1); 273 (M$^+$-CO$_2$, 7); 214 (3); 186 (40); 72 (100).

Preparation by Process 3c

Example 3 tert-Butyl N-methyl-N-trichloroacetylaminocarbonyl-L-alanyl-D-lactate

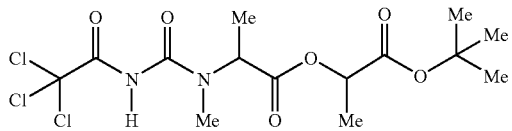

2.4 g (12.9 mmol) of trichloroacetyl isocyanate are added at 0° C. to a solution of 3.0 g (12.9 mmol) of tert-butyl N-methyl-L-alanyl-D-lactate in 30 ml of acetonitrile, and the mixture is stirred at 0° C. for two hours and then at room temperature for about 18 hours. The reaction solution is shaken twice with water, and the organic phase is separated off and concentrated in vacuo after drying over sodium sulphate. The residual crude product is chromatographed on a silica gel column (silica gel 60—Merck, particle size: 0.04 to 0.063 mm) using the eluent cyclohexane:acetone (4:1). 4.2 g (77.2% of theory) of tert-butyl N-methyl-N-trichloro-acetyl-L-alanyl-D-lactate are obtained.

$^1$H-NMR (400 MHz, CDCl$_3$, δ): 1.49; (s, 9H, —O-tBu); 1.40; 1.47; (2d, 6H, 2 x—CH$_3$; J=6.9 Hz); 2.95 (s, 3H, —N—CH$_3$); 3.98; 4.22 (2q, 2H, 2×CH; J=6.9 Hz); 9.05 (br., 1H, —CO—NH—CO) ppm Preparation by Process 3d

Example 4 tert-Butyl N-butyloxycarbonyl-N-methyl-L-alanyl-D-lactate

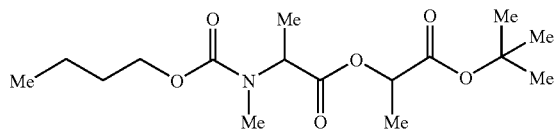

2.0 g (8.6 mmol) of tert-butyl N-methyl-L-alanyl-D-lactate, 2.1 g (15.2 mmol of potassium carbonate and 30 ml of dimethyl sulphoxide are gassed with carbon dioxide for one hour and then treated with 1.2 g (8.6 mmol) of butyl bromide. The reaction mixture was stirred at room temperature for 48 hours, then separated off from the solid, the volatile components were stripped off under reduced pressure, the residue was extracted with chloroform-water and the organic phase was separated off. The organic phase is then dried over sodium sulphate and concentrated in vacuo, and the residual oil is chromatographed on a silica gel column (silica gel 60—Merck, particle size: 0.04 to 0.063 mm).

$^1$H-NMR (400 MHz, CDCl$_3$, δ): 1.46; (s, 9H, —O-tBu) ppm EI-MS m/z %: 331 (M$^+$, 0.5); 275 (M$^+$-H$_2$C=CMe$_2$, 5); 158 (100).

Preparation by Process 3e

Example 5 tert-Butyl N-methyl-N-(4-nitro-phenoxy)carbonyl-L-alanyl-D-lactate

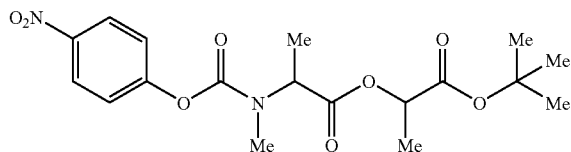

6.15 g (47.5 mmol) of N,N-diisopropylethyl-amine ("Hünig's base") and 4.4 g (21.6 mmol) of 4-nitrophenyl chloroformate are added at 0° C. to a solution of 5.0 g (21.6 mmol) of tert-butyl N-methyl-L-alanyl-D-lactate in 150 ml of methylene chloride, and the mixture is stirred at 0° C. for two hours and then at room temperature for about 18 hours. The reaction solution is shaken twice with water, and the organic phase is separated off and concentrated in vacuo after drying over sodium sulphate. The residual crude product is chromatographed on a silica gel column (silica gel 60—Merck, particle size: 0.04 to 0.063 mm) using the eluent cyclohexane:acetone (10:1).

$^1$H-NMR (400 MHz, CDCl$_3$, δ): 7.31; 8.24 (2d, 4H, 4-NO$_2$-phenoxy) ppm EI-MS m/z (%): 340 (M$^+$-H$_2$C=CMe$_2$, 2); 202 (100).

Example 6 tert-Butyl N-methyl-N-morpholinocarbonyl-L-alanyl-D-lactate

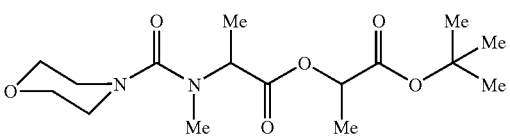

0.65 g (5.0 mmol) of N,N-diisopropylethylamine ("Hünig's base") and 0.45 g (5.0 mmol) of morpholine are added at room temperature to a solution of 2.0 g (5.0 mmol) of tert-butyl N-methyl-N-(4-nitro-phenoxy)carbonyl-L-alanyl-D-lactate in 40 ml of methylene chloride, and the mixture is stirred at reflux temperature for 18 hours. During the course of this a strong yellow colouration of the reaction mixture occurs. The reaction solution is shaken twice with water, and the organic phase is separated off and concentrated in vacuo after drying over sodium sulphate. The residual crude product is chroratographed on a silica gel column (silica gel 60—Merck, particle size: 0.04 to 0.063 mm) using the eluent cyclohexane:ethyl acetate (1:1).

$^1$H-NMR (400 MHz, CDCl$_3$, δ): 1.42; 1.46 (s/2d, 15H, —O-tBu/-CH$_3$); 2.90 (s, 3H, —N-Me) 3.25 (m, 4H, —CH$_2$—O—CH$_2$—); 3.68 (m, 4H, —CH$_2$—N—CH$_2$—); 4.69; 4.96 (2q, 2H, -2x—CH—) ppm EI-MS m/z (%): 344 (M$^+$, 4); 171 (100).

Preparation by Process 3f

Example 7

N-methyl-N-trimethylallophanoyl-L-alanyl-D-lactic Acid

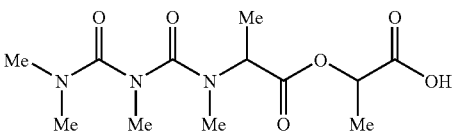

Dry hydrogen chloride gas is passed into a solution, cooled to 0° C., of 11.8 g (32.8 mmol) of tert-butyl N-methyl-N-trimethylallophanoyl-L-alanyl-D-lactate in 250 ml of absolute methylene chloride for 20 minutes. The mixture is then stirred at room temperature for about 16 hours and the entire reaction mixture is concentrated in vacuo.

10.0 g (100% of theory) of N-methyl-N-trimethylallophanoyl-L-alanyl-D-lactic acid are obtained, which can be reacted further without further purification.

$^1$H-NMR (400 MHz, CDCl$_3$, δ): 1.46; 1.51 (2d, 2H, 2x—CH$_3$; J=7.2 Hz); 2.91; 2.94; 3.05 (3s, 12H, 4×N-Me); 4.84; 5.17 (2q, 2H, —CH—, J=7.2 Hz) ppm EI-MS m/z (%); 304 (MH$^+$, 0.1); 259 (2); 214 (1); 186 (15); 129 (15); 72 (52); 58 (100).

Example 8

N-methyl-N-trimethylallophanoyl-L-alanyl-D-lactyl-L-homoproline Methyl Ester

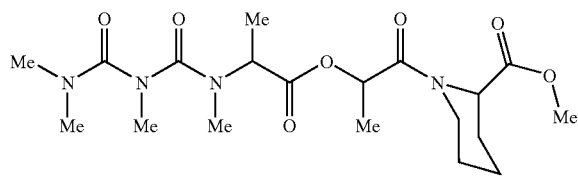

2.8 g (21.8 mmol) of N,N-diisopropylethylamine ("Hünig's base") and 1.85 g (7.25 mmol) of bis(2-oxo-3-oxazolidinyl)-phosphonium acid chloride (BOP-Cl) are added at 0° C. to a solution of 2.0 g (6.6 mmol of N-methyl-N-trimethylallo-phanoyl-L-alanyl-D-lactic acid and 1.3 g (7.25 mmol) of L-homoproline methyl ester hydrochloride (H-Pec-OMe.HCl) in 100 ml of methylene chloride and the mixture is stirred at 0° C. for 30 minutes, then at room temperature for 18 hours. The reaction solution is shaken twice with water, and the organic phase is separated off and concentrated in vacuo after drying over sodium sulphate. The residual crude product is chroma-tographed on a LiChroprep RP-18 column (LiChroprep RP-18—Merck, particle size: 0.04 to 0.063 mm) using the eluent acetonitrile-water (3:7). 0.32 g (11.3% of theory) is obtained.

EI-MS m/z (%): 428 ($M^+$, 2); 397 (2); 352 (17); 186 (38); 72 (100).

The compounds of the general formula (Ia) shown in Table 1 below can be prepared analogously to processes 3a-f.

TABLE 1

Examples of compounds of the formula (Ia)

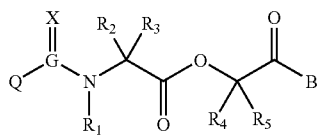

(Ia)

| Ex. No. | Q | G=X | $R^1$ | $R^2$ | $R^3$ | $R^4$ | $R^5$ | B | Physical Data[a] |
|---|---|---|---|---|---|---|---|---|---|
| 9 | $H_2C$=CH—$CH_2$—O— | C=O | -Me | -Me | —H | —H | -Me | —O-$^t$Bu | 316 ($MH^+$, 9); 260 ($MH^+$-$H_2C$=$CMe_2$, 100) |
| 10 | $Me_2CH$—$CH_2$—O— | C=O | -Me | -Me | —H | —H | -Me | —O-$^t$Bu | 331 ($M^+$, 1); 158 (100) |
| 11 | (Me-$CH_2$—)$_2$N— | C=O | -Me | -Me | —H | —H | -Me | —O-$^t$Bu | 430 ($M^+$, 0.2); 100 (100) |
| 12 | Me-O— | C=O | -Me | -Me | —H | —H | -Me | —O-$^t$Bu | 290 ($MH^+$, 11); 234 ($MH^+$-$H_2C$=$CMe_2$, 100) |
| 13 | Me-$CH_2$—O— | C=O | -Me | -Me | —H |  | -Me | —O-$^t$Bu | 303 ($M^+$, 0.2); 247 ($M^+$-$H_2C$=$CMe_2$, 8) |
| 14 | Me-($CH_2$)$_2$—O— | C=O | -Me | -Me | —H | —H | -Me | —O-$^t$Bu | 317 ($M^+$, 0.2); 261 ($M^+$-$H_2C$=$CMe_2$, 8) |
| 15 | $H_2C$=CMe-O— | C=O | -Me | -Me | —H | —H | -Me | —O-$^t$Bu | 315 ($M^+$, 0.2) |
| 16 | Cyclohexyl-$CH_2$—O— | C=O | -Me | -Me | —H | —H | -Me | —O-$^t$Bu | 371 ($M^+$, 0.5); 198 (100) |
| 17 | $Me_2CH$—($CH_2$)$_2$—O— | C=O | -Me | -Me | —H | —H | -Me | —O-$^t$Bu | 345 ($M^+$, 1); 172 (100) |
| 18 | $Me_2N$—CO—NMe- | C=O | -Me | -Me | —H | —H | -Me | —O-$^t$Bu | 359 ($M^+$, 0.6); 72 (100) |
| 19 | $Me_2CH$—O— | C=O | -Me | -Me | —H | —H | -Me | —O-$^t$Bu | 317 ($M^+$, 0.5); 144 (100) |
| 20 | Me-$CH_2$—CHMe-O— | C=O | -Me | -Me | —H | —H | -Me | —O-$^t$Bu | 331 ($M^+$, 0.5); 158 (100) |
| 21 | $Me_2CH$—$CH_2$—O— | C=O | -Me | —Et | —H | —H | -Me | —O-$^t$Bu | 345 ($M^+$, 0.5); 172 (100) |
| 22 | $Me_2CH$—$CH_2$—O— | C=O | -Me | -Me | —H | —H | -Me | —NMe-nBu | 358 ($M^+$, 9); 116 (100) |
| 23 | $Me_2CH$—$CH_2$—O— | C=O | -Me | -sBu | —H | —H | -Me | —O-$^t$Bu | 373 ($M^+$, 0.5); 200 (100) |
| 24 | Me-($CH_2$)$_3$—S— | C=O | -Me | -Me | —H | —H | -Me | —O-$^t$Bu | 347 ($M^+$, 3); 174 (100) |
| 25 | $Me_2CH$—$CH_2$—O— | C=O | -Me | -Me | —H | —H | —H | —O-$^t$Bu | 317 ($M^+$, 0.5); 158 (100) |

TABLE 1-continued

Examples of compounds of the formula (Ia)

(Ia)

| Ex. No. | Q | G=X | $R^1$ | $R^2$ | $R^3$ | $R^4$ | $R^5$ | B | Physical Data[a] |
|---|---|---|---|---|---|---|---|---|---|
| 26 | Me$_2$N—CO—NMe- | C=O | -Me | —H | —H | —H | -Me | —O-$^t$Bu | 345 (M$^+$, 0.1); 72 (100) |
| 27 | Me$_2$CH—CH$_2$—O— | C=O | -Me | —H | —H | —H | -Me | —O-$^t$Bu | 1.46 (s, 9H, tBu)[b] |
| 28 | Me$_2$N—CO—NMe- | C=O | -Me | -nPr | —H | —H | -Me | —O-$^t$Bu | 387 (M$^+$, 0.2); 72 (100) |
| 29 | Me$_2$CH—CH$_2$—O— | C=O | -Me | -nPr | —H | —H | -Me | —O-$^t$Bu | 304 (M$^+$-H$_2$C=CMe$_2$, 100) |
| 30 | Me$_2$N—CO—NMe- | C=O | -Me | -nPr | —H | —H | -Me | —NMe-sBu | |
| 31 | Me$_2$N—CO—NMe- | C=O | -Me | -Me | —H | —H | -Me | N-piperidinyl | 370 (M$^+$, 0.2); 72 (100) |
| 32 | Me$_2$N—CO—NMe- | C=O | -Me | -Me | —H | —H | -Me | 2-Me-N-piperidinyl | 384 (M$^+$, 0.2; 340 (M$^+$-CO$_2$, 26); 72 (100) |
| 33 | Me$_2$N—CO—NPr- | C=O | -Me | -Me | —H | —H | -Me | N-piperidinyl | 398 (M$^+$, 0.5); 72 (100) |
| 34 | H$_2$C=CH—CH$_2$—O— | C=O | -Me | -Me | —H | —H | -Me | N-piperidinyl | 376 (M$^+$, 12); 72 (100) |
| 35 | Et$_2$N— | C=O | -Me | -Me | —H | —H | -Me | N-piperidinyl | 341 (M$^+$, 6); 100 (100) |
| 36 | Et$_2$N— | SO$_2$ | -Me | -Me | —H | —H | -Me | N-piperidinyl | 349 (M$^+$; 0.5); 165 (100) |
| 37 | Me-CH$_2$—CHMe-O— | C=O | -Me | -Me | —H | —H | -Me | N-piperidinyl | 342 (M$^+$, 10); 102 (100) |
| 38 | Et$_2$N—CO—NMe- | C=O | -Me | -Me | —H | —H | -Me | N-piperidinyl | 326 (M$^+$-72, 28); 100 (100) |
| 39 | Et$_2$N—CO—NMe- | C=O | -Me | -Me | —H | —H | -Me | 2-Me-N-piperidinyl | 385 (MH$^+$; 0.5); 384 (M$^+$; 1); 72 (100) |
| 40 | Et$_2$N—CO—NMe- | C=O | -Me | -Me | —H | —H | -Me | 2,4-diMe-N-piperidinyl | 399 (MH$^+$; 0.5); 398 (M$^+$; 1), 72 (100) |
| 41 | Et$_2$N—CO—NMe- | C=O | -Me | -Me | —H | —H | -Me | 4,4-diMe-N-piperidinyl | 398 (M$^+$; 0.5); 72 (100) |

TABLE 1-continued

Examples of compounds of the formula (Ia)

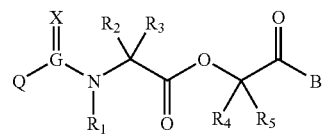

(Ia)

| Ex. No. | Q | G=X | $R^1$ | $R^2$ | $R^3$ | $R^4$ | $R^5$ | B | Physical Data[a] |
|---|---|---|---|---|---|---|---|---|---|
| 42 | $(H_2C=CH-CH_2)_2N-$ | C=O | -Me | -Me | —H | —H | -Me | —O-$^t$Bu | 358 ($M^+$; 13); 128 (100) |
| 43 | $(Me_2CH)_2N-$ | C=O | -Me | -Me | —H | —H | -Me | —O-$^t$Bu | |
| 44 | $Me_2N-$ | C=O | -Me | -Me | —H | —H | -Me | —O-$^t$Bu | 302 ($M^+$; 3); 129 (100) |
| 45 | $Me-CH_2-CHMe-O-$ | C=O | -Me | -Me | —H | —H | -Me | —O-Me | 289 ($M^+$; 8); 102 (100) |
| 46 | Me-O— | C=O | -Me | -Me | —H | —H | -Me | —O-Me | 247 ($M^+$; 1); 116 (100) |
| 47 | $Me_2N-CO-NPr-$ | C=O | -Me | -Me | —H | —H | -Me | —O-Me | 345 ($M^+$; 0.5); 72 (100) |
| 48 | $Et_2N-CO-NMe-$ | C=O | -Me | -Me | —H | —H | -Me | —O-Me | 346 ($M^+$+H; 44); 100 (100) |
| 49 | $Et_2N-$ | C=O | -Me | -Me | —H | —H | -Me | —O-Me | 288 ($M^+$; 2); 100 (100) |
| 50 | $H_2C=CH-CH_2-O-$ | C=O | -Me | -Me | —H | —H | -Me | —O-Me | 273 ($M^+$; 12); 142 (100) |
| 51 | Phenyl-O— | C=O | -Me | -Me | —H | —H | -Me | —O-$^t$Bu | 295 ($M^+$; $H_2C=CMe_2$; 3); 202 (100) |
| 52 | $H_2C=CMe-CH_2-$ | $SO_2$ | -Me | -Me | —H | —H | -Me | —O-$^t$Bu | 350 ($M^+$+H; 5); 294 (71); 176 (100) |
| 53 | $F_2C=CF-CH_2-CH_2-O-$ | C=O | -Me | -Me | —H | —H | -Me | —O-$^t$Bu | 383 ($M^+$+5); 210 (100) |
| 54 | $H_2C=CH-CH_2-O-$ | C=O | -Me | -iBu | —H | —H | -Me | —O-$^t$Bu | 358 ($M^+$+H, 10) 184 (100 |
| 55 | $H_2C=CH-CH_2-O-$ | C=O | -Me | -iBu | —H | —H | -Bn | —O-$^t$Bu | 434 ($M^+$+H; 8); 184 (100 |
| 56 | Benzyl-O— | C=O | -Me | -Bn | —H | —H | -iBu | —O-Me | |
| 57 | tBu—O— | C=O | —H | 1'Bn | —H | —H | -iPr | ![morpholine] | 232 ($M^+$+H; 38); 100 (100) |
| 58 | $H_2C=CH-CH_2-O-$ | C=O | -Me | -Me | —H | —H | -Me | ![morpholine] | 328 ($m^+$; 5); 142 (100) |
| 59 | $H_2C=CH-CH_2-O-$ | C=O | -Me | -Me | —H | —H | -Me | ![N-methylpiperazine] | 341 ($M^+$; 22); 70 (100) |
| 60 | $H_2C=CH-CH_2-O-$ | C=O | -Me | -Me | —H | —H | -Me | ![piperazine-ethyl-morpholine] | 440 ($M^+$; 2); 340 (100) |
| 61 | $H_2C=CH-CH_2-O-$ | C=O | -Me | -Me | —H | —H | -Me | ![piperazine-acyl-morpholine] | 454 ($M^+$; 12); 340 (100) |
| 62 | $H_2C=CH-CH_2-O-$ | C=O | -Me | -Me | —H | —H | -Me | —NMe-O-Me | 302 ($M^+$; 0.5); 142 (100) |

TABLE 1-continued

Examples of compounds of the formula (Ia)

(Ia)

| Ex. No. | Q | G=X | R¹ | R² | R³ | R⁴ | R⁵ | B | Physical Data[a] |
|---|---|---|---|---|---|---|---|---|---|
| 63 | H₂C=CH—CH2—O— | C=O | -Me | -Me | —H | —H | -Me | —NMe(CH₂)₂—NMe₂ | 343 (M⁺; 0.5); 58 (100) |
| 64 | H₂C=CH—CH2—O— | C=O | -Me | -Me | —H | —H | -Me | N-methyl-N-(pyridin-3-ylmethyl)amino | 363 (M⁺; 32); 142 (100) |
| 65 | H₂C=CH—CH₂—O— | C=O | -Me | -Me | —H | —H | -Me | 4-methylpiperazine-1-carboxylic acid ethyl ester | 399 (M⁺; 2); 142 (100) |
| 66 | H₂C=CH—CH—O— | C=O | -Me | -Me | —H | —H | -Me | 1-methyl-4-(pyridin-2-yl)piperazine | 404 (M⁺; 52); 107 (100)= |
| 67 | H₂C=CH—CH₂—O— | C=O | -Me | -Me | —H | —H | -Me | 1-methyl-4-(pyridin-4-yl)piperazine | 404 (M⁺; 7); 133 (100) |
| 68 | H₂C=CH—CH2$_O$- | C=O | -Me | -Me | —H | —H | -Me | 1-methyl-4-(pyrimidin-2-yl)piperazine | 405 (M⁺; 33); 142 (100) |
| 69 | tBu-O— | C=O | -Me | -Me | —H | —H | -Me | —O-Bn | 365 (M⁺; 0.5); 58 (100) |
| 70 | tBu-O— | C=O | -Me | -Me | —H | —H | -Me | —OH | 275 (M⁺; ); 58 (100) |
| 71 | tBu-O— | C=O | -Me | -Me | —H | —H | -Me | 1-methyl-1,2,3,6-tetrahydropyridine | 341 (MH⁺; 100); 141 (38) |
| 72 | tBu-O— | C=O | -Me | -Me | —H | —H | -Me | 1-allyl-4-methylpiperazine | 384 (MH⁺; 100); 141 (47) |
| 73 | tBu-O— | C=O | -Me | -Me | —H | —H | -Me | 1-benzyl-4-methylpiperazine | 434 (MH⁺; 100); 141 (59) |

TABLE 1-continued
Examples of compounds of the formula (Ia)
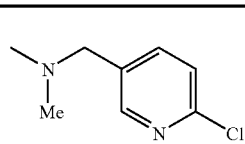
(Ia)
| Ex. No. | Q | G=X | R¹ | R² | R³ | R⁴ | R⁵ | B | Physical Data$^{a)}$ |
|---|---|---|---|---|---|---|---|---|---|
| 74 | tBu-O— | C=O | -Me | -Me | —H | —H | -Me | 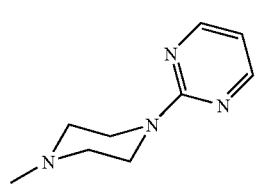 | 414 (MH⁺; 100); 141 (43) |
| 75 | Me₂N—CO—NMe- | C=O | -Me | -Me | —H | —H | -Me | 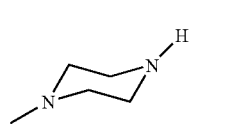 | 449 (M⁺; 22); 79 (100)) |
| 76 | tBu-O— | C=O | -Me | -Me | —H | —H | -Me | 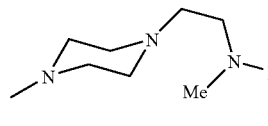 | 344 (MH⁺; 100); 244 (44) |
| 77 | H₂C=CH—CH₂—O— | C=O | -Me | -Me | —H | —H | -Me | 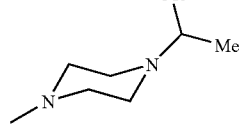 | |
| 78 | H₂C=CH—CH₂—O— | C=O | -Me | -Me | —H | —H | -Me | 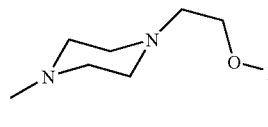 | 369 (M⁺; 19); 354 (M⁺−Me, 100) |
| 79 | H₂C=CH—CH₂—O— | C=O | -Me | -Me | —H | —H | -Me |  | 385 (M⁺; 1); 340 (100)( |
| 80 | H₂C=CH—CH₂—O— | C=O | -Me | -Me | —H | —H | -Me | 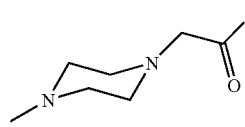 | 461 (M⁺; 12); 135 (100) |
| 81 | H₂C=CH—CH₂—O— | C=O | -Me | -Me | —H | —H | -Me | 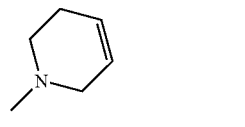 | 438 (M⁺; 1); 340 (100) |
| 82 | H₂C=CH—CH₂—O— | C=O | -Me | -Me | —H | —H | -Me | | |

TABLE 1-continued

Examples of compounds of the formula (Ia)

(Ia)

| Ex. No. | Q | G=X | R¹ | R² | R³ | R⁴ | R⁵ | B | Physical Data[a] |
|---|---|---|---|---|---|---|---|---|---|
| 83 | H₂C=CH—CH₃—O— | C=O | -Me | -Me | —H | —H | -Me | (N-methylpiperazinyl with N-allyl) | |
| 84 | H₂C=CH—CH₂—O— | C=O | -Me | -Me | —H | —H | -Me | N(Me)-CH₂-(6-chloropyridin-3-yl) | |
| 85 | tBu-O— | | C=O | -Me | -Me | —H | —H | -Me | (N-methylpiperazinyl N-C(O)NEt₂) | |
| 86 | H₂C=CH—CH₂—O— | C=O | -Me | -Me | —H | —H | -Me | (N-methylpiperazinyl N-C(O)NEt₂) | 426 (M⁺; 5); 100 (100) |
| 87 | tBu-O— | C=O | -Me | -Me | —H | —H | -Me | (N-methyl-4-phenyl-4-cyanopiperidinyl) | 443 (M⁺; 4); 58 (100) |
| 88 | H₂C=CH—CH₂—O— | C=O | -Me | -Me | —H | —H | -Me | 4-morpholino-phenyl-N(H)-Me | 419 (M⁺; 100); 204 (22) |
| 89 | H₂C=CH—CH₂—O— | C=O | -Me | -Me | —H | —H | -Me | N-methylazepanyl | 340 (M⁺; 8); 142 (100) |
| 90 | H₂C=CH—CH₂—O— | C=O | -Me | -Me | —H | —H | -Me | N-methylpyrrolidinyl | 312 (M⁺; 9); 142 (100) |

TABLE 1-continued

Examples of compounds of the formula (Ia)

$$\underset{R_1}{\overset{Q}{\underset{}{\bigg|}}}\overset{X}{\underset{}{\overset{\|}{G}}}\overset{R_2\ R_3}{\underset{}{\bigg|}}\overset{O}{\underset{R_4\ R_5}{\overset{}{\bigg|}}}B$$ (Ia)

| Ex. No. | Q | G=X | R¹ | R² | R³ | R⁴ | R⁵ | B | Physical Data[a] |
|---|---|---|---|---|---|---|---|---|---|
| 91 | H₂C=CH—CH₂—O— | C=O | -Me | -Me | —H | —H | -Me | 2-(morpholin-4-yl)-N-methylaniline group | 419 (M⁺; 17); 141 (4) |
| 92 | H₂C=CH—CH₂—O— | C=O | -Me | -Me | —H | —H | -Me | 1'-methyl-[1,4']bipiperidinyl group | 409 (M⁺; 25); 124 (100) |
| 93 | Me₂N— | C=O | -Me | -Me | —H | —H | -Me | —O-Me | 261 (M⁺; 1); 72 (100) |
| 94 | Me₂N— | SO₂ | -Me | -Me | —H | —H | -Me | —O-Me | 296 (M⁺; 2); 165 (100) |
| 95 | morpholin-4-yl | C=O | -Me | -Me | —H | —H | -Me | —O-Me | 302 (M⁺; 1); 114 (100) |
| 96 | Me-O—CO— | C=O | -Me | -Me | —H | —H | -Me | —O-Me | 275 (M⁺; 3); 144 (100) |
| 97 | H₂C=CMe-CH₂— | SO₂ | -Me | -Me | —H | —H | -Me | —O-Me | |
| 98 | piperidin-1-yl | SO₂ | -Me | -Me | —H | —H | -Me | —O-Me | 336 (M²; 2); 205 (100) |
| 99 | 4-(N,N-dimethylcarbamoyl)morpholine | C=O | -Me | -Me | —H | —H | -Me | —O-Me | 359 (M⁺; 1); 114 (100) |
| 100 | Me₂N—CO—NEt— | C=O | -Me | -Me | —H | —H | -Me | —O-Me | 331 (M⁺; 1); 72 (100) |
| 101 | morpholin-4-yl | SO₂ | -Me | -Me | —H | —H | -Me | —O-Me | 338 (M⁺; 3); 217 (100) |
| 102 | Me₂N—CO—NEt— | C=O | -Me | -Me | —H | —H | -Me | 1-methylpiperidin-4-yl group | 385 (M⁺; 1); 72 (100) |

TABLE 1-continued

Examples of compounds of the formula (Ia)

(Ia) — general structure: Q–G(=X)–N(R₁)–C(R₂)(R₃)–C(=O)–O–C(R₄)(R₅)–C(=O)–B

| Ex. No. | Q | G=X | R¹ | R² | R³ | R⁴ | R⁵ | B | Physical Data[a)] |
|---|---|---|---|---|---|---|---|---|---|
| 103 | 4-morpholinyl–C(=O)–N(Me)– | C=O | -Me | -Me | —H | —H | -Me | 1-methylpiperidin-4-yl | 412 (M⁺; 1); 114 (100) |
| 104 | 4-morpholinyl– | SO₂ | -Me | -Me | —H | —H | -Me | 1-methylpiperidin-4-yl | 392 (MH⁺; 100); 207 (28) |
| 105 | H₂C=CH—CH₂—O— | C=O | -Me | -iPr | —H | —H | -Me | 1-methylpiperidin-4-yl | 354 (M⁺; 2); 170 (100) |
| 106 | Me₂N—CO—NMe- | C=O | -Me | -iPr | —H | —H | -Me | 1-methylpiperidin-4-yl | 399 (M⁺; 0.5); 72 (100) |
| 107 | H₂C=CH—CH₂—O— | C=O | -Me | -Bn | —H | —H | -Me | 1-methylpiperidin-4-yl | 402 (M⁺; 16); 139 (100) |
| 108 | Me₂N—CO—NMe- | C=O | -Me | -Bn | —H | —H | -Me | 1-methylpiperidin-4-yl | 446 (M⁺; 0.5); 72 (100) |
| 109 | H₂C=CH—CH₂O— | C=O | -Me | -sBU | —H | —H | -iPr | 1-methylpiperidin-4-yl | 396 (M⁺; 2); 184 (100) |
| 110 | Me₂N—CO—NMe- | C=O | -Me | -sBU | —H | —H | -iPr | 1-methylpiperidin-4-yl | |
| 111 | Cl—CHMe-O— | C=O | -Me | -Me | —H | —H | -Me | —O-Me | 295 (M⁺; 2); 164 (100) |
| 112 | Ac-O—CHMe-O— | C=O | -Me | -Me | —H | —H | -Me | —O-Me | |
| 113 | Me₂N—CO—NMe- | C=O | -Me | -Me | —H | —H | -Me | 1-methylpiperidin-4-yl-NH-C(=O)-O-C(Me)₃ (Boc-amino) | 485 (M⁺; 2); 72 (100) |

TABLE 1-continued

Examples of compounds of the formula (Ia)

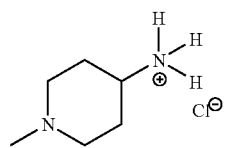

| Ex. No. | Q | G=X | R¹ | R² | R³ | R⁴ | R⁵ | B | Physical Data[a] |
|---|---|---|---|---|---|---|---|---|---|
| 114 | Me₂N—CO—NMe- | C=O | -Me | -Me | —H | —H | -Me | 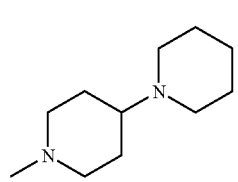 | |
| 115 | Me₂N—CO—NMe- | C=O | -Me | -Me | —H | —H | -Me | | |

Abbreviation: Ac: -acetyl; Me: -methyl; Et: -ethyl; Pr: -propyl; Bu: -butyl; Bn: -benzyl; i-, s- and t-: iso-; secondary- and tertiary
[a] FAB-MS, MS-APCI or AI-MS m/z (%).
[b] ¹H-NMR (400 MHz, CDCl₃, δ) in ppm Starting Substances of the Formula (I)

Example (I-1)

N-Benzyl-N-methyl-L-alanyl-D-lactic Acid Piperidide

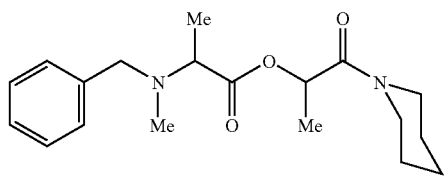

5.4 g (41.4 mmol) of N,N-diisopropylethylamine (Hünig's base) and 5.3 g (20.7 mmol) of bis(2-oxo-3-oxazolidinyl)-phosphonium acid chloride (BOP-Cl) are added at 0° C. to a solution of 5.0 g (18.8 mmol) of N-benzyl-N-methyl-L-alanyl-D-lactic acid and 1.6 g (20.7 mmol) of piperidine in 150 ml of methylene chloride, and the mixture is stirred at 0° C. for two hours and then at room temperature for 18 hours. The residual crude product is chromatographed on a silica gel column (silica gel 60—Merck, particle size: 0.04 to 0.063 mm) using the eluent cyclohexane:ethyl acetate (3:1). 3.5 g (55.8% of theory) of N-benzyl-N-methyl-L-alanyl-D-lactic acid piperidide are obtained.

EI-MS m/z (%): 332 (M⁺, 1); 213 (2); 192 (2); 148 (100); 120 (35); 91 (55)

Example (I-2)

Methyl-L-alanyl-D-lactic Acid Piperidide

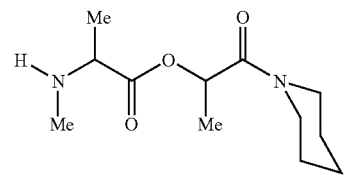

3.3 g (9.9 mmol) of N-benzyl-N-methyl-L-alanyl-D-lactic acid piperidide are hydrogenated in 100 ml of ethanol in the presence of 0.35 g of Pd(OH)₂-carbon [20% Pd content] until absorption of hydrogen is complete (about 4 hours). After filtering off the catalyst, the entire reaction solution is concentrated in vacuo. 2.4 g (100% of theory) of N-methyl-L-alanyl-D-lactic acid piperidide are obtained.

GC-MS m/z (%): 243 (MH⁺, 100); 158 (32)

Example (I-3)

Methyl N-benzyl-N-methyl-L-alanyl-D-lactate

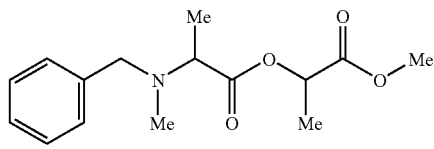

The coupling reaction is carried out analogously to the reaction procedure of Example 1 using:
18.5 g (95.7 mmol) of N-benzyl-N-methyl-L-alanine,
10.0 g (95.7 mmol) of methyl (R)-(+)-lactate,
300 ml of absol. methylene chloride,
36.7 g (284.5 mmol) of N,N-diisopropylethylamine ("Hünig's base"),
29.0 g of bis(2-oxo-3-oxazolidinyl)-phosphonium acid chloride (BOP-Cl).

The residual crude product is chromatographed on a silica gel column (silica gel 60—Merck, particle size: 0.04 to 0.063 mm) using the eluent cyclohexane:ethyl acetate (3:1). 5.6 g (20.9% of theory of methyl N-benzyl-N-methyl-L-alanyl-D-lactate are obtained.

EI-MS m/z (%): 279 ($M^+$, 11); 148 (Ph-$CH_2$—NMe-CHMe, 100); 91 (Ph-$CH_2$—, 99).

The starting substances of the general formula (I) shown in Table 2 below can be prepared analogously to examples (I-1) to (I-3).

TABLE 2

Examples of compounds of the formula (I)

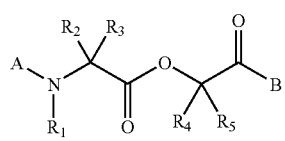

| Ex. No. | A | $R^1$ | $R^2$ | $R^3$ | $R^4$ | $R^5$ | B | Physical Data[a] |
|---|---|---|---|---|---|---|---|---|
| I-4 | —CO—O-Benzyl | -Me | -Me | —H | —H | -Me | —O-$^t$Bu | |
| I-5 | —CO—O-Benzyl | -Me | -Me | —H | —H | -Me | —OH | |
| I-6 | —CO—O-Benzyl | -Me | —H | —H | —H | -Me | —O-$^t$Bu | |
| I-7 | —CO—O-Benzyl | -Me | —H | —H | —H | -Me | —OH | |
| I-8 | —CO—O-$^t$Bu | -Me | —CHMe (O-Bn) | —H | —H | -Me | —O-Bn | |
| I-9 | -Benzyl | -Me | -Me | —H | —H | -Me | —NMe-nBu | 334 ($M^+$, 7); 148 (100) |
| I-10 | —H | -Me | -Me | —H | —H | -Me | —NMe-nBu | 244 ($M^+$, 0.5); 58 (100) |
| I-11 | -Benzyl | -Me | -Me | —H | —H | -Me | —O-iBu | 448 ($M^+$, 1); 148 (100) |
| I-12 | —H | -Me | -Me | —H | —H | -Me | —O-iBu | 232 ($MH^+$, 100) |
| I-13 | -Benzyl | -Me | -Me | —H | —H | -Me | —NMe-sBu | 334 ($M^+$, 1); 148 (100) |
| I-14 | —H | -Me | -Me | —H | —H | -Me | —NMe-sBu | |
| I-15 | -Benzyl | -Me | -Me | —H | —H | -Me | (2-Me-N-Me-piperidinyl) | 346 ($M^+$, 1); 148 (100) |
| I-16 | —H | -Me | -Me | —H | —H | -Me | (2-Me-N-Me-piperidinyl) | 257 ($MH^+$, 100) |
| I-17 | —H | -Me | -Me | —H | —H | -Me | —O-Me | 3,76 (s, 3H, —O-Me)[b] |
| I-18 | -Benzyl | -Me | -Me | —H | —H | -Me | (4,4-diMe-N-Me-piperidinyl) | 360 ($M^+$, 4); 148 (100) |
| I-19 | —H | -Me | -Me | —H | —H | -Me | (4,4-diMe-N-Me-piperidinyl) | |
| I-20 | -Benzyl | -Me | -Me | —H | —H | -Me | (2,4-diMe-N-Me-piperidinyl) | 360 ($M^+$, 3); 148 (100) |

TABLE 2-continued

Examples of compounds of the formula (I)

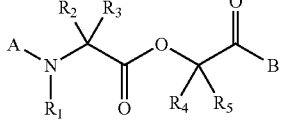

| Ex. No. | A | R¹ | R² | R³ | R⁴ | R⁵ | B | Physical Data$^{a)}$ |
|---|---|---|---|---|---|---|---|---|
| I-21 | —H | -Me | -Me | —H | —H | -Me | 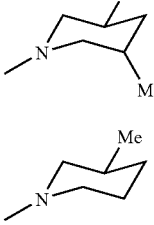 | 271 (MH⁺, 2); 58 (100) |
| I-22 | -Benzyl | -Me | -Me | —H | —H | -Me | 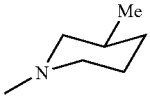 | 346 (M⁺, 2); 148 (100) |
| I-23 | —H | -Me | -Me | —H | —H | -Me | 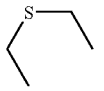 | |
| I-24 | -Benzyl | -Me | -iBu | —H | —H | —H | —O-$^t$Bu | 350 (M⁺+H, 16); 190 (100) |
| I-25 | -Benzyl | -Me | -iBu | —H | —H | —H | —OH | 272 (M⁺−21); 100 (100) |
| I-26 | —H | -Me | -iBu | —H | —H | —H | —O-$^t$Bu | 260 (M⁺+H, 100); 204 (74) |
| I-27 | -Benzyl | -Me | -iBu | —H | —H | —H | —O-Me | 306 (M⁺−H, 20); 307 (M⁺, 16); 91 (100) |
| I-28 | -Benzyl | -Me | -iBu | —H | —H | —H | —O—Et | |
| I-29 | -Benzyl | -Me | -iBu | —H | —H | -Bn | —OH | 384 (M⁺+H, 42); 91 (100) |
| I-30 | -Benzyl | —H | -iBu | —H | —H | -Me | —O-$^t$Bu | 350 (M⁺+H, 100); 348 (20) |
| I-31 | -Benzyl | -Me | -iBu | —H | —H | -Bn | —O-Me | 348 (M⁺+H, 17); 396 (M−H, 18), 190 (100) |
| I-32 | -Benzyl | —H | -iBu | —H | —H | -Me | —OH | 294 (M⁺+H, 36); |
| I-33 | —H | -Me | -iBu | —H | —H | -Bn | —O-Me | 308 (M⁺+H, 100) |
| I-34 | —H | —H | -iBu | —H | —H | -Bn | —O-Me | |
| I-35 | -Benzyl | -Me | -iBu | —H | —H | -Me | —O-Me | 322 (M⁺+H, 16); 320 (M⁺−H, 26); 190 (100) |
| I-36 | —H | -Me | -iBu | —H | —H | -Me | —O-Me | 232 (M⁺+H, 38); 100 (100) |
| I-37 | -Benzyl | —H | -nPr | —H | —H | -Me | —O-$^t$Bu | 336 (M⁺+H, 100) |
| I-38 | -Benzyl | —H | -nPr | —H | —H | -Me | —OH | 280 (M⁺+H, 100); 91 (62) |
| I-39 | —H | —H | -nPr | —H | —H | -Me | —O-$^t$Bu | 199 (M⁺−46, 96); 72 (100) |
| I-40 | -Benzyl | -Me | -nPr | —H | —H | -Me | —O-$^t$Bu | 350 (M⁺+H, 16); 348 (20); 176 (100) |
| I-41 | -Benzyl | -Me | -nPr | —H | —H | -Bn | —O-$^t$Bu | 426 (M⁺+H, 17); 414 (M⁺−H, 19); 179 (100) |
| I-42 | —CO—O-$^t$Bu | 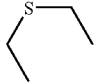 | —H | —H | —H | —O-$^t$Bu | | 348 (M⁺+H, 17); 346 (M⁺−H, 16); 236 (100) |
| I-43 | —H |  | —H | —H | —H | —OH | | 192 (M⁺+H, 90); 134 (100) |

TABLE 2-continued

Examples of compounds of the formula (I)

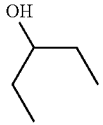

| Ex. No. | A | R¹ | R² | R³ | R⁴ | R⁵ | B | Physical Data[a] |
|---|---|---|---|---|---|---|---|---|
| I-44 | —CO—O-$^t$Bu | | OH 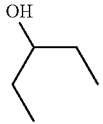 | —H | —H | -Me | —O-$^t$Bu | 360 (M⁺+H, 92); 304 (100) |
| I-45 | —H | | OH 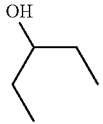 | —H | —H | -Me | —OH | 204 (M⁺+H, 100); 190 (32) |
| I-46 | —CO—O-$^t$Bu | | —(CH₂)₃— | —H | —H | -Bn | —O-$^t$Bu | 420 (M⁺+H, 94); 364 (100) |
| I-47 | —H | | —(CH₂)₃— | —H | —H | -Me | —OH | 188 (M⁺+H, 100) |
| I-48 | —CO—O-$^t$Bu | | —(CH₂)₃— | —H | —H | -Me | —O-$^t$Bu | 344 (M⁺+H, 100); 288 (76) |
| I-49 | —CO—O-$^t$Bu | | —(CH₂)₄— | —H | —H | -Bn | —O-$^t$Bu | 434 (M⁺+H, 20); 334 (100) |
| I-50 | —H | | —(CH₂)₄— | —H | —H | -Bn | —OH | 278 (M⁺+H, 100) |
| I-51 | —CO—O-Benzyl | —H | -iBu | —H | —H | —H | —OH | 322 (M⁺+H, 40); 156 (100) |
| I-52 | -Benzyl | -Me | -Me | —H | —H | -Me | 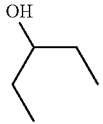 | 334 (M⁺; 1); 148 (100) |
| I-53 | —H | -Me | -Me | —H | —H | -Me | 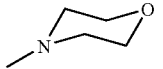 | |
| I-54 | -Benzyl | -Me | -Me | —H | —H | -Me | 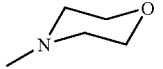 | 347 (M⁺; 0.66); 148 (100) |
| I-55 | —H | -Me | -Me | —H | —H | -Me | 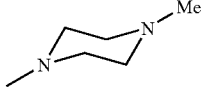 | 257 (M⁺; 5); 58 (100) |
| I-56 | -Benzyl | -Me | -Me | —H | —H | -Me | 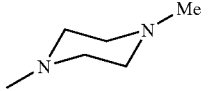 | 330 (M⁺; 1); 148 (100) |
| I-57 | -Benzyl | -Me | -Me | —H | —H | -Me | 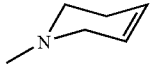 | 446 (M⁺; 1.14); 346 (70); 148 (100); 100 (92) |
| I-58 | —H | -Me | -Me | —H | —H | -Me | 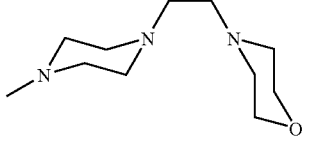 | 356 (M⁺; 1); 256 (35); 100 (100); 58 (66) |

TABLE 2-continued

Examples of compounds of the formula (I)

| Ex. No. | A | R¹ | R² | R³ | R⁴ | R⁵ | B | Physical Data$^{a)}$ |
|---|---|---|---|---|---|---|---|---|
| I-59 | -Benzyl | -Me | -Me | —H | —H | -Me | (N-methylpiperazinyl-ethyl-morpholine) | 460 (M⁺; 0.45); 341 (38); 148 (100); 91 (53) |
| I-60 | —H | -Me | -Me | —H | —H | -Me | (N-methylpiperazinyl-ethyl-morpholine) | 370 (M⁺; 20); 256 (41); 148 (40); 58 (100) |
| I-61 | -Benzyl | -Me | -Me | —H | —H | -Me | —NMe-OMe | 308 (M⁺; 2); 148 (100) |
| I-62 | —H | -Me | -Me | —H | —H | -Me | —NMe-OMe | 218 (M; 0.5); 58 (100) |
| I-63 | -Benzyl | -Me | -Me | —H | —H | -Me | (Me₂N-CH₂CH₂-NMe-) | 349 (M⁺; 0.24); 148 (100) |
| I-64 | —H | -Me | -Me | —H | —H | -Me | (Me₂N-CH₂CH₂-NMe-) | |
| I-65 | -Benzyl | -Me | -Me | —H | —H | -Me | (1-methyl-4-oxopiperidin-yl) | 346 (M⁺; 0.5); 148 (100) |
| I-66 | —H | -Me | -Me | —H | —H | -Me | (1-methyl-4-oxopiperidin-yl) | 256 (M, S); 58 (100) |
| I-67 | -Benzyl | -Me | -Me | —H | —H | -Me | (N-methyl-N-((6-chloropyridin-3-yl)methyl)amino) | 403 (M⁺; 0.5); 148 (100); 91 (52) |
| I-68 | —H | -Me | -Me | —H | —H | -Me | (N-methyl-N-(pyridin-3-ylmethyl)amino) | 279 (M⁺, 0.5); 121 (32); 58 (100) |
| I-69 | -Benzyl | -Me | -Me | —H | —H | -Me | (N-methylpiperazinyl-ethyl-NMe₂) | 404 (M⁺; 0.28); 346 (M⁺—(CH₂)₂—NMe₂; 62); 285 (60); 148 (100) |
| I-70 | —H | -Me | -Me | —H | —H | -Me | (N-methylpiperazinyl-ethyl-NMe₂) | 314 (M⁺; 0.5); 58 (100) |

TABLE 2-continued
Examples of compounds of the formula (I)
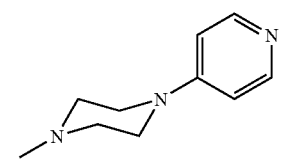
| Ex. No. | A | $R^1$ | $R^2$ | $R^3$ | $R^4$ | $R^5$ | B | Physical Data[a] |
|---|---|---|---|---|---|---|---|---|
| I-71 | -Benzyl | -Me | -Me | —H | —H | -Me | 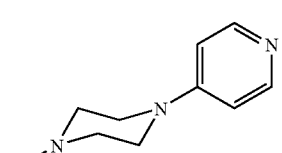 | 410 (M+; 1); 291 (50); 148 (100); 91 (55) |
| I-72 | —H | -Me | -Me | —H | —H | -Me | 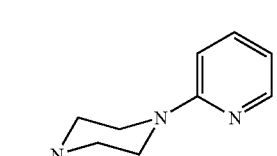 | |
| I-73 | -Benzyl | -Me | -Me | —H | —H | -Me | 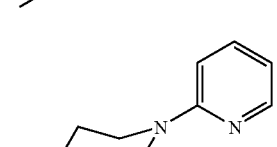 | 410 (M+; 0.24); 291 (32); 148 (100); 91 (42) |
| I-74 | —H | -Me | -Me | —H | —H | -Me | 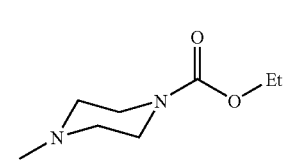 | |
| I-75 | -Benzyl | -Me | -Me | —H | —H | -Me | 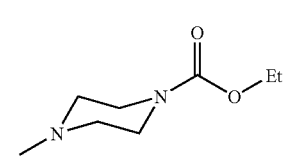 | 405 (M+; 1); 148 (100); 91 (41) |
| I-76 | —H | -Me | -Me | —H | —H | -Me | 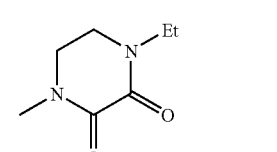 | 315 (M+; 0.5); 58 (100) |
| I-77 | -Benzyl | -Me | -Me | —H | —H | -Me | 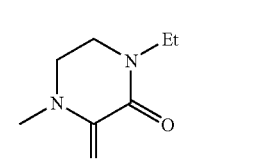 | 489 (M+; 1); 148 (100); 91 (40) |
| I-78 | —H | -Me | -Me | —H | —H | -Me | | |

TABLE 2-continued

Examples of compounds of the formula (I)

| Ex. No. | A | R¹ | R² | R³ | R⁴ | R⁵ | B | Physical Data$^{a)}$ |
|---|---|---|---|---|---|---|---|---|
| I-79 | -Benzyl | -Me | -Me | —H | —H | -Me | (N-methylpiperidine-pyrimidinyl) | 411 (M⁺; 0.5); 148 (100) |
| I-80 | —H | -Me | -Me | —H | —H | -Me | (N-methylpiperidine-pyrimidinyl) | 321 (M⁺; 8); 58 (100) |
| I-81 | -Benzyl | -Me | -Me | —H | —H | -Me | (N-methylpiperidine-CH₂CH₂-NEt₂) | 433 (MH⁺; 100); 141 (12) |
| I-82 | —H | -Me | -Me | —H | —H | -Me | (N-methyl-N'-ethyl-piperazine-2,3-dione) | 343 (MH⁺; 100); 141 (11) |
| I-83 | -Benzyl | -Me | -Me | —H | —H | -Me | (N-methylpiperidine-CHMe₂) | 376 (MH⁺; 100); 141 (14) |
| I-84 | —H | -Me | -Me | —H | —H | -Me | (N-methylpiperidine-CHMe₂) | 286 (MH⁺; 100); 201 (22) |
| I-85 | -Benzyl | -Me | -Me | —H | —H | -Me | (N-methylpiperidine-CH₂CH₂-OMe) | 392 (MH⁺; 100); 141 (22) |
| I-86 | —H | -Me | -Me | —H | —H | -Me | (N-methylpiperidine-CH₂CH₂-OMe) | 302 (MH⁺; 100); 217 (20) |
| I-87 | -Benzyl | -Me | -Me | —H | —H | -Me | (N-methylpiperidine-CH₂-benzodioxole) | 468 (MH⁺; 100); 141 (19) |

TABLE 2-continued
Examples of compounds of the formula (I)
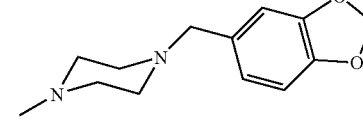
| Ex. No. | A | R¹ | R² | R³ | R⁴ | R⁵ | B | Physical Data[a] |
|---|---|---|---|---|---|---|---|---|
| I-88 | —H | -Me | -Me | —H | —H | -Me | 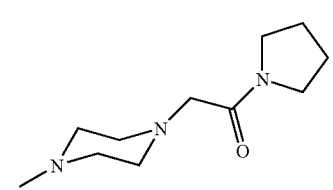 | 378 (MH⁺; 100); 244 (42) |
| I-89 | -Benzyl | -Me | -Me | —H | —H | -Me | 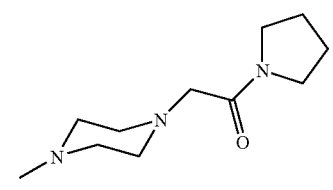 | 445 (MH⁺; 100); 141 (18) |
| I-90 | —H | -Me | -Me | —H | —H | -Me | 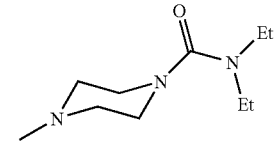 | 355 (MH⁺; 100); 141 (4) |
| I-91 | —H | -Me | -Me | —H | —H | -Me | 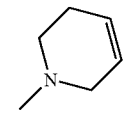 | 342 (NH⁺; 1); 58 (100) |
| I-92 | —H | -Me | -Me | —H | —H | -Me | 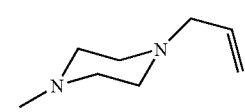 | 241 (MH⁺; 100) 141 (4) |
| I-93 | —H | -Me | -Me | —H | —H | -Me | 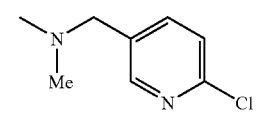 | 284 (MH⁺; 100); |
| I-94 | —H | -Me | -Me | —H | —H | -Me | 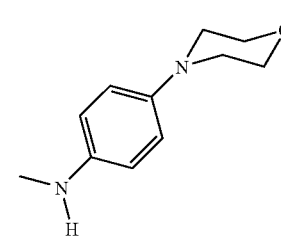 | 314 (MH⁺; 100); |
| I-95 | -Benzyl | -Me | -Me | —H | —H | -Me |  | 425 (M⁺; 13); 148 (100) |

TABLE 2-continued

Examples of compounds of the formula (I)

| Ex. No. | A | R¹ | R² | R³ | R⁴ | R⁵ | B | Physical Data$^{a)}$ |
|---|---|---|---|---|---|---|---|---|
| I-96 | —H | -Me | -Me | —H | —H | -Me | 4-(morpholin-4-yl)phenyl-N(H)Me | 335 (M⁺; 60); 250 (100) |
| I-97 | -Benzyl | -Me | -Me | —H | —H | -Me | 2-(morpholin-4-yl)phenyl-N(H)Me | 425 (M⁺; 1); 148 (100) |
| I-98 | -Benzyl | -Me | -Me | —H | —H | -Me | 2-methoxy-6-(morpholin-4-yl)phenyl | 426 (M⁺; 1); 148 (100) |
| I-99 | -Benzyl | -Me | -Me | —H | —H | -Me | 3-methoxy-5-(morpholin-4-yl)phenyl | 426 (M⁺; 4); 148 (100) |
| I-100 | -Benzyl | -Me | -Me | —H | —H | -Me | 1'-methyl-[1,4'-bipiperidin]-4-yl | 415 (M⁺; 0.5); 148 (100) |
| I-101 | —H | -Me | -Me | —H | —H | -Me | 1'-methyl-[1,4'-bipiperidin]-4-yl | 325 (M⁺; 6); 124 (100) |
| I-102 | -Benzyl | -Me | -Me | —H | —H | -Me | 1-methylazepan-4-yl | 346 (M⁺; 2); 148 (100) |

TABLE 2-continued
Examples of compounds of the formula (I)
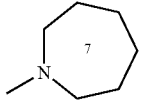
| Ex. No. | A | R¹ | R² | R³ | R⁴ | R⁵ | B | Physical Data[a] |
|---|---|---|---|---|---|---|---|---|
| I-103 | —H | -Me | -Me | —H | —H | -Me | 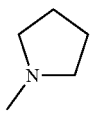 | 257 (MH⁺; 98); 172 (100) |
| I-104 | -Benzyl | -Me | -Me | —H | —H | -Me | 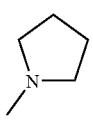 | 318 (M⁺; 2); 148 (100) |
| I-105 | —H | -Me | -Me | —H | —H | -Me | 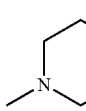 | 229 (MH⁺; 100); 144 (34) |
| I-106 | -Benzyl | -Me | -iPr | —H | —H | -Me | 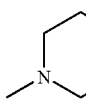 | 360 (M⁺; 2); 176 (100) |
| I-107 | —H | -Me | -iPr | —H | —H | -Me | 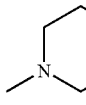 | |
| I-108 | -Benzyl | -Me | -Bn | —H | —H | -Me | 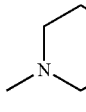 | 408 (M⁺; 1); 91 (100) |
| I-109 | —H | -Me | -Bn | —H | —H | -Me | 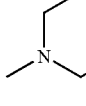 | 318 (M⁺; 0.5); 134 (100) |
| I-110 | -Benzyl | -Me | -sBu | —H | —H | -iPr | 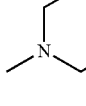 | 402 (M⁺; 3); 190 (100) |
| I-111 | —H | -Me | -sBu | —H | —H | -iPr | 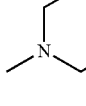 | 313 (MH⁺; 1); 112 (100) |
| I-112 | -Benzyl | -Me | -Me | —H | —H | -Me | 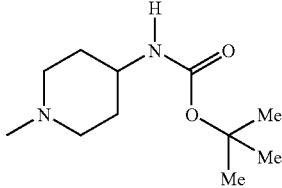 | 447 (M⁺; 3); 148 (100) |

TABLE 2-continued

Examples of compounds of the formula (I)

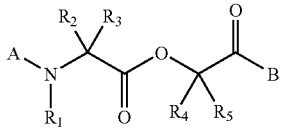

| Ex. No. | A | R¹ | R² | R³ | R⁴ | R⁵ | B | Physical Data$^{a)}$ |
|---|---|---|---|---|---|---|---|---|
| I-113 | —H | -Me | -Me | —H | —H | -Me |  | 358 (MH⁺; 100); 302 (55) |
| I-114 | -Benzyl | -Me | -Me | —H | —H | -Me | —O—Et | 293 (M⁺; 1); 148 (100) |

Abbreviation: Me: -methyl; Et: -ethyl; Pr: -propyl; Bu: -butyl; Bn: -benzyl; i-, s- and t-: iso-, secondary- and tertiary $^{a)}$FAB-MS, MS-APCl or E1-MS m/z (%);

$^{b)1}$HNMR (400 MHz, CDCl₃, δ) in ppm

The invention claimed is:

1. A method of treating an endoparasitic infection comprising administering to a human or animal in need thereof an effective amount of a didepsipeptide of the formula (I)

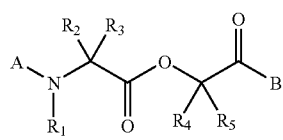

(I)

wherein

R¹ represents hydrogen, straight-chain or branched alkyl having up to 6 carbon atoms, $C_{3-6}$-cycloalkyl, aryl-$C_{1-2}$-alkyl or het-$C_{1-2}$-alkyl, R¹ and R² together with the atoms to which they are bonded represent a 5- or 6-membered ring which can optionally be interrupted by sulphur, and is optionally substituted, R² and R³ independently of one another represent hydrogen, straight-chain or branched alkyl having up to 6 carbon atoms, halogenoalkyl, hydroxyalkyl, $C_{1-4}$-alkanoyloxyalkyl, $C_{1-2}$-alkoxyalkyl, mercaptoalkyl, $C_{1-2}$-alkylthioalkyl, $C_{1-2}$-alkylsulphinylalkyl, $C_{1-2}$-alkylsulphonylalkyl, carboxyalkyl, carbamoylalkyl, aminoalkyl, $C_{1-6}$-alkylaminoalkyl, $C_{1-6}$-dialkylaminoalkyl, guanidinoalkyl, which can optionally be substituted by one or two benzyloxycarbonyl radicals or by one, two, three or four $C_{1-2}$-alkyl radicals, $C_{1-4}$-alkoxycarbonylaminoalkyl, $C_{2-6}$-alkenyl, $C_{3-6}$-cycloalkyl, $C_{3-6}$-cycloalkyl-$C_{1-2}$-alkyl, and optionally substituted aryl, aryl-$C_{1-2}$-alkyl, heteroaryl, heteroaryl-$C_{1-2}$alkyl, or R² and R³ together represent a spirocyclic ring, R⁴ and R⁵ independently of one another represent hydrogen, straight-chain or branched alkyl having up to 6 carbon atoms, halogenoalkyl, hydroxyalkyl, $C_{1-4}$-alkanoyloxyalkyl, $C_{1-2}$-alkoxyalkyl, mercaptoalkyl, $C_{1-2}$-alkylthioalkyl, $C_{1-2}$-alkylsulphinylalkyl, $C_{1-2}$-alkylsulphonylalkyl, carboxyalkyl, carbamoylalkyl, aminoalkyl, $C_{1-6}$-alkylaminoalkyl, $C_{1-6}$-dialkylaminoalkyl, guanidinoalkyl, which can optionally be substituted by one or two benzyloxycarbonyl radicals or by one, two, three or four $C_{1-2}$-alkyl radicals, $C_{1-4}$-alkoxycarbonylaminoalkyl, $C_{2-6}$-alkenyl, $C_{3-6}$-cycloalkyl, $C_{3-6}$-cycloalkyl-$C_{1-2}$-alkyl, and optionally substituted aryl, aryl-$C_{1-2}$-alkyl, heteroaryl, heteroaryl-$C_{1-2}$alkyl, or R⁴ and R⁵ together represent a spirocyclic ring, A represents hydrogen, $C_{1-6}$-alkyl, formyl, $C_{1-4}$-alkoxydicarbonyl or a radical of the group G¹

G¹ in which can denote carbonyl, thiocarboxyl, —C=CH—NO₂, —C=CH—CN, —C=N—R⁶, sulphoxyl, sulphonyl, —P(O)—OR⁷ or P(S)—OR⁷, R⁶ represents hydrogen, hydroxyl, $C_{1-4}$-alkoxy, $C_{1-4}$-alkylcarbonyl, $C_{1-4}$-halogenoalkylcarbonyl, $C_{1-4}$-alkylsulphonyl, nitro or cyano, and R⁷ represents hydrogen or $C_{1-4}$-alkyl, and Q represents straight-chain or branched $C_{1-6}$-alkyl, $C_{1-6}$-halogenoalkyl, hydroxy-$C_{1-6}$-alkyl, $C_{1-4}$-alkanoyloxy-$C_{1-6}$-alkyl, $C_{1-2}$-alkoxy-$C_{1-6}$-alkyl, mercapto-$C_{1-6}$-alkyl-, $C_{1-2}$-alkylthio-$C_{1-6}$-alkyl, $C_{1-2}$-alkylsulphinyl-$C_{1-6}$-alkyl, $C_{1-2}$-alkylsulphonyl-$C_{1-6}$-alkyl, carboxy-$C_{1-6}$-alkyl, carbamoyl-$C_{1-6}$-alkyl, amino-$C_{1-6}$-alkyl, $C_{1-6}$-alkylamino-$C_{1-6}$-alkyl, $C_{1-6}$-dialkylaminoalkyl, $C_{2-6}$-alkenyl, $C_{2-6}$-alkynyl, $C_{2-6}$-halogenoalkenyl, $C_{3-6}$-cycloalkyl, and optionally substituted aryl, aryl-$C_{1-2}$-aryl, hetaryl or hetaryl-$C_{1-2}$-alkyl, or optionally represents a radical from the group $G^2$ and $G^3$ $R^8$—Y—   $G^2$

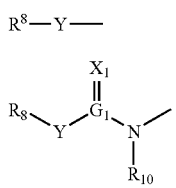   $G^3$ in which

can denote carboxyl, thiocarboxyl or sulphonyl,

Y represents oxygen, sulphur or —$NR^9$, $R^8$ in the case where Y represents nitrogen can denote a cyclic amino group linked via a nitrogen atom, $R^8$ and $R^9$ independently of one another represent hydrogen, straight-chain or branched $C_{1-6}$-alkyl, $C_{1-6}$-alkenyl, $C_{1-6}$-alkynyl, $C_{3-6}$-cycloalkyl, $C_{3-6}$-cycloalkyl-$C_{1-2}$-alkyl, aryl, arylalkyl, hetaryl, hetarylalkyl, each of which is optionally substituted, or $R^8$ and $R^9$ together with the adjacent N atom a carbocyclic 5-, 6- or 7-membered ring system or a 7 to 10-membered bicyclic ring system which can optionally also be interrupted by oxygen, sulphur, sulphoxyl, sulphonyl, carbonyl, —N—O, —N=, —$NR^{11}$— or by quaternized nitrogen and is optionally substituted, $R^{10}$ represents hydrogen or $C_{1-4}$-alkyl, $R^{11}$ represents hydrogen, straight-chain or branched $C_{1-6}$-alkyl, $C_{2-6}$-alkenyl, $C_{2-6}$-alkynyl, $C_{3-8}$-cycloalkyl, $C_{3-8}$-cycloalkyl-$C_{1-2}$-alkyl, $C_{1-4}$-alkoxycarbonyl, $C_{1-4}$-alkylcarbonyl, $C_{3-6}$-cycloalkylcarbonyl, cyan, aryl, aryl-$C_{1-2}$-alkyl, hetaryl, hetaryl-$C_{1-2}$-alkyl, each of which is optionally substituted, and B represents hydroxyl, $C_{1-6}$-alkoxy, $C_{2-6}$-alkenyloxy, $C_{2-6}$-alkynyloxy, $C_{3-7}$-cycloalkyloxy, $C_{3-7}$-cycloalkylalkyloxy, aryloxy-, aryl-$C_{1-2}$-alkyloxy, hetaryloxy, hetaryl-$C_{1-2}$-alkyloxy, each of which is optionally substituted, or represents the radicals —$NR^{12}R^{13}$, —$NR^{14}$—$NR^{12}R^{13}$ and —$NR^{15}$—$OR^{16}$, in which $R^{12}$ and $R^{13}$ independently of one another represent hydrogen, straight-chain or branched $C_{1-6}$-alkyl, $C_{1-6}$-alkylcarbonyl, $C_{1-6}$-alkylsulphonyl, $C_{2-6}$-alkenyl, $C_{2-6}$-alkynyl, $C_{3-6}$-cycloalkyl, $C_{3-8}$-cycloalkyl-$C_{1-2}$-alkyl, aryl, arylcarbonyl, arylsulphonyl, aryl-$C_{1-2}$-alkyl, hetaryl, hetarylcarbonyl, hetarylsulphonyl or hetaryl-$C_{1-2}$-alkyl, or $R^{12}$ and $R^{13}$ together with the adjacent N atom represents a carbocyclic 5-, 6-, 7-, or 8-membered ring system or a 7 to 10-membered bicyclic ring system which can optionally also be interrupted by oxygen, sulphur, sulphoxyl, sulphonyl, carbonyl, —N—O, —N=, —$NR^{11}$— or by quaternized nitrogen and is optionally substituted, $R^{14}$ represents hydrogen, straight-chain or branched $C_{1-6}$-alkyl, $C_{3-6}$-cycloalkyl, aryl-$C_{1-2}$-alkyl or hetaryl-$C_{1-2}$-alkyl, each of which is optionally substituted, $R^{15}$ and $R^{16}$ independently of one another denote hydrogen, straight-chain or branched $C_{1-6}$-alkyl, $C_{1-6}$-alkylcarbonyl, $C_{2-6}$-alkenyl, $C_{2-6}$-alkynyl, $C_{3-6}$-cycloalkyl, aryl-$C_{1-2}$-alkyl or hetaryl-$C_{1-2}$-alkyl, each of which is optionally substituted, $R^{15}$ and $R^{16}$ together with the adjacent N—O group represent a carbocyclic 5-, 6-, or 7-membered ring, or an optical isomer or salt thereof.

2. A method of treating an endoparasitic infection comprising administering to a human or animal in need thereof an effective amount of a didepsipeptide of the formula (Ia) and its salt

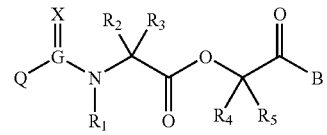   (Ia)

in which $R^1$ represents hydrogen, straight-chain or branched $C_{1-4}$-alkyl, $R^2$ represents hydrogen, straight-chain or branched alkyl having up to 6 carbon atoms alkenyl having up to 4 carbon atoms, $C_{3-6}$-cycloalkyl, $C_{3-6}$-cycloalkyl-$C_{1-2}$-alkyl, aryl, aryl-$C_{1-2}$-alkyl, hetaryl, hetaryl-$C_{1-2}$-alkyl each of which is optionally substituted, alternatively, $R^1$ and $R^2$ together with the atoms to which they are bonded represent a 5- or 6-membered ring which can optionally be interrupted by oxygen, sulphur, sulphoxyl or sulphonyl and is optionally substituted, $R^3$ and $R^4$ represent hydrogen, $R^5$ represents hydrogen, straight-chain or branched alkyl having up to 6 carbon atoms, alkenyl having up to 4 carbon atoms, $C_{3-6}$-cycloalkyl, $C_{3-6}$-cycloalkyl-$C_{1-2}$-alkyl, aryl, aryl-$C_{1-2}$-alkyl, hetaryl, hetaryl-$C_{1-2}$-alkyl each of which is optionally substituted,

represents carboxyl, thiocarboxyl, —C=CH—$NO_2$, —C=CH—CN, —C=N—$R^6$, sulphoxyl, sulphonyl, —P(O)—O—$R^7$ or P(S)—O—$R^7$, $R^6$ represents hydrogen, hydroxyl, $C_{1-4}$-alkoxy, $C_{1-4}$-alkylcarbonyl, $C_{1-4}$-halogenoalkylcarbonyl, $C_{1-4}$-alkylsulphonyl, nitro or cyano, and $R^7$ represents hydrogen or $C_{1-4}$-alkyl, and Q represents straight-chain or branched $C_{1-6}$-alkyl, $C_{2-6}$-alkenyl, $C_{2-6}$-alkynyl, $C_{3-6}$-cycloalkyl or hetaryl-$C_{1-2}$-alkyl, or optionally represents a radical from the group $G^2$ and $G^3$ $R^8$—Y—   $G^2$

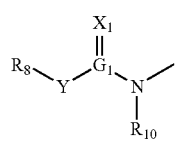   $G^3$ in which

can denote carboxyl, thiocarboxyl or sulphonyl,

Y represents oxygen, sulphur or —NR$^9$,

R$^8$ in the case where Y represents nitrogen can denote a cyclic amino group linked via a nitrogen atom, R$^8$ and R$^9$ independently of one another represents hydrogen, straight-chain or branched C$_{1-6}$-alkyl, C$_{2-6}$-alkenyl, C$_{2-6}$-alkynyl, C$_{3-6}$-cycloalkyl, C$_{3-6}$-cycloalkyl-C$_{1-2}$-alkyl, hetaryl or hetaryl-C$_{1-2}$-alkyl, each of which is optionally substituted, or R$^8$ and R$^9$ together with the adjacent N atom represent a carbocyclic 5-, 6- or 7-membered ring system or a 7 to 10-membered bicyclic ring system which can optionally also be interrupted by oxygen, sulphur, sulphoxyl, sulphonyl, carbonyl, —N—O—, —N=, —NR$^{11}$— or by quaternized nitrogen and is optionally substituted, R$^{10}$ represents hydrogen or C$_{1-4}$-alkyl, and R$^{11}$ represents hydrogen, straight-chain or branched C$_{1-6}$-alkyl, C$_{3-6}$-cycloalkyl, C$_{2-6}$-alkenyl, C$_{2-6}$-alkynyl, C$_{3-6}$-cycloalkyl, C$_{1-4}$-alkoxycarbonyl, C$_{1-4}$-alkylcarbonyl, C$_{3-6}$-cycloalkylcarbonyl, cyano, aryl, aryl-C$_{1-2}$-alkyl, hetaryl or hetaryl-C$_{1-2}$-alkyl, each of which is optionally substituted, and B represents C$_{1-6}$-alkoxy, C$_{2-6}$-alkenyloxy, C$_{2-6}$-alkynyloxy, C$_{3-7}$-cycloalkyloxy, C$_{3-7}$-cycloalkyl-C$_{1-2}$-alkyloxy, aryloxy-, aryl-C$_{1-2}$-alkyloxy, hetaryloxy, hetaryl-C$_{1-2}$-alkyloxy, each of which is optionally substituted, or represents the amino radicals —NR$^{12}$R$^{13}$, —NR$^{14}$—NR$^{12}$R$^{13}$ and —NR$^{15}$—OR$^{16}$, in which R$^{12}$ and R$^{13}$ independently of one another represent hydrogen, straight-chain or branched C$_{1-6}$-alkyl, C$_{1-6}$-alkylcarbonyl, C$_{1-6}$-alkylsulphonyl, C$_{2-6}$-alkenyl, C$_{2-6}$ alkynyl, C$_{3-8}$-cycloalkyl, C$_{3-8}$-cycloalkyl-C$_{1-2}$-alkyl, aryl, arylcarbonyl, arylsulphonyl, aryl-C$_{1-2}$-alkyl, hetaryl, hetarylcarbonyl, hetarylsulphonyl or hetaryl-C$_{1-2}$-alkyl, or R$^{12}$ and R$^{13}$ together with the adjacent N atom represent a carbocyclic 5-, 6-, 7- or 8-membered ring system or a 7 to 10-membered bicyclic ring system, which can optionally also be interrupted by oxygen, sulphur, sulphoxyl, sulphonyl, carbonyl, —N—O, —N=, —NR$^{11}$— or by quaternized nitrogen and is optionally substituted, R$^{14}$ represents hydrogen, straight-chain or branched C$_{1-6}$-alkyl, C$_{3-6}$-cycloalkyl, each of which is optionally substituted, R$^{15}$ and R$^{16}$ independently of one another denote hydrogen, straight-chain or branched C$_{1-6}$-alkyl, C$_{1-6}$-alkylcarbonyl, C$_{2-6}$-alkenyl, C$_{2-6}$-alkynyl or C$_{3-6}$-cycloalkyl, each of which is optionally substituted, and R$^{15}$ and R$^{16}$ together with the adjacent N—O-group represent a carbocyclic 5-, 6- or 7-membered ring, with the proviso in the case where in formula (Ia) R$^1$, R$^5$ and =G=X together represent the following radicals:

R$^1$ represents hydrogen and methyl,

R$^5$ represents hydrogen,

represents carboxyl, the radicals Q and B must fulfill the following condition:

Q represents radicals other than methyl,

B represents radicals other than —NH$_2$, and with the proviso in the case where in formula (Ia) G$^2$ and =G=X together represent the following radicals:

represents carboxyl,

G$^2$ represents tert-butyloxy, benzyloxy and 4-nitro-benzyloxy, the radical B represents radicals other than tert-butyloxy, benzyloxy and 4-nitro-benzyloxy, and with the proviso that, if in formula (Ia) R$^4$ and R$^5$ are hydrogen, B must not represent NH$_2$, and with the proviso that, if in formula (Ia) R$^1$ and R$^5$ represent hydrogen and

 represents 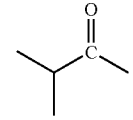

B does not represent methylamino, and with the proviso that, if in formula (Ia)

represents benzyloxycarbonyl or

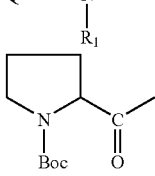 represents

B does not represent benzylamino,
and with the proviso that, if in formula (Ia)

represents tert-butyloxycarbonyl and $R^1$ and $R^3$ represent H and either $R^4$ and $R^5$ represents methyl and the other radical represents H,
B does not represent ethoxy,
and with the proviso that the compound of formula

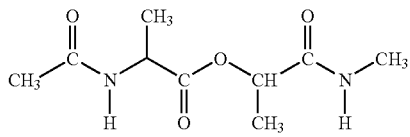

is excluded,
furthermore with the proviso that the compounds
methyl O-(N-carbobenzoxy-l-leucyl)-hydroxyethanoate,
methyl O-(N-carbobenzoxy-l-leucyl)-(S)-2-hydroxy-3-phenylpropanoate,
methyl O-(N-carbobenzoxy-l-leucyl)-(S)-2-hydroxypropanoate,
methyl O-(N-carbobenzoxy-l-leucyl)-(S)-2-hydroxy-4-methylpentanoate,
ethyl N-(benzyloxycarbonyl)amino-2-(O-glycyl)-glycolate,
ethyl N-(benzyloxycarbonyl)-amino-2-(O-glycyl)-lactate,
ethyl N-(benzyloxycarbonyl)-amino-2-(O-alanyl)-glycolate,
ethyl N-(benzyloxycarbonyl)-amino-2-(O-alanyl)-lactate
are excluded,
and their optical isomers and racemates.

\* \* \* \* \*